US011709168B2

(12) United States Patent
Van Meter et al.

(10) Patent No.: US 11,709,168 B2
(45) Date of Patent: Jul. 25, 2023

(54) BIOMARKER LEVELS AND NEUROIMAGING FOR DETECTING, MONITORING AND TREATING BRAIN INJURY OR TRAUMA

(71) Applicant: BRAINBOX SOLUTIONS, INC., Richmond, VA (US)

(72) Inventors: Timothy E. Van Meter, Richmond, VA (US); Nazanin Mirshahi, Richmond, VA (US)

(73) Assignee: BRAINBOX SOLUTIONS, INC., Richmond, VA (US)

( * ) Notice: Subject to any disclaimer, the term of this patent is extended or adjusted under 35 U.S.C. 154(b) by 198 days.

(21) Appl. No.: 16/616,051

(22) PCT Filed: May 22, 2018

(86) PCT No.: PCT/US2018/033943
§ 371 (c)(1),
(2) Date: Nov. 22, 2019

(87) PCT Pub. No.: WO2018/217792
PCT Pub. Date: Nov. 29, 2018

(65) Prior Publication Data
US 2022/0074953 A1 Mar. 10, 2022

Related U.S. Application Data

(60) Provisional application No. 62/532,180, filed on Jul. 13, 2017, provisional application No. 62/510,096, filed on May 23, 2017.

(51) Int. Cl.
*G01N 33/68* (2006.01)
*A61B 5/00* (2006.01)

(52) U.S. Cl.
CPC ....... *G01N 33/6896* (2013.01); *A61B 5/4064* (2013.01); *G01N 2800/28* (2013.01)

(58) Field of Classification Search
CPC ........... G01N 33/6896; G01N 2800/28; G01N 33/50; G01N 33/53; A61B 5/4064; A61B 5/0263; C07K 14/4713; C07K 14/475; C07K 14/47; C12N 9/88; C12Y 402/01011
See application file for complete search history.

(56) References Cited

U.S. PATENT DOCUMENTS

| 2011/0082203 A1 | 4/2011 | Wang |
| 2011/0177974 A1 | 7/2011 | Wang |
| 2014/0045713 A1 | 2/2014 | Everett |
| 2016/0178643 A1 | 6/2016 | Everett et al. |
| 2017/0023591 A1 | 1/2017 | Bowser et al. |

FOREIGN PATENT DOCUMENTS

| CN | 103118698 A | 5/2013 | |
| WO | 2010148391 A2 | 12/2010 | |
| WO | 2011147981 A2 | 12/2011 | |
| WO | WO-2012155134 A2 * | 11/2012 | ............. C07K 16/18 |
| WO | WO-2013138509 A1 * | 9/2013 | ......... G01N 33/5306 |
| WO | WO-2014152773 A1 * | 9/2014 | ........... G01N 33/566 |
| WO | 2016048488 A1 | 3/2016 | |
| WO | 2016125148 A1 | 8/2016 | |
| WO | WO-2016179426 A1 * | 11/2016 | ........... G01N 33/577 |

OTHER PUBLICATIONS

Metting et al., Neurology 78(18):1428-1433, (Year: 2012).*
Yang et al., "Serum neurogranin measurement as a biomarker of acute traumatic brain injury" Clinical Biochemistry vol. 48, Issues 13-14, Sep. 2015, pp. 843-848 (Year: 2015).*
Thelin et al., "Protein profiling in serum after traumatic brain injury in rats reveals potential injury markers" Behavioral Brain Research 340 (2018) 71-80 (Available online Aug. 31, 2016) (Year: 2016).*
Kawata et al. "Blood biomarkers for brain injury: What are we measuring?" Neurosci Biobehav Rev. Sep. 2016;68: 460-473 (Year: 2016).*
Barzo et al., "Magnetic resonance imaging-monitored acute blood-brain barrier changes in experimental traumatic brain injury", Journal of Neurosurgery, Dec. 1996, pp. 1113-1121, 85(6), Abstract, American Association of Neurological Surgeons (From IDS Dated Aug. 12, 2021 (Year: 1996).*
Korn et al., "Focal Cortical Dysfunction and Blood-Brain Barrier Disruption in Patients with Post-concussion Syndrome", Journal of Clinical Neurophysiology, Feb. 2005, 22(1), Lippincott Williams & Willkins (From IDS dated Aug. 12, 2021) (Year: 2005).*
Stamatovic, S.M., "Brain Endothelial Cell-Cell Junctions: How to "Open" the Blood Brain Barrier" 2008, Neuropharmacology, 6(3): 179-192) (Cited p. 24 of Applicant specification) (Year: 2008).*
Meco C, Arrer E, Oberascher G. 2007. Efficacy of cerebrospinal fluid fistula repair: Sensitive quality control using the beta-trace protein test. Am J Rhinol 21:729-736.
Mouser PE, Head E, Ha KH, Rohn TT. 2006. Caspase-mediated cleavage of glial fibrillary acidic protein within degenerating astrocytes of the Alzheimer's disease brain. Am J Pathol 168:936-46.
Mu J, Yang Y, Chen J, Cheng K, Li Q, Wei Y, Zhu D, Shao W, Zheng P, Xie P. 2015. Elevated host lipid metabolism revealed by iTRAQ-based quantitative proteomic analysis of cerebrospinal fluid of tuberculous meningitis patients. Biochem Biophys Res Commun 466:689-95.

(Continued)

Primary Examiner — Kimberly Ballard
Assistant Examiner — Stacey N MacFarlane
(74) Attorney, Agent, or Firm — Raphael Bellum PLLC

(57) ABSTRACT

Methods, compositions and kits useful in the detection, assessment, diagnosis, prognosis and/or treatment of brain injuries, especially mild traumatic brain injury (mTBI) or concussion, are based upon detection of changes in levels of certain protein biomarkers in a subject undergoing testing, or upon detection of changes in levels of certain protein biomarkers in conjunction with neuroimaging analyses to detect changes in vascular or blood brain barrier (BBB) permeability in the brain, or to detect damage to fiber tracts in the brain, in which changes in biomarker levels correlate with detection of changes in BBB permeability or in brain fiber tract or white matter damage in a subject with brain injury such as mTBI or concussion.

19 Claims, 51 Drawing Sheets

Figure 1A:
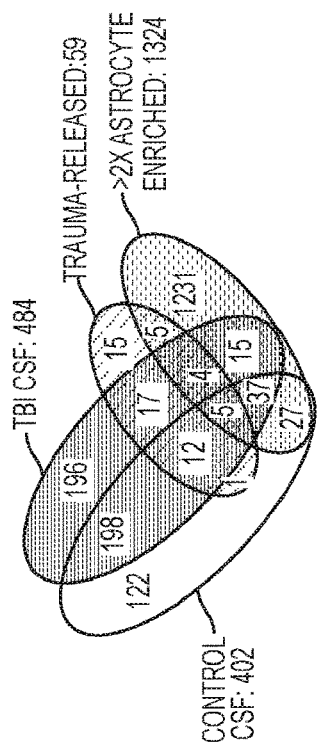

Specification includes a Sequence Listing.

(56) References Cited

OTHER PUBLICATIONS

Newcombe J, Woodroofe MN, Cuzner ML. 1986. Distribution of glial fibrillary acidic protein in gliosed human white matter. J Neurochem 47:1713-9.
Okonkwo DO, Yue JK, Puccio AM, Panczykowski DM, Inoue T, McMahon PJ, Sorani MD, Yuh EL, Lingsma HF, Maas AI and others. 2013. GFAP-BDP as an acute diagnostic marker in traumatic brain injury: results from the prospective transforming research and clinical knowledge in traumatic brain injury study. J Neurotrauma 30:1490-7.
Osman I, Gaillard O, Meillet D, Bordas-Fonfrede M, Gervais A, Schuller E, Delattre J, Legrand A. 1995. A sensitive time-resolved immunofluorometric assay for the measurement of apolipoprotein B in cerebrospinal fluid. Application to multiple sclerosis and other neurological diseases. Eur J Clin Chem Clin Biochem 33:53-8.
Osuna E, Perez-Carceles MD, Luna A, Pounder DJ. 1992. Efficacy of cerebro-spinal fluid biochemistry in the diagnosis of brain insult. Forensic Sci Int 52(2):193-8.
Pahari DR, Gu YJ, van Oeveren W, El-Essawi A, Harringer W, Brouwer RM. 2013. Effect of minimized perfusion circuit on brain injury markers camosinase and brain-type fatty binding protein in coronary artery bypass grafting patients. Artif Organs 37:128-35.
Papa L, Lewis LM, Falk JL, Zhang Z, Silvestri S, Giordano P, Brophy GM, Demery JA, Dixit NK, Ferguson I and others. 2012. Elevated levels of serum glial fibrillary acidic protein breakdown products in mild and moderate traumatic brain injury are associated with intracranial lesions and neurosurgical intervention. Ann Emerg Med 59:471-83.
Pelinka LE, Kroepfl A, Leixnering M, Buchinger W, Raabe A, Redl H. 2004a. GFAP versus S100B in serum after traumatic brain injury: relationship to brain damage and outcome. J Neurotrauma 21:1553-61.
Pelinka LE, Kroepfl A, Schmidhammer R, Krenn M, Buchinger W, Redl H, Raabe A. 2004b. Glial fibrillary acidic protein in serum after traumatic brain injury and multiple trauma. J Trauma 57:1006-12.
Pelsers MM, Hanhoff T, Van der Voort D, Arts B, Peters M, Ponds R, Honig A, Rudzinski W, Spener F, de Kruijk JR and others. 2004. Brain-and heart-type fatty acid-binding proteins in the brain: tissue distribution and clinical utility. Clin Chem 50:1568-75.
Reiber H, Walther K, Althaus H. 2003. Beta-trace protein as sensitive marker for CSF rhinorhea and CSF otorhea. Acta Neurol Scand 108:359-62.
Rivett AJ. 1985. Preferential degradation of the oxidatively modified form of glutamine synthetase by intracellular mammalian proteases. J Biol Chem 260:300-5.
Rohn TT, Catlin LW, Poon WW. 2013. Caspase-cleaved glial fibrillary acidic protein within cerebellar white matter of the Alzheimer's disease brain. Int J Clin Exp Pathol 6:41-8.
Shen S, Loo RR, Wanner IB, Loo J. Addressing the needs of traumatic brain injury with clinical proteomics. Clin Proteomics. Mar. 28, 2014;11(1):11. doi: 10.1186/1559-0275-11-11.
Stoevring B, Frederiksen JL, Christiansen M. 2007. CRYAB promoter polymorphisms: influence on multiple sclerosis susceptibility and clinical presentation. Clin Chim Acta 375:57-62.
Teunissen CE, Veerhuis R, De Vente J, Verhey FR, Vreeling F, van Boxtel MP, Glatz JF, Pelsers MA. 2011. Brain-specific fatty acid-binding protein is elevated in serum of patients with dementia-related diseases. Eur J Neurol 18:865-71.
Timmer NM, Herbert MK, Claassen JA, Kuiperij HB, Verbeek MM. 2015. Total glutamine synthetase levels in cerebrospinal fluid of Alzheimer's disease patients are unchanged. Neurobiol Aging 36:1271-3.
Vadakkan KI, Mammen T, Wadhwa VS. 2015. Sum of two catalytic activities of the glutamine synthetase enzyme is a blood biomarker for stroke and is optimized for a rapid diagnostic test. Int J Stroke 10:E1-2.
Vazquez MD, Sanchez-Rodriguez F, Osuna E, Diaz J, Cox DE, Perez-Carceles MD, Martinez P, Luna A, Pounder DJ. 1995. Creatine kinase BB and neuron-specific enolase in cerebrospinal fluid in the diagnosis of brain insult. Am J Forensic Med Pathol 16:210-4.
Vermeiren Y, Le Bastard N, Clark CM, Engelborghs S, De Deyn PP. 2011. Serum glutamine synthetase has no value as a diagnostic biomarker for Alzheimer's disease. Neurochem Res 36:1858-62.
Wanner Ina B., et al., Profiling the Injury Signature of Astrocytes for New Neurotrauma Biomarkers. Abstract from The 30th Annual National Neurotrauma Symposium.Jul. 22-25, 2012. Phoenix Arizona. p. A-61.
Wanner Ina B., et al., Profiling the Injury Signature of Astrocytes for New Neurotrauma Biomarkers. Poster Presented 2012. Phoenix Arizona.
Wijman, C.A.C., et al., Research and Technology in Neurocritical Care. Neurocrit Care. Feb. 2012 ; 16(1): 42-54.
Wunderlich MT, Hanhoff T, Goertler M, Spener F, Glatz JF, Wallesch CW, Pelsers MM. 2005. Release of brain-type and heart-type fatty acid-binding proteins in serum after acute ischaemic stroke. J Neurol 252:718-24.
Yan X, Liu T, Yang S, Ding Q, Liu Y, Zhang X, Que H, Wei K, Luo Z, Liu S. 2009. Proteomic profiling of the insoluble pellets of the transected rat spinal cord. J Neurotrauma 26:179-93.
Yang Z, Wang KK. 2015. Glial fibrillary acidic protein: from intermediate filament assembly and gliosis to neurobiomarker. Trends Neurosci 38:364-374.
Zhang, Zhiqun, et al., Human Traumatic Brain Injury Induces Autoantibody Response against Glial Fibrillary Acidic Protein and Its Breakdown Products. PLoS ONE 9(3): e92698.
Zhao X, Ahram A, Berman RF, Muizelaar JP, Lyeth BG. 2003. Early loss of astrocytes after experimental traumatic brain injury. Glia 44:140-52.
Zoltewicz JS, Scharf D, Yang B, Chawla A, Newsom KJ, Fang L. 2012. Characterization of Antibodies that Detect Human GFAP after Traumatic Brain Injury. Biomark Insights 7:71-9.
International Search Report and Written Opinion for PCT/US2016/031043 (W016179426 dated Nov. 10, 2016).
Hulscher et al., "The Diagnostic Value of Brain-Fatty Acid Bidning Protein in Traumatic Brain Injury", Journal of Neurotrauma, 31:411, Feb. 15, 2014.
Kou et al., "Combining Biochemical and Imaging Markers to Improve Diagnosis and Characterization of Mild Traumatic Brain Injury in the Acute Setting: Results from a Pilot Study", PLOS One, Nov. 2013, vol. 8, Issue 11, e80296.
Arrer E, Meco C, Oberascher G, Piotrowski W, Albegger K, Patsch W. 2002. beta-Trace protein as a marker for cerebrospinal fluid rhinorrhea. Clin Chem 48:939-41.
Asaka M, Kimura T, Nishikawa S, Saitoh M, Miyazaki T, Takatori T, Alpert E. 1990. Serum aldolase isozyme levels in patients with cerebrovascular diseases. Am J Med Sci 300(5):291-5.
Bachmann-Harildstad G, Stenklev NC, Myrvoll E, Jablonski G, Klingenberg O. 2011. beta-trace protein as a diagnostic marker for perilymphatic fluid fistula: a prospective controlled pilot study to test a sample collection technique. Otol Neurotol 32:7-10.
Bachmann-Harildstad G. 2008. Diagnostic values of beta-2 transferrin and beta-trace protein as markers for cerebrospinal fluid fistula. Rhinology 46:82-5.
Barzo, P, et al. Magnetic resonance imaging-monitored acute blood-brain barrier changes in experimental traumatic brain injury. J Neurosurg 85:1113-1121, 1996.
Bourguignat A, Ferard G, Jung G, Klumpp T, Metais P. 1983. Multivariate analysis of plasma enzyme profiles in severe head injury. Clin Chem 29:107-9.
Brettschneider J, Riepe MW, Petereit HF, Ludolph AC, Tumani H. 2004. Meningeal derived cerebrospinal fluid proteins in different forms of dementia: is a meningopathy involved in normal pressure hydrocephalus? J Neurol Neurosurg Psychiatry 75:1614-6.
Buki, A. et al. (2015) Minor and Repetitive Head Injury. In: Schramm J. (eds) Advances and Technical Standards in Neurosurgery. Advances and Technical Standards in Neurosurgery, vol. 42. Springer, Cham.

(56) References Cited

OTHER PUBLICATIONS

Chang RY, Etheridge N, Dodd PR, Nouwens AS. 2014. Targeted quantitative analysis of synaptic proteins in Alzheimer's disease brain. Neurochem Int 75:66-75.
Chen MH, Hagemann TL, Quinlan RA, Messing A, Perng MD. 2013. Caspase cleavage of GFAP produces an assembly-compromised proteolytic fragment that promotes filament aggregation. ASN Neuro 5:e00125.
Ding B, Xi Y, Gao M, Li Z, Xu C, Fan S, He W. 2014. Gene expression profiles of entorhinal cortex in Alzheimer's disease. Am J Alzheimers Dis Other Demen 29(6):526-32.
Feala, Jacob D., et al., Systems Biology Approaches for Discovering Biomarkers for Traumatic Brain Injury Journal of Neurotrauma. Jul. 2013, 30(13): 1101-1116.
Florez G, Cabeza A, Gonzalez JM, Garcia J, Ucar S. 1976. Changes in serum and cerebrospinal fluid enzyme activity after head injury. Acta Neurochir (Wien) 35(1-3):3-13.
Gao WM, Chadha MS, Berger RP, Omenn GS, Allen DL, Pisano M, Adelson PD, Clark RS, Jenkins LW, Kochanek PM. 2007. A gel-based proteomic comparison of human cerebrospinal fluid between inflicted and non-inflicted pediatric traumatic brain injury. J Neurotrauma 24:43-53.
Hausdoerfer J, Heller W, Schinkmann L. 1975. Biochemical and biophysical changes in guinea pigs after acute head injury. Resuscitation 4(2):77-86.
Hicks, RR, et al. Mild Experimental Brain Injury in the Rat Induces Cognitive Deficits Associated with Regional Neuronal Loss in the Hippocampus. 1993 J of Neurotrauma 10(4):405-414.
Ichkova, Aleksandra and Badaut, Jerome. New biomarker stars for traumatic brain injury. Journal of Cerebral Blood Flow & Metabolism. 2017, vol. 37(10) 3276-3277.
Jung G, Morel J, Bourguignat A, Ferard G. 1983. Modifications of plasma enzyme activities after severe head injury; evaluation of prognosis using multivariate methods. Clin Chim Acta 127(3):365-71.
Kay AD, Day SP, Nicoll JA, Packard CJ, Caslake MJ. 2003. Remodelling of cerebrospinal fluid lipoproteins after subarachnoid hemorrhage. Atherosclerosis 170:141-6.
Ke K, Li L, Rui Y, Zheng H, Tan X, Xu W, Cao J, Xu J, Cui G, Xu G and others. 2013. Increased expression of small heat shock protein alphaB-crystallin after intracerebral hemorrhage in adult rats. J Mol Neurosci 51:159-69.
Klun B. 1974. Spinal fluid and blood serum enzyme activity in brain injuries. J Neurosurg 41(2):224-8.
Koh, DW, Dawson TM, Dawson VL. Mediation of cell death by poly(ADP-ribose) polymerase-1. Pharmacol Res. Jul. 2005;52(1):5-14.
Koh, L., et al. Development of cerebrospinal fluid absorption sites in the pig and rat: connections between the subarachnoid space and lymphatic vessels in the olfactory turbinates. Anat Embryol (Berl). Aug. 2006;211(4):335-44. Epub Mar. 10, 2006.
Koh, Phil-Ok, Melatonin prevents down-regulation of astrocytic phosphoprotein PEA-15 in ischemic brain injury. J of Pineal Research, vol. 51, Issue 4, Nov. 2011, pp. 381-386.
Koh, Phil-Ok. 2012a. Ferulic acid prevents the cerebral ischemic injury-induced decreases of astrocytic phosphoprotein PEA-15 and its two phosphorylated forms. Neurosci Lett 511:101-5.
Koh, Phil-Ok. 2012b. Nicotinamide attenuates the decrease of astrocytic phosphoprotein PEA-15 in focal cerebral ischemic injury. J Vet Med Sci 74:377-80.
Koh, Phil-Ok. Gingko biloba Extract (EGb 761) Attenuates the Focal Cerebral Ischemic Injury-Induced Decrease in Astrocytic Phosphoprotein PEA-15 Levels. The American Journal of Chinese Medicine, vol. 39, No. 5, 971-979. DOI: 10.1142/S0192415X11009342.
Korn, Akira, et al. Focal Cortical Dysfunction and Blood-Brain Barrier Disruption in Patients With Postconcussion Syndrome. Journal of Clinical Neurophysiology. vol. 22, No. 1, Feb. 2005. pp. 1-9.

Kulhanek, V. Die Aldolaseaktivaet in Der Cerebrospinalen Fluessigkeit Nach Intrakranialen Verletzungen. Monatsschrift fur Unfallheilkunde, Versicherungs-, Versorgungs-und Verkehrsmedizin. 1963. 365-9.
Lee A, Lingwood BE, Bjorkman ST, Miller SM, Poronnik P, Barnett NL, Colditz P, Pow DV. 2010. Rapid loss of glutamine synthetase from astrocytes in response to hypoxia: implications for excitotoxicity. J Chem Neuroanat 39:211-20.
Linke S, Goertz P, Baader SL, Gieselmann V, Siebler M, Junghans U, Kappler J. 2006. Aldolase C/zebrin II is released to the extracellular space after stroke and inhibits the network activity of cortical neurons. Neurochem Res 31(11):1297-303.
Lubieniecka JM, Streijger F, Lee JH, Stoynov N, Liu J, Mottus R, Pfeifer T, Kwon BK, Coorssen JR, Foster LJ and others. 2011. Biomarkers for severity of spinal cord injury in the cerebrospinal fluid of rats. PLoS One 6:e19247.
Lumpkins KM, Bochicchio GV, Keledjian K, Simard JM, McCunn M, Scalea T. 2008. Glial fibrillary acidic protein is highly correlated with brain injury. J Trauma 65:778-82; discussion 782-4.
Martinez A, Carmona M, Portero-Otin M, Naudi A, Pamplona R, Ferrer I. 2008. Type-dependent oxidative damage in frontotemporal lobar degeneration: cortical astrocytes are targets of oxidative damage. J Neuropathol Exp Neurol 67:1122-36.
Mase M, Yamada K, Iwata A, Matsumoto T, Seiki K, Oda H, Urade Y. 1999. Acute and transient increase of lipocalin-type prostaglandin D synthase (beta-trace) level in cerebrospinal fluid of patients with aneurysmal subarachnoid hemorrhage. Neurosci Lett 270:188-90.
Mase M, Yamada K, Shimazu N, Seiki K, Oda H, Nakau H, Inui T, Li W, Eguchi N, Urade Y. 2003. Lipocalin-type prostaglandin D synthase (beta-trace) in cerebrospinal fluid: a useful marker for the diagnosis of normal pressure hydrocephalus. Neurosci Res 47:455-9.
Mathiisen TM, et al. The perivascular astroglial sheath provides a complete covering of the brain microvessels: an electron microscopic 3D reconstruction. Glia. Jul. 2010;58(9):1094-103. doi: 10.1002/glia.20990.
McMahon PJ, Panczykowski DM, Yue JK, Puccio AM, Inoue T, Sorani MD, Lingsma HF, Maas AI, Valadka AB, Yuh EL and others. 2015. Measurement of the glial fibrillary acidic protein and its breakdown products GFAP-BDP biomarker for the detection of traumatic brain injury compared to computed tomography and magnetic resonance imaging. J Neurotrauma 32:527-33.
Meco C, Oberascher G, Arrer E, Moser G, Albegger K. 2003. Beta-trace protein test: new guidelines for the reliable diagnosis of cerebrospinal fluid fistula. Otolaryngol Head Neck Surg 129:508-17.
Metting et al., "GFAP and S100B in the acute phase of mild traumatic brain injury", Neurology 78, May 2012, pp. 1428-1433.
Yang et al., "Expressive proteomics profile changes of injured human brain cortex due to acute brain trauma", Brain Injury, Sep. 2009, 23(10): 830-840.
Zhang et al., "Biomarkers of Traumatic Brain Injury and Their Relationship to Pathology", Translational Research in Traumatic Brain Injury, 2015, pp. 263-276.
International Search Report and Written Opinion in International Application No. PCT/US18/33943, dated Sep. 27, 2018.
International Preliminary Report in Patentability International Application No. PCT/US18/33943, dated May 23, 2017.
Barzo et al., "Magnetic resonance imaging-monitored acute blood-brain barrier changes in experimental traumatic brain injury", Journal of Neurosurgery, Dec. 1996, pp. 1113-1121, 85(6), Abstract, American Association of Neurological Surgeons.
Zhang et al., "Chapter 12 Biomarkers of Traumatic Brain Injury and Their Relationship to Pathology", Translational Research in Traumatic Brain Injury, 2016, CRC Press/Taylor and Francis Group.
Korn et al., "Focal Cortical Dysfunction and Blood-Brain Barrier Disruption in Patients with Postconcussion Syndrome", Journal of Clinical Neurophysiology, Feb. 2005, 22(1), Lippincott Williams & Willkins.

(56) References Cited

OTHER PUBLICATIONS

Metting et al. "GFAP and S100B in the acute phase of mild traumatic brain injury", Neurology, May 1, 2012, 78(18), Department of Neurology, University Medical Centre Groningen, University of Groningen, Groningen, The Netherlands.
Kou et al. Combining Biochemical and Imaging Markers to Improve Diagnosis and Characterization of Mild Traumatic Brain Injury in the Acute Setting: Results from a Pilot Study, PLoS One, Nov. 2013, 8(11).

\* cited by examiner

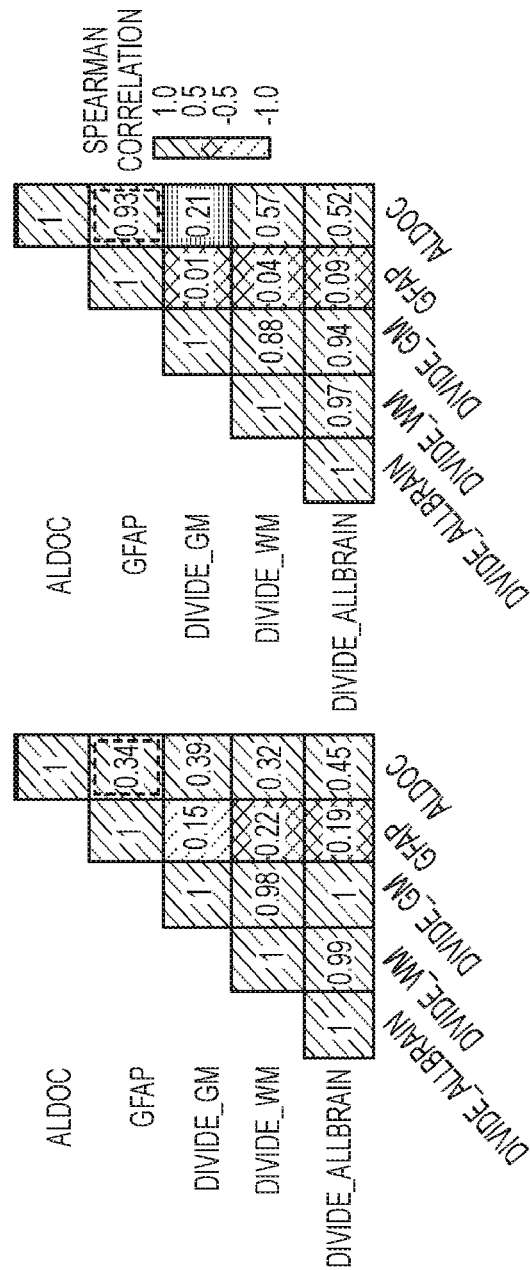

| ALDOC AND GFAP CORRELATION WITH FIBER TRACT LESIONS BY DTI (SPEARMAN) | |
|---|---|
| DTI CHANGES | CORRELATION (P) |
| CINGULUM CINGULATE/ HIPPOC. | ALDOC p=0.7/0.8 |
| ILF | ALDOC p=0.8 |
| CORPUS CALL F MAJ | ALDOC p=0.8 |
| IFOF | ALDOC/ GFAP p=0.8 |

FIG. 4H

| NRGN MARKER | NRGN | NUMBER OF SUBJECTS INCLUDED | CORRELATION COEFFICIENT(rho) |
|---|---|---|---|
| | NRGN | 22 | 1 |
| | LEFT.CINGULUM.HIPPOCAMPUS_MD | 5 | 0.7 |
| | LEFT.CINGULUM.HIPPOCAMPUS_RD | 5 | 0.7 |
| | ASYMMERTY.13 | 6 | 0.657142857 |
| | ASYMMERTY.22 | 6 | 0.6 |
| | RIGHT.SLF_FA | 20 | 0.563369728 |
| | RIGHT.SLF_AD | 20 | 0.549830802 |
| | RIGHT.ILF_FD | 15 | 0.539285714 |
| | LEFT.IFOF_AD | 7 | 0.535714286 |
| | RIGHT.CINGULUM.CINGULATE_FA | 7 | -0.535714286 |
| | LEFT.CINGULUM.HIPPOCAMPUS_FA | 5 | -0.9 |

FIG. 10A

| SNCB MARKER | SNCB | NUMBER OF SUBJECTS INCLUDED | CORRELATION COEFFICIENT(rho) |
|---|---|---|---|
| | SNCB | 23 | 1 |
| | LEFT.IFOF_RD | 7 | 0.785714286 |
| | RIGHT.IFOF_FA | 13 | 0.659340659 |
| | LEFT.IFOF_MD | 7 | 0.642857143 |
| | RIGHT.CINGULUM.HIPPOCAMPUS_FA | 8 | 0.619047619 |
| | RIGHT.IFOF_AD | 13 | 0.615384615 |
| | LEFT.CINGULUM.HIPPOCAMPUS_FA | 5 | 0.6 |
| | LEFT.ILF_FA | 18 | 0.533539732 |
| | LEFT.ILF_AD | 18 | 0.517027864 |
| | RIGHT.ARCUATE_MD | 16 | -0.517647059 |
| | CALLOSUM.FORCEPS.MAJ_AD | 12 | -0.552447552 |
| | CALLOSUM.FORCEPS.MAJ_MD | 12 | -0.573426573 |
| | ASYMMERTY.11 | 7 | -0.607142857 |
| | RIGHT.CINGULUM.HIPPOCAMPUS_MD | 8 | -0.619047619 |
| | RIGHT.CINGULUM.HIPPOCAMPUS_RD | 8 | -0.619047619 |
| | LEFT.CINGULUM.CINGULATE_RD | 10 | -0.624242424 |
| | ASYMMERTY.30 | 5 | 0.7 |
| | ASYMMERTY.20 | 7 | -0.714285714 |
| | LEFT.CINGULUM.HIPPOCAMPUS_AD | 5 | -0.9 |

FIG. 10B

| NSE MARKER | NSE | NUMBER OF SUBJECTS INCLUDED | CORRELATION COEFFICIENT(rho) |
|---|---|---|---|
| | NSE | 22 | 1 |
| | ASYMMERTY.30 | 5 | 0.8 |
| | LEFT.IFOF_FA | 8 | 0.714285714 |
| | LEFT.CINGULUM.HIPPOCAMPUS_AD | 6 | 0.657142857 |
| | ASYMMERTY.34 | 16 | 0.620588235 |
| | ASYMMERTY.7 | 16 | 0.597058824 |
| | ASYMMERTY.31 | 7 | -0.535714286 |
| | RIGHT.CINGULUM.HIPPOCAMPUS_AD | 7 | -0.642857143 |
| | LEFT.IFOF_RD | 8 | -0.666666667 |
| | LEFT.IFOF_MD | 8 | -0.69047619 |

FIG. 10C

| GFAP MARKER | GFAP | | CORRELATION COEFFICIENT(rho) |
|---|---|---|---|
| | GFAP | 22 | 1 |
| | ASYMMERTY.30 | 4 | 0.8 |
| | ALDOC | 12 | 0.797202797 |
| | LEFT.IFOF_FA | 6 | 0.771428571 |
| | ASYMMERTY.2 | 5 | 0.7 |
| | OMG | 17 | 0.597053399 |
| | RIGHT.CORTICOSPINAL_AD | 20 | -0.509774436 |
| | RIGHT.CORTICOSPINAL_FA | 20 | -0.517293233 |
| | ASYMMERTY.9 | 16 | -0.517647059 |
| | ASYMMERTY.25 | 16 | -0.532352941 |
| | LEFT.IFOF_RD | 6 | -0.542857143 |
| | ASYMMERTY.27 | 16 | -0.544117647 |
| | RIGHT.CINGULUM.HIPPOCAMPUS_FA | 5 | -0.6 |
| | RIGHT.CINGULUM.CINGULATE_RD | 5 | -0.6 |
| | ASYMMERTY.22 | 5 | -0.8 |
| | ASYMMERTY.20 | 5 | -1 |

FIG. 10D

| BDNF MARKER | | NUMBER OF SUBJECTS INCLUDED | CORRELATION COEFFICIENT(rho) |
|---|---|---|---|
| | BDNF | 25 | 1 |
| | ASYMMERTY.3 | 5 | 0.7 |
| | RIGHT.CINGULUM.HIPPOCAMPUS_RD | 8 | 0.666666667 |
| | RIGHT.CINGULUM.HIPPOCAMPUS_MD | 8 | 0.547619048 |
| | ASYMMERTY.24 | 23 | -0.518774704 |
| | LEFT.IFOF_AD | 8 | -0.523809524 |
| | ASYMMERTY.12 | 5 | -0.7 |
| | RIGHT.CINGULUM.HIPPOCAMPUS_FA | 8 | -0.80952381 |

FIG. 10E

| OMG MARKER | | NUMBER OF SUBJECTS INCLUDED | CORRELATION COEFFICIENT(rho) |
|---|---|---|---|
| | OMG | 19 | 1 |
| | RIGHT.CINGULUM.CINGULATE_FA | 7 | 0.704186851 |
| | ALDOC | 10 | 0.660606061 |
| | ASYMMERTY.30 | 5 | 0.615587011 |
| | GFAP | 17 | 0.597053399 |
| | RIGHT.CINGULUM.CING_AD | 7 | 0.555936987 |
| | ASYMMERTY.27 | 16 | -0.506680568 |
| | LEFT.IFOF MD | 8 | -0.545397261 |
| | ASYMMERTY.13 | 7 | -0.571380045 |
| | RIGHT.CINGULUM.CINGULATE_RD | 7 | -0.630061919 |
| | LEFT.SLF_FA | 18 | -0.652498403 |

FIG. 10F

| ALDOC MARKER | | NUMBER OF SUBJECTS INCLUDED | CORRELATION COEFFICIENT (rho) |
|---|---|---|---|
| | ALDOC | 12 | 1 |
| | LEFT.CINGULUM.HIPPOCAMOPUS_FA | 3 | 1 |
| | ASYMMERTY.3 | 2 | 1 |
| | ASYMMERTY.30 | 2 | 1 |
| | LEFT.IFOF_FA | 4 | 0.8 |
| | CALLOSUM.FORCEPS.MAJ_AD | 4 | 0.8 |
| | GFAP | 12 | 0.797202797 |
| | DIVIDE_WM | 12 | 0.664335664 |
| | OMG | 10 | 0.660606061 |
| | LEFT.CINGULUM.CINGULATE_FA | 6 | 0.657142857 |
| | RIGHT.ARCUATE_AD | 9 | 0.616666667 |
| | DIVIDE_ALLBRAIN | 12 | 0.608391608 |
| | ASYMMERTY | 9 | 0.55 |
| | LEFT.THALAMIC.RADIATION_MD | 10 | -0.527272727 |
| | LEFT.UNCINATE_RD | 10 | -0.587878788 |
| | LEFT.CINGULUM.CINGULATE_RD | 6 | -0.06 |
| | LEFT.UNCINATE_MD | 10 | -0.648484848 |
| | ASYMMERTY.18 | 9 | -0.666666667 |
| | ASYMMERTY.32 | 8 | -0.666666667 |
| | RIGHT.CORTICOSPINAL_AD | 11 | -0.709090909 |
| | LEFT.IFOF_MD | 4 | -0.8 |
| | LEFT.IFOF_AD | 4 | -0.8 |
| | ASYMMERTY.9 | 9 | -0.85 |
| | RIGHT.CINGULUM.HIPPOCAMPUS_MD | 3 | -1 |
| | ASYMMERTY.12 | 2 | -1 |

FIG. 10G

KEY:

MRI METRICS::

| | |
|---|---|
| AD | AXIAL DIFFUSIVITY |
| MD | MEAN DIFFUSIVITY |
| RD | RADIAL DIFFUSIVITY |
| FA | FOCAL ANISOTROPY |

FIBER TRACTS

| | |
|---|---|
| ILF | INFERIOR LATERAL FASCICULUS |
| SLF | SUOERIOR LATERAL FASCICULUS |
| IFOF | INFERIOR FRONTOOCCIPITAL FASCICULUS |
| CORTICOSPINAL | CONRTICOSPINAL TRACT |
| CALLOSUM.FORCEPS.MAJ | CORPUS CALLOSUM FORCEPS MAJOR |
| ARCUATE | ARCUATE FACICULUS |
| UNCINATE | UNCINATE FACICULUS |

*OTHERS AS WRITTEN

FIG. 10G
CONTINUED

KEY TO CT IMAGING ANALYSIS RESULTS

- GROUP 1 (G1) N IS THE # CT POSITIVE PATIENTS WITHOUT THE CT FEATURE
- GROUP 2 (G2) N IS THE # CT POSITIVE PATIENTS *WITH THE CT FEATURE PRESENT.*

- STATISTICS:
- FOUR SEPARATE STATISTICAL TESTS WERE USED TO DETERMINE SIGNIFICANT CHANGES IN BIOMARKER LEVEL COMPARED TO CT NEGATIVE PATIENTS:
  - P-VALUE (WILCOXON) LOOKS AT THE RANK SUM TEST COMPARING MEDIAN VALUES FOR BIOMARKER DISTRIBUTIONS IN EACH GROUP.
  - T-VALUE COMPARES MEANS OF BIOMARKER DISTRIBUTIONS BETWEEN GROUPS. (PAIRED T-TEST).
  - P-VALUE (PERM-EXACT.MC) EXACT MATCH PERMUTATION TEST COMPARING THE BIOMARKER DISTRIBUTIONS
  - SIGNIFICANCE FOR ALL TESTS IS SET AT 0.05-0.1 (90-95% CONFIDENCE)
- "ABSENT" INDICATES CT POSITIVE FINDINGS WERE PRESENT BUT NOT FEATURE BEING EXAMINED.

TABLE: ACUTE_SUBDURAL_HEMATOMA

| FEATURE | P-VALUE (WILCOXON) | T-VALUE | P-VALUE (PERM-EXACT.MC) | N (G1) | N (G2) |
|---|---|---|---|---|---|
| | | | | #GROUP 1 | #GROUP2 (WITH FEATURE) |
| ## NRGN (NEUROGRANIN) | | | | MSD ASSAY FORMAT | |
| ## BDNF (BRAIN DERIVED NEUROTROPHIC FACTOR) | | | | MSD ASSAY FORMAT | |
| ## GFAP (GLIAL FIBRILLARY ACIDIC PROTEIN) | | | | MSD ASSAY FORMAT | |
| ## NSE (NEURON SPECIFIC ENOLASE, ENO2) | | | | MSD ASSAY FORMAT | |
| ## SNCB (SYNUCLEIN BETA ANTIBODY PAIR 1) | | | | COLORIMETRIC ENDPOINT ELISA ASSAY FORMAT | |
| ## OMG (OLIGODENDROCYTE MYELIN GLYCOPROTEIN) | | | | MSD ASSAY FORMAT | |
| ## ALDOC (ALDOLASE C) | | | | MSD ASSAY FORMAT | |
| ## SNCB_MSD (SYNUCLEIN BETA ANTIBODY PAIR 1) | | | | MSD ASSAY FORMAT | |
| ## SNCB_MSD2 (SYNUCLEIN BETA ANTIBODY PAIR 2) | | | | MSD ASSAY FORMAT | |
| ## GFAP_AP (GLIAL FIBRILLARY ACIDIC PROTEIN- AFFINITY PURIFIED CAPTURE AB) | | | | MSD ASSAY FORMAT | |

FIG. 11A

EPIDURAL HEMORRHAGE

| FEATURE | P-VALUE(WILCOXON) | T-VALUE | P-VALUE(PERM-EXACT.MC) | N (G1) | N (G2)* |
|---|---|---|---|---|---|
| NRGN | 0.0693 | 0.0707439 | 0.1169415 | 380 | 6 |
| BDNF | 0.4014 | 0.8143833 | 0.7501249 | 385 | 6 |
| GFAP | 0.0685 | 0.0378223 | 0.0864568 | 380 | 6 |
| NSE | 0.1499 | 0.0484174 | 0.4482759 | 385 | 6 |
| SNCB | 0.2331 | 0.3108237 | 0.2948526 | 328 | 4 |
| ALDOC | 0.7289 | 0.4998408 | 0.7611194 | 70 | 4 |
| GFAP_AP | 0.1025 | 0.0627409 | 0.1874063 | 346 | 6 |

*NUMBERS ARE SMALL IN AFFECTED (GROUP 2), (G2), AND COMPARISON MAY THEREFORE BE UNRELIABLE.

FIG. 11B
CONTINUED

SUBARACHNOID HEMORRHAGE

| FEATURE | P-VALUE (WILCOXON) | T-VALUE | P-VALUE (PERM-EXACT.MC) | N (G1) | N (G2) |
|---|---|---|---|---|---|
| NRGN | 0.1716 | 0.2776506 | 0.2823588 | 380 | 60 |
| BDNF | 0.3497 | 0.1315495 | 0.0544728 | 385 | 60 |
| GFAP | 0.0003 | 0.0020732 | 0.0044978 | 380 | 60 |
| NSE | 0.0000 | 0.0000663 | 0.0004998 | 385 | 60 |
| SNCB | 0.9887 | 0.9494755 | 0.9385307 | 328 | 53 |
| OMG | 0.5568 | 0.9898036 | 0.9935032 | 36 | 4* |
| ALDOC | 0.0181 | 0.0137466 | 0.0359820 | 70 | 10 |
| SNCB_MSD | 0.4012 | 0.7901803 | 0.7641179 | 41 | 25 |
| GFAP_AP | 0.0000 | 0.0000000 | 0.0004998 | 346 | 59 |

FIG. 11C
CONTINUED

ACUTE SUBDURAL HEMORRHAGE

| FEATURE | P-VALUE (WILCOXON) | T-VALUE | P-VALUE (PERM-PCLT) | P-VALUE(PERM-EXACT.MC) | N(G1) | N(G2) |
|---|---|---|---|---|---|---|
| NRGN | 0.0439 | 0.0822933 | 0.9727042 | 0.0639680 | 381 | 40 |
| BDNF | 0.8491 | 0.5343827 | 0.2270279 | 0.4887556 | 386 | 40 |
| GFAP | 0.0079 | 0.0912574 | 0.9636304 | 0.0719640 | 381 | 40 |
| NSE | 0.0008 | 0.0078615 | 0.9973872 | 0.0054973 | 386 | 40 |
| SNCB | 0.1742 | 0.1346787 | 0.1240050 | 0.2408796 | 329 | 34 |
| OMG | NA | NA | NA | NA | 36 | 1 |
| ALDOC | 0.1343 | 0.1200845 | 0.0601036 | 0.1119440 | 70 | 5 |
| SNCB_MSD | .05229 | 0.7199335 | 0.6281886 | 0.7416292 | 42 | 17 |
| SNCB_MSD2 | NA | NA | NA | NA | 29 | 1 |
| GFAP_AP | 0.0000 | 0.0000029 | 1.0000000 | 0.0004998 | 347 | 39 |

FIG. 11D
CONTINUED

INTRAVENTRICULAR HEMORRHAGE

| FEATURE | P-VALUE(WILCOXON) | T-VALUE | P-VALUE (PERM-PCLT) | P-VALUE (PERM-EXACT.MC) | N(G1) | N(G2) |
|---|---|---|---|---|---|---|
| NRGN | 0.3941 | 0.3407540 | 0.7888753 | 0.4107946 | 384 | 6 |
| BDNF | 0.0781 | 0.1820951 | 0.0844127 | 0.1624188 | 389 | 6 |
| GFAP | 0.3856 | 0.1428687 | 0.8260108 | 0.3618191 | 384 | 6 |
| NSE | 0.2337 | 0.2862500 | 0.8385888 | 0.3103448 | 389 | 6 |
| SNCB | 0.9479 | 0.8482091 | 0.4205054 | 0.8305847 | 332 | 6 |
| OMG | NA | NA | NA | NA | 37 | 0 |
| ALDOC | NA | NA | NA | NA | 71 | 0 |
| SNCB_MSD | 0.7250 | 0.4663386 | 0.2437426 | 0.5152424 | 41 | 3 |
| SNCB_MSD2 | NA | NA | NA | NA | 29 | 0 |
| GFAP_AP | 0.0366 | 0.0570294 | 0.9795259 | 0.0469765 | 350 | 6 |

FIG. 11E
CONTINUED

MIDLINE SHIFT SUPRATENTORIAL

| FEATURE | P-VALUE (WILCOXON) | T-VALUE | P-VALUE (PERM-EXACT.MC) | N (G1) | N (G2)* |
|---|---|---|---|---|---|
| NRGN | 0.1665 | 0.3757268 | 0.1589205 | 380 | 4 |
| BDNF | 0.8810 | 0.7117819 | 0.4952524 | 385 | 4 |
| GFAP | 0.0244 | 0.0288104 | 0.0519740 | 380 | 4 |
| NSE | 0.3548 | 0.4551844 | 0.4622689 | 385 | 4 |
| SNCB | 0.6299 | 0.4633360 | 0.7276362 | 328 | 3 |
| GFAP_AP | 0.0069 | 0.0791299 | 0.0004998 | 346 | 4 |

*NUMBERS ARE SMALL IN AFFECTED (GROUP 2), (G2), AND COMPARISON MAY THEREFORE BE UNRELIABLE.

CONTUSION

| FEATURE | P-VALUE (WILCOXON) | T-VALUE | P-VALUE (PERM-PCLT) | P-VALUE (PERM-EXACT.MC) | N (G1) | N (G2) |
|---|---|---|---|---|---|---|
| NRGN | 0.4208 | 0.7749435 | 0.6137164 | 0.7801099 | 380 | 27 |
| BDNF | 0.4131 | 0.9468474 | 0.5317376 | 0.9390305 | 385 | 27 |
| GFAP | 0.0040 | 0.0038985 | 0.9929423 | 0.0139930 | 380 | 27 |
| NSE | 0.0051 | 0.0102329 | 0.9967416 | 0.0049975 | 385 | 27 |
| SNCB | 0.8375 | 0.7435593 | 0.3681834 | 0.7601199 | 328 | 23 |
| ALDOC | 0.0225 | 0.0372630 | 0.0126932 | 0.0274863 | 70 | 6 |
| SNCB_MSD | 0.1422 | 0.2675958 | 0.8787674 | 0.2598701 | 41 | 11 |
| GFAP_AP | 0.0000 | 0.0000058 | 1.0000000 | 0.0004998 | 346 | 26 |

FIG. 12B
CONTINUED

SEQUENCE LISTING

```
<160> NUMBER OF SEQ ID NOS: 1

<210> SEQ ID NO 1
<211> LENGTH: 440
<212> TYPE: PRT
<213> ORGANISM: Human

<400> SEQUENCE: 1

Met Glu Tyr Gln Ile Leu Lys Met Ser Leu Cys Leu Phe Ile Leu Leu
1               5                   10                  15

Phe Leu Thr Pro Gly Ile Leu Cys Ile Cys Pro Leu Gln Cys Ile Cys
            20                  25                  30

Thr Glu Arg His Arg His Val Asp Cys Ser Gly Arg Asn Leu Ser Thr
        35                  40                  45

Leu Pro Ser Gly Leu Gln Glu Asn Ile Ile His Leu Asn Leu Ser Tyr
    50                  55                  60

Asn His Phe Thr Asp Leu His Asn Gln Leu Thr Gln Tyr Thr Asn Leu
65                  70                  75                  80

Arg Thr Leu Asp Ile Ser Asn Asn Arg Leu Glu Ser Leu Pro Ala His
                85                  90                  95

Leu Pro Arg Ser Leu Trp Asn Met Ser Ala Ala Asn Asn Asn Ile Lys
            100                 105                 110

Leu Leu Asp Lys Ser Asp Thr Ala Tyr Gln Trp Asn Leu Lys Tyr Leu
        115                 120                 125

Asp Val Ser Lys Asn Met Leu Glu Lys Val Val Leu Ile Lys Asn Thr
    130                 135                 140

Leu Arg Ser Leu Glu Val Leu Asn Leu Ser Ser Asn Lys Leu Trp Thr
145                 150                 155                 160

Val Pro Thr Asn Met Pro Ser Lys Leu His Ile Val Asp Leu Ser Asn
                165                 170                 175

Asn Ser Leu Thr Gln Ile Leu Pro Gly Thr Leu Ile Asn Leu Thr Asn
            180                 185                 190

Leu Thr His Leu Tyr Leu His Asn Asn Lys Phe Thr Phe Ile Pro Asp
        195                 200                 205

Gln Ser Phe Asp Gln Leu Phe Gln Leu Gln Glu Ile Thr Leu Tyr Asn
    210                 215                 220

Asn Arg Trp Ser Cys Asp His Lys Gln Asn Ile Thr Tyr Leu Leu Lys
225                 230                 235                 240
```

-continued

```
Trp Met Met Glu Thr Lys Ala His Val Ile Gly Thr Pro Cys Ser Thr
                245                 250                 255

Gln Ile Ser Ser Leu Lys Glu His Asn Met Tyr Pro Thr Pro Ser Gly
            260                 265                 270

Phe Thr Ser Ser Leu Phe Thr Val Ser Gly Met Gln Thr Val Asp Thr
            275                 280                 285

Ile Asn Ser Leu Ser Val Val Thr Gln Pro Lys Val Thr Lys Ile Pro
        290                 295                 300

Lys Gln Tyr Arg Thr Lys Glu Thr Thr Phe Gly Ala Thr Leu Ser Lys
305                 310                 315                 320

Asp Thr Thr Phe Thr Ser Thr Asp Lys Ala Phe Val Pro Tyr Pro Glu
                325                 330                 335

Asp Thr Ser Thr Glu Thr Ile Asn Ser His Glu Ala Ala Ala Ala Thr
            340                 345                 350

Leu Thr Ile His Leu Gln Asp Gly Met Val Thr Asn Thr Ser Leu Thr
            355                 360                 365

Ser Ser Thr Lys Ser Ser Pro Thr Pro Met Thr Leu Ser Ile Thr Ser
    370                 375                 380

Gly Met Pro Asn Asn Phe Ser Glu Met Pro Gln Gln Ser Thr Thr Leu
385                 390                 395                 400

Asn Leu Trp Arg Glu Glu Thr Thr Thr Asn Val Lys Thr Pro Leu Pro
                405                 410                 415

Ser Val Ala Asn Ala Trp Lys Val Asn Ala Ser Phe Leu Leu Leu Leu
                420                 425                 430

Asn Val Val Val Met Leu Ala Val
            435                 440
```

BIOMARKER LEVELS AND NEUROIMAGING FOR DETECTING, MONITORING AND TREATING BRAIN INJURY OR TRAUMA

PRIORITY

This application claims priority from U.S. Provisional Application No. 62/510,096, filed on May 23, 2017, and U.S. Provisional Application No. 62/532,180, filed on Jul. 13, 2017, the disclosures of which are incorporated by reference herein in their entireties.

FIELD OF THE INVENTION

The invention generally relates to the field of brain injuries or trauma. More specifically, the invention provides methods and compositions useful in the detection, diagnosis, prognosis, assessment, monitoring and/or treatment of brain injuries or trauma.

BACKGROUND OF THE INVENTION

Head injury brings nearly 5 million patients into emergency departments per year in the United States. The majority of patients receiving a CT scan, i.e., 90%, are CT negative, but may have a traumatic brain injury (TBI). TBI is caused by a head injury that can result in lasting damage to the brain and affects up to 10 million patients worldwide each year. The health effects of TBI can be debilitating, result in long term disability, and have significant financial burdens. As a result, TBI is an expanding global health concern.

TBI is graded as mild (mild TBI or "mTBI") meaning a brief change in mental status or consciousness), moderate, or severe (meaning an extended period of unconsciousness or amnesia after the injury) on the basis of the level of consciousness or Glasgow coma scale (GCS) score after resuscitation. The GCS scores eye opening (spontaneous=4, to speech=3, to pain=3, none=1), motor response (obeys=6, localizes=5, withdraws=4, abnormal flexion=3, extensor response=2, none=1), and verbal response (oriented=5, confused=4, inappropriate=3, incomprehensible=2, none=1). Mild TBI (GCS 13-15) is in most cases a concussion and there is full neurological recovery, although many of these patients have short-term memory and concentration difficulties. In moderate TBI (GCS 9-13) the patient is lethargic or stuporous, and in severe injury (GCS 3-8) the patient is comatose, unable to open his or her eyes or follow commands.

Patients with severe TBI (comatose) have a significant risk of hypotension, hypoxemia, and brain swelling. If these sequelae are not prevented or treated properly, they can exacerbate brain damage and increase the risk of death.

The term "traumatic intracerebral hemorrhage" refers to such bleeding that is caused, caused by, or associated with traumatic injury. Intracerebral hemorrhages commonly occur in the basal ganglia, thalamus, brain stem (predominantly the pons), cerebral hemispheres, and the cerebellum. Extension into the ventricles occurs in association with deep, large hematomas. Edematous parenchyma, often discolored by degradation products of hemoglobin, is visible adjacent to the clot. Histologic sections are characterized by the presence of edema, neuronal damage, macrophages, and neutrophils in the region surrounding the hematoma. The hemorrhage spreads between planes of white-matter cleavage, causing some destruction of the brain structure, and leaving intact neural tissue within and surrounding the hematoma.

Intraparenchymal bleeding results from the rupture of the small penetrating arterioles that originate from basilar arteries or from the anterior, middle, or posterior cerebral arteries. Degenerative changes in the arteriolar walls by chronic hypertension reduce compliance, weaken the wall, and increase the likelihood of spontaneous rupture. Studies suggest that most bleeding occurs at or near the bifurcation of affected arteries, where prominent degeneration of the tunica media and smooth muscles can be seen.

Neurological damage after TBI does not all occur immediately at the moment of impact (primary injury), but instead evolves afterwards (secondary injury) and can become chronic. Secondary brain injury is the leading cause of in-hospital deaths after TBI. Most secondary brain injury is caused by brain swelling, with an increase in intracranial pressure and a subsequent decrease in cerebral perfusion leading to ischemia. Within hours of TBI, due to a breakdown of tight endothelial junctions which make up the blood-brain barrier (BBB), normally excluded intravascular proteins and fluid penetrate into the cerebral parenchymal extracellular space (vasogenic edema). Once plasma constituents cross the BBB, the edema spreads. The vasogenic fluid accumulating in brain causes cerebral edema, raises intracranial pressure, and lowers the threshold of systemic blood pressure for cerebral ischemia. A reduction in cerebral blood flow or oxygenation below a threshold value or increased intracranial pressure leading to cerebral herniation increases brain damage and morbidity.

Approximately 10% of TBIs (1,400,000 annual U.S. cases) are complicated by intracerebral hemorrhage requiring surgery. The delay in the breakdown of the blood-brain barrier and the development of cerebral edema after an intracerebral hemorrhage (ICH) suggest that there may be secondary mediators of both neural injury and edema. It is generally believed that blood and plasma products mediate most secondary processes that are initiated after an ICH.

Assessing injury severity and determining the risk for lasting symptoms among mTBI subjects pose challenges for medical and clinical practice, sports events and military care. Commonly used diagnostic evaluation and monitoring of patients with head injury remain imprecise and subjective, and would greatly benefit from robust blood-based biomarkers for objective real-time testing. In addition, clinical tools such as physical exam, central nervous system (CNS) imaging using computerized tomography (CT) scan or magnetic resonance imaging (MRI)), used alone, are subjective, not widely available, not sensitive or specific enough, and too costly to identify all patients with brain and/or CNS injury, and therefore have a high false negative rate.

A need therefore exists for methods to identify and assess injury severity in individuals (patients) having head and/or brain injury, such as, for example, mTBI or concussion, and to determine their risk for lasting symptoms and for returning to normal activity (work or play) following injury. In addition, methods are needed for determining and assessing those individuals having head injury who are at high risk of developing more severe brain trauma or injury so that they can receive the appropriate treatment, e.g., surgery or other medical intervention, perhaps on an urgent basis, more conservative medical management, or safely discharged. Patients having head injury would also benefit from novel biomarkers that detect mild TBI and concussion with early post-injury blood elevation for point-of care detection.

SUMMARY OF THE INVENTION

The invention satisfies one or more of the foregoing needs in the art and generally provides methods and compositions for detecting, diagnosing, prognosing, assessing, monitoring and/or treating head or brain injury involving changes or alterations in blood-brain barrier (BBB) permeability (e.g., vascular permeability) and correlative alterations (e.g., increases or decreases) in the levels of certain circulating brain biomarker proteins in an individual who has, or is suspected of having, sustained a head or brain injury. In particular, changes in BBB permeability may include leakiness or damage to the integrity of the BBB vasculature, resulting in the presence of blood or hemorrhage (e.g., mild or severe) in one or more areas of the brain. The methods further allow for determining if an individual has suffered a more severe or lasting head or brain injury or trauma and/or whether an individual has suffered damage to specific white matter areas or tracts (e.g., fiber tracts) in the brain, such as cingulum cingulate tracts, cingulum hippocampal tracts, the inferior fronto-occipital fasciculae (IFOF), the inferior and superior lateral fascicule (ILF and SLF, respectively), the corpus callosum forceps major, and other tracts in order to provide appropriate and effective treatment to the individual. In addition, the described methods inform a medical practitioner's decisions regarding the extent and/or status of a subject's brain injury or trauma and allow the medical practitioner to determine whether (or when) the subject can return to normal or regular activity (e.g., work or play). In an embodiment, changed or altered blood-brain barrier permeability signals in brain areas is determined by neuroimaging analysis, e.g., MRI or MRI with contrast, or Dynamic Contrast Enhanced MRI (DCE-MRI). In embodiments, the head or brain injury involves traumatic brain injury (TBI). In a particular embodiment, the TBI is mild TBI (mTBI) or concussion, which accounts for approximately 70-90% of all cases of TBI.

In aspects of the invention, the methods, compositions, and kits described herein can be used in screening and identifying severity of head or brain injury in patients, e.g., patients who have TBI, patients who are concussed and/or who have mTBI, and/or patients who suffer from bleeding or vascular or BBB leakiness in one or more areas of the brain and/or identifying specific white matter areas or tracts (e.g., fiber tracts) in the brain that have been damaged, such as the cingulum cingulate tracts, cingulum hippocampal tracts, the inferior fronto-occipital fasciculae (IFOF), the inferior and superior lateral fascicule (ILF and SLF, respectively), the corpus callosum forceps major, and other tracts. In an embodiment, damage to the white matter areas or tracts in the brain is determined using Diffusion Tensor Imaging (DTI-MRI).

In one aspect, the invention provides a method of qualifying brain injury status in an individual as having, as at risk of having or as having had a mild traumatic brain injury (mTBI) or a concussion, the method including: measuring levels of one or more biomarkers associated with brain injury, selected from Brain Derived Neurotrophic Factor (BDNF), Glial Fibrillary Acidic Protein (GFAP), Neurogranin (NRGN), Neuron Specific Enolase (NSE), Oligodendrocyte Myelin Glycoprotein (OMG), or Synuclein Beta (SNCB), in a biological sample obtained from an individual who has sustained or who is suspected of having sustained a brain injury relative to control levels; neuroimaging blood brain barrier (BBB) permeability signals to detect changes in vascular permeability in the brain of the individual relative to a healthy individual; and c. qualifying the brain injury status of the individual as having mTBI or concussion, or as having had mTBI or a prior concussion if the individual has an altered level of the one or more biomarkers relative to control levels and if the neuroimaging of BBB permeability signals demonstrates a change in vascular permeability in the brain of the individual. In an embodiment, elevated levels of the biomarkers NSE and OMG relative to control levels, and a change in vascular permeability determined by neuroimaging BBB permeability signals in the brain of the individual, qualify the brain injury status of the individual as having mTBI or a concussion, or as having had mTBI or a prior concussion. In another embodiment, decreased levels of the biomarkers BDNF and SNCB relative to control levels, and a change in BBB permeability signals determined by neuroimaging the brain of the individual, qualify the brain status of the individual as having mTBI or as having had mTBI. In some embodiments, the levels of one or more of the biomarkers are increased relative to control levels. In other embodiments, the levels of one or more of the biomarkers are decreased relative to control levels.

In another aspect, the invention provides a method of treating mild traumatic brain injury (mTBI) or concussion in a subject, the method including: (a) measuring the level of OMG biomarker in a biological sample obtained from the subject relative to a control level; (b) neuroimaging blood brain barrier (BBB) permeability signals in the brain of the subject to detect changes in vascular permeability in a BBB area relative to a healthy individual; and (c) treating the subject, or recommending that the subject be treated, for mTBI or concussion if the level of the OMG biomarker is increased relative to the control level and if changes in vascular permeability in a BBB area is detected. In an embodiment, the levels of one or more protein biomarkers selected from the group consisting of Brain Derived Neurotrophic Factor (BDNF), Neurogranin (NRGN), Neuron Specific Enolase (NSE), and Synuclein Beta (SNCB) relative to control levels are also measured.

In another aspect, the invention provides a method of detecting mTBI or concussion in a subject, the method including the steps of (a) contacting a biological sample from the subject with an antibody or an antigen binding fragment thereof that specifically binds OMG protein biomarker and with an antibody or an antigen binding fragment thereof that specifically binds one or more biomarkers selected from the group consisting of Brain Derived Neurotrophic Factor (BDNF), Intracellular Adhesion Molecule 5 (ICAM5), Metallothionein 3 (MT3), Neurogranin (NRGN), Glial Fibrillary Acidic Protein (GFAP), Synuclein Beta (SNCB) and Neuron Specific Enolase (NSE); (b) assaying binding of the antibody or an antigen binding fragment thereof to the biomarkers in the sample; and (c) neuroimaging blood brain barrier (BBB) permeability signals in the brain of the subject to detect a change in vascular permeability in a BBB area; and (d) detecting mTBI or concussion in the subject if the biomarker levels are increased or decreased in the sample relative to a control level and if a change in vascular permeability in the BBB is detected. In some embodiments, the levels of one or more of the biomarkers are increased relative to control levels. In other embodiments, the levels of one or more of the biomarkers are decreased relative to control levels. In some embodiments, the assaying of binding by the antibody or an antigen binding fragment thereof is carried out by an immunoassay, an immunoblotting method, an immunoprecipitation assay, an immunostaining method, a quantitative assay, an immunofluorescent assay, or a chemiluminescence assay. In an embodiment, an increase in the level of the OMG or GFAP biomarkers relative to control and the detection of BBB permeability in the subject indicates mTBI in the subject. In another embodiment, an increase in the levels of the GFAP, OMG and NSE biomarkers relative to control levels and the detection of BBB permeability in the subject indicates mTBI in the subject. In yet another embodiment, decrease in the levels of the BDNF and SNCB biomarkers relative to control levels and the detection of BBB permeability in the subject indicates mTBI in the subject.

According to another aspect, the invention provides a method of ascertaining whether a patient who has sustained mTBI or concussion can return to work or play, the method including: (a) measuring the level of one or more biomarkers selected from the group consisting of BDNF, ICAM5, MT3, NRGN, OMG, NSE, SNCB or GFAP in a sample obtained from the patient relative to a reference level at first time point; (b) measuring the level of one or more biomarkers selected from the group consisting of BDNF, ICAM5, MT3, NRGN, OMG, NSE, SNCB or GFAP in a sample obtained from the patient at second time point subsequent to the first time point; (c) neuroimaging blood brain barrier (BBB) permeability signals in the brain of the subject to detect a change in vascular permeability in a BBB area at the first time point; (d) neuroimaging blood brain barrier (BBB) permeability signals in the brain of the subject to detect a change in vascular permeability in a BBB area at the second time point; and (e) ascertaining that the patient can return to work or play if the biomarker levels measured at the second time point are decreased or trending to normal levels versus the levels of these biomarkers measured at the first time point and if any change in vascular permeability in the BBB area is resolved at the second time point. In some embodiment, the reference level is the level of the one or more biomarkers present in a normal subject who does not have mTBI or concussion. In some embodiments, decreased levels of one or more of the biomarkers or no increase in said levels indicates that said subject can return to play or work. In certain embodiments, the steps (a)-(b) are repeated at one or more predetermined intervals to monitor the levels of the one or more biomarkers in the subject. In certain embodiments, neuroimaging analysis is performed in BBB areas of the brain of the subject to detect a change in vascular permeability in a BBB area of the brain at one or more predetermined times following the second time point to detect unresolved vascular damage in the BBB areas or to assess whether the subject is at risk for more severe or secondary vascular damage. In some embodiments, the more severe or secondary vascular damage is selected from major hemorrhage, edema, blood vessel leakage, or aneurysm.

In another aspect, the invention provides a method of detecting whether a subject who has or who is suspected of having a brain injury has parenchymal involvement such as subarachnoid hemorrhage or contusion, the method including: contacting a biological sample obtained from the subject with antibodies or antigen binding fragments thereof that specifically bind to Glial Fibrillary Acidic Protein (GFAP) and to Neuron Specific Enolase (NSE) biomarker proteins in a sample obtained from the subject; measuring the levels of the GFAP and NSE biomarker proteins in the subject's sample compared with control levels in an antibody binding assay; neuroimaging the subject by CT scan predicated on measuring increased levels of GFAP and NSE in the subject's sample compared to control levels; and detecting subarachnoid hemorrhage and/or contusion in the subject by CT scan, thus indicating that the subject has a serious brain injury.

In any of the above embodiments, neuroimaging is further performed on the subject to detect damage or alterations in white matter areas or fiber tracts of the brain as described herein. For example, the white matter areas or tracts in the brain include one or more of cingulum cingulate tracts, cingulum hippocampal tracts, the inferior fronto-occipital fasciculae (IFOF), the inferior lateral fascicule (ILF), the superior lateral fascicule (SLF), or the corpus callosum forceps major.

In another of its aspects, a method of qualifying brain injury severity in a subject is provided, in which the method involves contacting a biological sample from the subject with an antibody that specifically binds one or more brain specific biomarker proteins selected from Neurogranin (NRGN), Synuclein Beta (SNCB), Neuron Specific Enolase (NSE), Glial Fibrillary Acidic Protein (GFAP), Brain Derived Neurotrophic Factor (BDNF), or Oligodendrocyte Myelin Glycoprotein (OMG), in an antibody binding assay; neuroimaging the subject to visualize fiber tracts in the brain when the levels of one or more of the biomarker proteins in the subject's sample are changed compared with control levels based on the antibody binding assay; and detecting a change in one or more fiber tracts in the brain correlated with the changes in the levels of the one or more biomarker proteins, thereby qualifying the subject as having a serious brain injury. In an embodiment of the method, the levels of one or more of the NRGN, SNCB or NSE biomarkers are increased relative to control levels and changes are detected in one or more long fiber tracts in the brain. In an embodiment of the method, the levels of the BDNF biomarker are increased relative to control levels and changes are detected in one or more long fiber tracts in the brain. In an embodiment of the method, changes are detected in one or more long fiber tracts in the brain selected from the inferior fronto: occipital fasciculus (IFOF) tract, the inferior lateral fasciculus (ILF) tract, the cingulum cingulate tract and the hippocampal tract. In an embodiment, the neuroimaging is MRI, more specifically, contrast MRI, or Dynamic Contrast Enhanced MRI (DCE-MRI). In an embodiment of the method, the subject suffers from repetitive sub-concussive injury as indicated by determining damage to specific fiber tracts in the brain. In an embodiment of the method, detecting the changes to the fiber tracts in the brain correlated with the changes in the levels of the one or more biomarker proteins indicates that the subject should not return to work or play. In an embodiment, the sample is selected from one or more of blood, serum, plasma, or cerebrospinal fluid (CSF). In some embodiments, antibody binding is measured in an immunoassay, an immunoblotting method, an immunoprecipitation assay, an immunostaining method, a quantitative assay, an immunofluorescent assay, or a chemiluminescence assay. Preferably the immunoassay is an enzyme linked immunosorbent assay (ELISA), a fluorescence-linked immunosorbent assay (FLISA), or a mesoscale discovery electro-chemiluminescence ELISA (MSD-ELISA).

In other aspect, the invention provides a method in which changes in blood brain barrier (BBB) permeability associated with mTBI or concussion can be determined, identified, detected, or diagnosed in a subject in need thereof by detecting levels of one or more brain-specific protein biomarkers, in particular, the glycolytic enzyme Aldolase C (ALDOC) and/or Glial Fibrillary Acidic Protein (GFAP), in a biological sample obtained from a subject relative to control levels, and neuroimaging the brain of the subject to determine BBB permeability changes in the brain and/or the extent thereof. In an embodiment, the method further includes detecting levels and changes thereof (e.g., increase or decrease) of one or more other brain-specific protein biomarkers selected from Brain Derived Neurotrophic Factor (BDNF), Neurogranin (NRGN), Neuron Specific Enolase (NSE), Oligodendrocyte Myelin Glycoprotein (OMG) and Synuclein Beta (SNCB). In an embodiment, an increased or elevated level of one or both of ALDOC and/or GFAP relative to control level correlates with changes in BBB permeability, e.g., damage to the integrity of the BBB, or vascular leakiness, as detected in the subject by neuroimaging analysis. In an embodiment, the method provides for the detection of more subtle types of vascular damage in the brain of the subject, such as areas of minor hemorrhage, as well as allows for the assessment of whether the subject is at risk for more severe or secondary vascular damage, such as a major hemorrhage or aneurysm, particularly at a time subsequent to the initial head or brain injury or trauma.

In other aspects of the invention, methods are provided in which a head or brain injury, such as mTBI or concussion, can be determined, identified, detected, or diagnosed in a subject by detecting one or more brain-specific protein biomarkers in conjunction with detection of changes in vascular permeability, e.g., an abnormal increase in BBB permeability signals in areas of the brain, in the subject by neuroimaging analysis, e.g., MRI or CT scan. In an embodiment, damage to the integrity of the BBB is assessed by MRI, and in particular, MRI with gadolinium contrast, or 3T MRI. In an embodiment, changes in levels of one or more protein biomarkers are detected in conjunction with changes in BBB permeability signals, in which the biomarkers include Aldolase C (ALDOC), Brain Derived Neurotrophic Factor (BDNF), Glial Fibrillary Acidic Protein (GFAP), Neurogranin (NRGN), Neuron Specific Enolase (NSE), Oligodendrocyte Myelin Glycoprotein (OMG) and Synuclein Beta (SNCB). In an embodiment, an increased level of the protein biomarker ALDOC relative to control is detected in conjunction with changes in BBB permeability signals that show leakage or breakdown. In an embodiment, an increased level of the protein biomarker ALDOC or in the protein biomarker GFAP relative to control is detected in conjunction with changes in BBB permeability signals. In another embodiment, increased levels of a panel of biomarkers including ALDOC, GFAP and/or OMG relative to control are detected in conjunction with changes in BBB permeability signals. In another embodiment, increased levels of a panel of biomarkers including ALDOC, GFAP and NSE relative to control are detected in conjunction with changes in BBB permeability signals.

In an aspect, the invention provides a method for diagnosing or identifying mild traumatic brain injury (mTBI) or concussion in a subject, in which the method includes: (a) contacting a biological sample from the subject with antibodies that specifically bind Aldolase C (ALDOC) or Glial Fibrillary Acidic Protein (GFAP) using an immunoassay; (b) neuroimaging the brain of the subject by MRI (e.g., MRI with contrast or Dynamic Contrast Enhanced (DCE) MRI) to detect changes in BBB permeability signals in conjunction with the increased or elevated biomarker levels; and (c) diagnosing or identifying mTBI or concussion in the subject by detecting an increase or elevation in the level of ALDOC or GFAP in the subject's sample relative to a control level. In an embodiment, mTBI or concussion in the subject is associated with temporary astroglial cell wounding. In an embodiment, the biological sample is blood or serum. In an embodiment, the control is a healthy or normal individual not having mTBI or concussion. In an embodiment, the subject is an athlete who plays a contact sport, e.g. a football player. In an embodiment, the levels of one or more biomarkers including Brain Derived Neurotrophic Factor (BDNF), Neurogranin (NRGN), Neuron Specific Enolase (NSE), Oligodendrocyte Myelin Glycoprotein (OMG) and Synuclein Beta (SNCB) are also measured relative to control levels. In an embodiment, neuroimaging (e.g., DTI-MRI) is further performed on the subject to detect damage or alterations in white matter areas or fiber tracts of the brain as described herein.

In another of its aspects, the invention provides a method of detecting or identifying brain injury or trauma, in particular, mTBI or concussion, associated with a change or alteration in BBB permeability signals in a subject, in which the method includes the steps of (a) contacting a biological sample from the subject with antibodies that bind at least one panel of biomarkers using an immunoassay, wherein the panel of biomarkers includes one of the following biomarker panels: ALDOC and OMG; ALDOC, NRGN and OMG; ALDOC, BDNF and NSE; BDNF and SNCB; or ALDOC, NRGN and BDNF; or GFAP, NRGN and BDNF; (b) neuroimaging the brain of the subject by MRI with contrast; and (c) detecting or identifying the subject as having brain injury or trauma, in particular, mTBI or concussion, by determining the levels of the biomarkers in the biomarker panels relative to control levels and determining whether the subject has a change or alteration in BBB permeability signals to detect changes indicative of leakage or breakdown. In an embodiment, the method involves correlating a detected level of the panel of biomarkers to predefined levels of the same biomarkers that correlate to a patient having mTBI or identifying the patient as not having mTBI by correlating a detected level of the panel of biomarkers to predefined levels of the same biomarkers that correlate to a patient not having mTBI. In an embodiment, the biomarkers include one of the following biomarker panels: GFAP and OMG; GFAP, NRGN and OMG; GFAP, BDNF and NSE; or GFAP, NRGN and BDNF. In a specific embodiment, the panel of biomarkers includes ALDOC and OMG or GFAP and OMG. In another embodiment, the panel of biomarkers includes ALDOC, NRGN and OMG or GFAP, NRGN and OMG. In another embodiment, the panel of biomarkers includes ALDOC, BDNF and NSE or GFAP, BDNF and NSE. The panel of biomarkers can also comprise GFAP, NRGN and BDNF. In an embodiment, a panel of biomarkers useful in the invention includes ALDOC or GFAP and one or more of BDNF, NRGN, NSE, OMG and SNCB. In an embodiment a panel of biomarkers useful in the invention includes OMG or GFAP and one or more of BDNF, NRGN, NSE, and SNCB.

In certain embodiments of the above aspects, the contacting step includes the use of one or more antibodies or an antigen binding fragment thereof that specifically bind at least one biomarker selected from the group consisting of ALDOC, GFAP, BDNF, NRGN, NSE, OMG and SNCB.

In certain embodiments of the above aspects, a change in the levels of one or more biomarkers, such as ALDOC and/or GFAP; or ALDOC or GFAP and one or more of BDNF, NRGN, NSE, OMG or SNCB, to a decreased level or normal level provides an indication of repair of or recovery from brain injury, and indicates returning to work or returning to play is appropriate. In an embodiment, the subject is further assessed by neuroimaging analysis of the head/brain using MRI, e.g., MRI with contrast or 3T MRI, or CT scan, to determine recovery or repair of a change or alteration to the BBB permeability in the subject; recovery or repair (e.g., no vascular leakiness; no abnormal blood or hemorrhage) allows further confirmation of returning to work or play.

In certain embodiments, comparison of the amount of detected biomarker to a control is conducted by using at least one classifier algorithm. In some embodiments, said at least one classifier algorithm is selected from the group consisting of a decision tree classifier, logistic regression classifier, nearest neighbor classifier, neural network classifier, Gaussian mixture model (GMM), Support Vector Machine (SVM) classifier, nearest centroid classifier, linear regression classifier, linear discriminant analysis (LDA) classifier, quadratic discriminant analysis (QDA) classifier, LogitBoost classifier, rotation forest classifier, and random forest classifier.

In a particular embodiment, the invention includes a microarray chip. More specifically, the chip may include a small wafer that carries a collection of binding agents bound to its surface in an orderly pattern, each binding agent occupying a specific position on the chip. The set of binding agents specifically bind to each of the one or more one or more of the biomarkers described herein. In particular embodiments, a few micro-liters of blood serum or plasma are dropped on the chip array. Biomarker proteins present in the tested specimen bind to the binding agents specifically recognized by them. Subtype and amount of bound mark is detected and quantified using, for example, a fluorescently-labeled secondary, subtype-specific antibody. In particular embodiments, an optical reader is used for bound biomarker detection and quantification. Thus, a system can include a chip array and an optical reader. In other embodiments, a chip is provided.

In another of its aspects, the invention provides a method of identifying or diagnosing mild traumatic head injury (mTBI) or concussion in a subject, in which the method includes: a. measuring the levels of Aldolase C (ALDOC) and/or Glial Fibrillary Acidic Protein (GFAP) biomarkers, and the level of one or more protein biomarkers selected from Brain Derived Neurotrophic Factor (BDNF), Neurogranin (NRGN), Neuron Specific Enolase (NSE), Oligodendrocyte Myelin Glycoprotein (OMG), or Synuclein Beta (SNCB) in a biological sample obtained from the subject relative to a control level; and b. identifying or diagnosing the subject as having mTBI or concussion if the measured levels the biomarkers are increased or decreased in the subject's sample relative to the control levels. In an embodiment, the control level is the level of the biomarker present in a normal subject not having mTBI or concussion. In an embodiment of the method, the protein biomarker level is measured by an immunoassay, an immunoblotting method, an immunoprecipitation assay, an immunostaining method, a quantitative assay, an immunofluorescent assay, or a chemiluminescence assay. In an embodiment, the protein biomarker level is measured by an immunoassay, for example, an enzyme linked immunosorbent assay (ELISA) using an antibody or an antigen binding fragment thereof that specifically binds the protein biomarker. In a particular embodiment, the immunoassay is an enzyme linked immunosorbent assay (ELISA) using an antibody or an antigen binding fragment thereof that specifically binds one or more of the biomarker proteins. In an embodiment, the ELISA is a mesoscale discovery electro-chemiluminescence assay (MSD-ELISA). In an embodiment, the method further includes neuroimaging of blood brain barrier (BBB) permeability signals in the brain of the subject to detect changes in vascular permeability and confirming mTBI or concussion if increased BBB permeability is detected. In an embodiment, the neuroimaging is performed using MRI, such as MRI with contrast and/or 3T MRI. In another embodiment, the neuroimaging is performed using CT imaging/scanning. In an embodiment, if the subject is identified or diagnosed as having an elevated or increased level of the ALDOC or GFAP protein biomarkers, one or both of the ALDOC or GFAP biomarker levels is further measured in a biological sample of the subject relative to a control level during the on-season and in the off-season of the athlete to monitor mTBI or concussion symptoms in the subject, wherein elevated levels of one or both of the biomarkers at the time of measurement indicates mTBI or concussion in the athlete. In an embodiment, the method includes neuroimaging of blood brain barrier (BBB) permeability signals in the brain of the subject to monitor BBB permeability and sustained vascular damage or resolution thereof in the athlete.

In another of its aspects, the invention provides a method of determining whether a subject requires treatment for mild traumatic brain injury (mTBI) or concussion, in which the method includes: (a) measuring the levels of one or both of Aldolase C (ALDOC) or Glial Fibrillary Acidic Protein (GFAP) protein biomarkers and the levels of one or more protein biomarkers selected from Brain Derived Neurotrophic Factor (BDNF), Neurogranin (NRGN), Neuron Specific Enolase (NSE), Oligodendrocyte Myelin Glycoprotein (OMG), or Synuclein Beta (SNCB) in a biological sample obtained from the subject relative to a reference level; and (b) treating the subject, or recommending that the subject should be treated, for mTBI or concussion if, for example, the level of the ALDOC or GFAP biomarker is increased or elevated in the subject's sample relative to the reference level and/or if the levels of one or more of the other biomarkers are increased or decreased relative to control levels. In an embodiment, the level of the one or more protein biomarkers is measured by an immunoassay, an immunoblotting method, an immunoprecipitation assay, an immunostaining method, a quantitative assay, an immunofluorescent assay, or a chemiluminescence assay. In an embodiment, the level of the one or more protein biomarkers is measured by an immunoassay, which is, by way of nonlimiting example, an enzyme linked immunosorbent assay (ELISA) or a mesoscale discovery electro-chemiluminescence ELISA (MSD-ELISA). In an embodiment, the method further includes assessing the subject's brain by neuroimaging to detect changes in vascular permeability in the brain BBB as further indicating mTBI or concussion.

In another of its aspects, the invention provides a method of qualifying brain injury status in an individual having or at risk of having mild traumatic brain injury (mTBI) or concussion, in which the method includes: (a) measuring levels of one or more biomarkers associated with brain injury in a biological sample obtained from an individual who has sustained or who is suspected of having sustained a brain injury relative to control levels; (b) neuroimaging blood brain barrier (BBB) permeability signals to detect changes in the brain of the individual; and (c) qualifying the brain injury status of the individual as having mTBI or concussion, if the individual has an altered (e.g., increased or decreased) level of the one or more biomarkers relative to control levels and if areas of the neuroimaging of BBB permeability signals demonstrates a change in vascular permeability in the brain of the individual. In an embodiment, the one or more biomarkers is selected from Aldolase C (ALDOC), Brain Derived Neurotrophic Factor (BDNF), Glial Fibrillary Acidic Protein (GFAP), Neurogranin (NRGN), Neuron Specific Enolase (NSE), Oligodendrocyte Myelin Glycoprotein (OMG), or Synuclein Beta (SNCB) to identify an altered level relative to control level. In a particular embodiment, the one or more biomarkers is ALDOC and OMG; ALDOC, NRGN and OMG; ALDOC, BDNF and NSE; BDNF and SNCB; ALDOC, NRGN and BDNF; GFAP and OMG; GFAP, NRGN and OMG; GFAP, BDNF and NSE; or GFAP, NRGN and BDNF. In an embodiment, elevated or increased levels of the biomarkers ALDOC, GFAP and OMG (or one or more additional biomarkers) relative to control levels, and a change in vascular permeability determined by neuroimaging the brain of the individual, qualify the brain injury status of the individual as having mTBI or a concussion, or as having had a prior concussion. In an embodiment, elevated levels of the biomarkers ALDOC, GFAP and NSE relative to control levels, and BBB permeability determined by neuroimaging the brain of the individual, qualify the brain status of the individual as having mTBI or as having had mTBI. In an embodiment, decreased levels of the biomarkers BDNF and SNCB relative to control levels, and a change in vascular permeability determined by neuroimaging the brain of the individual, qualify the brain status of the individual as having mTBI or as having had mTBI.

In another aspect, the invention provides a method of treating mild traumatic brain injury (mTBI) or concussion in a subject, in which the method includes: (a) measuring the level of Aldolase C (ALDOC) biomarker in a biological sample obtained from the subject relative to a control level; (b) neuroimaging blood brain barrier (BBB) permeability signals in the brain of the subject to detect changes in vascular permeability in a BBB area; and (c) treating the subject, or recommending that the subject be treated, for mTBI or concussion if the level of the ALDOC biomarker is increased relative to the control level and if BBB permeability is detected. In an embodiment, the neuroimaging assessment is performed using MRI, such as contrast MRI (DCE-MRI) or 3T MRI.

In another aspect, the invention provides a method of identifying whether a subject has sustained mTBI or concussive brain injury, in which the method includes the steps of (a) contacting a biological sample from the subject with an antibody or an antigen binding fragment thereof that specifically binds ALDOC and/or with an antibody or an antigen binding fragment thereof that specifically binds GFAP; (b) measuring the levels of ALDOC and/or GFAP in the sample relative to a reference level based on the binding of the antibody or an antigen binding fragment thereof to ALDOC and to GFAP in the sample; (c) neuroimaging blood brain barrier (BBB) permeability signals in the brain of the subject to detect a change in vascular permeability in a BBB area; and (d) identifying that the subject has sustained mTBI or concussive brain injury if the ALDOC and/or GFAP levels are altered relative to the reference level and if a change in vascular permeability in the BBB is detected. In an embodiment, the levels of ALDOC and/or GFAP are increased or elevated relative to reference levels. In an embodiment, the method further includes contacting the biological sample with one or more antibodies or an antigen binding fragment thereof that specifically binds one or more protein biomarkers selected from the group consisting of Brain Derived Neurotrophic Factor (BDNF), Neurogranin (NRGN), Neuron Specific Enolase (NSE), Oligodendrocyte Myelin Glycoprotein (OMG) and Synuclein Beta (SNCB).

In another aspect, the invention provides a method of detecting mTBI or concussion in a subject, in which the method includes the steps of: (a) contacting a biological sample from the subject with an antibody or an antigen binding fragment thereof that specifically binds ALDOC protein biomarker and with an antibody or an antigen binding fragment thereof that specifically binds one or more protein biomarkers selected from Brain Derived Neurotrophic Factor (BDNF), Glial Fibrillary Acidic Protein (GFAP), Intracellular Adhesion Molecule 5 (ICAM5), Metallothionein 3 (MT3), Oligodendrocyte Myelin Glycoprotein (OMG), Neurogranin (NRGN), or Neuron Specific Enolase (NSE); (b) assaying binding of the antibody or an antigen binding fragment thereof to ALDOC and to the one or more biomarkers in the sample; and (c) detecting mTBI or concussion in the subject if the biomarker levels are increased or decreased in the sample relative to a control level. In an embodiment, an increased level of ALDOC and/or GFAP indicates mTBI or concussion in said subject. In an embodiment, the subject's brain is assessed by neuroimaging to detect changes in vascular or BBB permeability in areas of the brain as further indicating mTBI or concussion in the subject. In an embodiment, assaying of binding by the antibody or an antigen binding fragment thereof is carried out by an immunoassay, an immunoblotting method, an immunoprecipitation assay, an immunostaining method, a quantitative assay, an immunofluorescent assay, or a chemiluminescence assay. In a particular embodiment, assaying of binding is carried out by an immunoassay, for example, without limitation, an enzyme linked immunosorbent assay (ELISA), fluorescence-linked immunosorbent assay (FLISA), or a mesoscale discovery electrochemiluminescence ELISA (MSD-ELISA). In an embodiment, an increase in the level of the ALDOC and GFAP biomarkers relative to control and the detection of BBB permeability in the subject indicates mTBI in the subject. In an embodiment, an increase in the levels of the ALDOC, GFAP, OMG and NSE biomarkers relative to control levels and the detection of BBB permeability in the subject indicates mTBI in the subject. In an embodiment, a decrease in the levels of the BDNF and SNCB biomarkers relative to control levels and the detection of BBB permeability in the subject indicates mTBI in the subject.

In another aspect, the invention provides a method of ascertaining whether a patient who has sustained mTBI or concussion can return to work or play, in which the method includes: (a) measuring the level of ALDOC and/or GFAP protein biomarkers in a sample obtained from the patient relative to a reference level at first time point; (b) measuring the level of ALDOC and/or GFAP protein biomarkers in a sample obtained from the patient at second time point subsequent to the first time point; (c) neuroimaging blood brain barrier (BBB) permeability signals in the brain of the subject to detect a change in vascular permeability in a BBB area; and (d) ascertaining that the patient can return to work or play if the ALDOC and/or GFAP biomarker levels measured at the second time point are decreased or trending to normal levels versus the levels of these biomarkers measured at the first time point and if any change in vascular permeability in the BBB area is resolved at the second time point. In an embodiment, the method further includes measuring the levels of one or more biomarker proteins at the first and second time points to determine respective increases or decreases, wherein the one or more biomarker proteins is selected from Brain Derived Neurotrophic Factor (BDNF), Intracellular Adhesion Molecule 5 (ICAM5), Metallothionein 3 (MT3), Oligodendrocyte Myelin Glycoprotein (OMG), Neurogranin (NRGN), or Neuron Specific Enolase (NSE). In an embodiment, the reference level of step (a) is the level of ALDOC, GFAP, and/or the one or more biomarkers present in a normal subject who does not have mTBI or concussion. In an embodiment, the reference level of step (b) is the level of ALDOC, GFAP, and/or the one or more biomarkers present in a biological sample from the same subject at the first time point. In an embodiment, detecting decreased levels of one or more of the ALDOC, GFAP or NSE biomarkers or no increase in said levels indicates that said subject can return to play or work. In an embodiment, steps (a)-(c) are repeated at one or more predetermined intervals to monitor the levels of ALDOC, GFAP, and the one or more biomarkers in the subject. In an embodiment, steps (a)-(c) are repeated at one or more predetermined intervals to monitor the levels of ALDOC, GFAP, and the one or more biomarkers in the subject. In an embodiment, neuroimaging analysis is performed on the brain of the subject to detect a change in vascular or BBB permeability in the brain at one or more predetermined times following the second time point to detect unresolved vascular damage in the BBB areas or to assess whether the subject is at risk for more severe or secondary vascular damage. In an embodiment, the more severe or secondary vascular damage is selected from major hemorrhage, edema, blood vessel leakage, or aneurysm.

In yet another aspect, the invention provides a method of differentially diagnosing severe traumatic brain injury (sTBI) versus mild traumatic brain injury (mTBI) in a patient following a head or brain injury, in which the method includes: (a) measuring the levels of the biomarkers Aldolase C (ALDOC) and/or glial fibrillary protein (GFAP) in a biological sample obtained from a patient on the day of injury relative to a control level; (b) diagnosing the patient as having mTBI if the level of the ALDOC biomarker detected on the day of injury is elevated or increased relative to control level and if no detectable level of GFAP relative to control level is present on the day of injury; (c) measuring the levels of ALDOC and/or GFAP biomarkers in a biological sample obtained from the same patient on one or more days subsequent to the day of injury relative to control levels; and (d) diagnosing the patient as having sTBI if the level of the GFAP biomarker is elevated or increased on the one or more days subsequent to the day of injury, but is not elevated or increased on the day of injury; or if the levels of both the ALDOC and GFAP biomarkers are elevated or increased relative to control levels on the one or more days subsequent to the day of injury. In an embodiment, the method further includes measuring the level of brain-specific lipid binding protein (BLBP) relative to a control level on the day of injury and on one or more days subsequent to the injury, and detecting an elevated or increased level of BLBP on the day of injury and on one or more days subsequent to the day of injury relative to control level.

In embodiments of the methods of any of the above aspects, the biological sample is selected from blood, serum, plasma, or cerebrospinal fluid (CSF). In an embodiment of the methods of any of the above aspects, the control or reference level is the level of the one or more protein biomarkers present in a normal subject not having a traumatic brain injury, mTBI or concussion. In an embodiment of the methods of any of the above aspects, the subject is an athlete, for example, without limitation, a football player.

In another aspect, a method of detecting severity of brain injury in a subject who has or who is suspected of having a brain injury is provided, in which the method involves contacting a biological sample obtained from the subject with antibodies that specifically bind to Glial Fibrillary Acidic Protein (GFAP) and to Neuron Specific Enolase (NSE) in a sample obtained from the subject; measuring the levels of the GFAP and NSE biomarker proteins in the subject's sample compared with control levels in an antibody binding assay; neuroimaging the subject by CT scan predicated on measuring an increase in the levels of the GFAP and NSE biomarker protein in the sample; and detecting that the subject has an intracranial bleed or hemorrhage by CT scan, indicating that the subject has a serious brain injury. In an embodiment, the method further involves measuring an increased level of Neurogranin (NRGN) biomarker protein in the subject's sample compared with a control level; and detecting an epidural and subdural hemorrhage in the subject by CT scan based on the increased levels of NRGN, GFAP and NSE biomarker proteins measured in the subject's sample.

In another aspect, a method of detecting severity of brain injury in a subject who has or who is suspected of having a brain injury is provided, in which the method involves contacting a biological sample obtained from the subject with antibodies that specifically bind to Glial Fibrillary Acidic Protein (GFAP) and to Neuron Specific Enolase (NSE) biomarker proteins in a sample obtained from the subject; measuring the levels of the GFAP and NSE biomarker proteins in the subject's sample compared with control levels in an antibody binding assay; neuroimaging the subject by CT scan predicated on measuring an increased level of GFAP and an unaltered level of NSE in the subject's sample compared to control levels; and detecting that the subject has intraventricular bleeding or hemorrhage by CT scan, thus indicating that the subject has a serious brain injury.

In another aspect, a method of detecting whether a subject who has or who is suspected of having a brain injury has parenchymal involvement including subarachnoid hemorrhage or contusion is provided, in which the method involves contacting a biological sample obtained from the subject with antibodies that specifically bind to Aldolase C (ALDOC), to Glial Fibrillary Acidic Protein (GFAP) and to Neuron Specific Enolase (NSE) biomarker proteins in a sample obtained from the subject; measuring the levels of the ALDOC, GFAP and NSE biomarker proteins in the subject's sample compared with control levels in an antibody binding assay; neuroimaging the subject by CT scan predicated on measuring a decreased level of ALDOC and increased levels of GFAP and NSE in the subject's sample compared to control levels; and detecting subarachnoid hemorrhage and/or contusion in the subject by CT scan, thus indicating that the subject has a serious brain injury.

In another aspect, a method of detecting whether a subject who has or who is suspected of having a brain injury has a midline shift is provided, in which the method involves determining the levels of biomarker proteins Glial Fibrillary Acidic Protein (GFAP) and Neurogranin (NRGN) in a sample obtained from the subject by measuring the biomarker protein levels by antibody binding assay or mass spectrometry analysis; neuroimaging the subject by CT scan predicated on measuring an increased level of GFAP and a decreased level of NRGN in the subject's sample compared to control levels; and detecting a midline shift in the subject by CT scan, thus indicating that the subject has serious brain injury.

In embodiments of the methods of any of the above aspects, the biological sample is one or more of blood, serum, plasma, or cerebrospinal fluid (CSF). In a particular embodiment, the sample is serum. In embodiments of the methods of any of the above aspects, binding of an antibody (or an antigen binding fragment thereof) to a biomarker protein is measured using an immunoassay, an immunoblotting method, an immunoprecipitation assay, an immunostaining method, a quantitative assay, an immunofluorescent assay, or a chemiluminescence assay. In particular embodiments, the immunoassay is an enzyme linked immunosorbent assay (ELISA), a fluorescence-linked immunosorbent assay (FLISA) or a mesoscale discovery electro-chemiluminescence ELISA (MSD-ELISA). In an embodiment of the methods of any of the above aspects, the CT scan detection of bleeding or hemorrhage or midline shift in the brain of the subject indicates that the subject cannot return to work or play. In an embodiment the methods of any of the above aspects, the methods further include measuring the levels of one or more protein biomarkers selected from the group consisting of Brain Derived Neurotrophic Factor (BDNF), Neurogranin (NRGN), Neuron Specific Enolase (NSE), Oligodendrocyte Myelin Glycoprotein (OMG) and Synuclein Beta (SNCB) relative to control levels. In an embodiment, the levels of one or more of the biomarkers are increased relative to control levels. In an embodiment, the levels of one or more of the biomarkers are decreased relative to control levels. In another embodiment of the methods of any of the above aspects, the method further includes neuroimaging the brain of the subject to determine whether the subject has suffered damage to specific white matter areas or tracts in the brain. In embodiments, the white matter areas or tracts in the brain include one or more of cingulum cingulate tracts, cingulum hippocampal tracts, the inferior fronto-occipital fasciculae (IFOF), the inferior lateral fascicule (ILF), the superior lateral fascicule (SLF), or the corpus callosum forceps major In another of its aspects, a method of qualifying brain injury severity in a subject is provided, in which the method involves contacting a biological sample from the subject with an antibody that specifically binds one or more brain specific biomarker proteins selected from Neurogranin (NRGN), Synuclein Beta (SNCB), Neuron Specific Enolase (NSE), Glial Fibrillary Acidic Protein (GFAP), Brain Derived Neurotrophic Factor (BDNF), Oligodendrocyte Myelin Glycoprotein (OMG), or Aldolase C (ALDOC) in an antibody binding assay; neuroimaging the subject to visualize fiber tracts in the brain when the levels of one or more of the biomarker proteins in the subject's sample are changed compared with control levels based on the antibody binding assay; and detecting a change in one or more fiber tracts in the brain correlated with the changes in the levels of the one or more biomarker proteins, thereby qualifying the subject as having a serious brain injury. In an embodiment of the method, the levels of one or more of the NRGN, SNCB or NSE biomarkers are increased relative to control levels and changes are detected in one or more long fiber tracts in the brain. In an embodiment of the method, the levels of the BDNF biomarker are increased relative to control levels and changes are detected in one or more long fiber tracts in the brain. In an embodiment of the method, changes are detected in one or more long fiber tracts in the brain selected from the inferior fronto-occipital fasciculus (IFOF) tract, the inferior lateral fasciculus (ILF) tract, the cingulum cingulate tract and the hippocampal tract. In an embodiment, the neuroimaging is MRI, more specifically, contrast MRI, or Diffusion Tensor Imaging MRI (DTI-MRI). In an embodiment of the method, the subject suffers from repetitive sub-concussive injury as indicated by determining damage to specific fiber tracts in the brain. In an embodiment of the method, detecting the changes to the fiber tracts in the brain correlated with the changes in the levels of the one or more biomarker proteins indicates that the subject should not return to work or play.

In another aspect, the invention also provides a kit. The kit includes components for performing an immunoassay to assess the biomarkers described herein in the context of mTBI or concussion as brain injury including, for example, necessity for treatment and type of treatment, or additional assessment by neuroimaging analysis (e.g., MRI or CT scan). The kit can include antibodies or an antigen binding fragment thereof that specifically bind a panel of biomarker proteins, wherein the panel includes subsets of biomarker proteins selected from Neurogranin (NRGN), Synuclein Beta (SNCB), Neuron Specific Enolase (NSE), Glial Fibrillary Acidic Protein (GFAP), Brain Derived Neurotrophic Factor (BDNF), Oligodendrocyte Myelin Glycoprotein (OMG), and/or Aldolase C (ALDOC). In particular embodiments, the kit includes antibodies or an antigen binding fragment thereof that specifically bind ALDOC and OMG; GFAP and OMG; ALDOC, NRGN and OMG; GFAP, NRGN and OMG; ALDOC, BDNF and NSE; GFAP, BDNF and NSE; BDNF and SNCB; ALDOC, NRGN and BDNF; or GFAP, NRGN and BDNF; or GFAP and BDNF; GFAP and NRGN; GFAP, NSE and NRGN; or NRGN, SNCB and NSE. In particular embodiments, the kit includes a substrate for performing the immunoassay. The kit can also comprise detection reagents and instructions for use.

The above summary is not intended to limit the scope of the described and claimed embodiments, which may be ascertained from the appended claims.

Definitions

The meaning of certain terms and phrases employed in the specification, examples, and appended claims are provided. The definitions are not meant to be limiting in nature and are intended to provide a clearer understanding of certain aspects and embodiments of the invention.

As used herein, the term "antigen" is generally used in reference to any substance that is capable of reacting with an antibody. More specifically, as used herein, the term "antigen" refers to a synthetic peptide, polypeptide, protein or fragment of a polypeptide or protein, or other molecule which elicits an antibody response in a subject, or is recognized and bound by an antibody.

As used herein, the term "biomarker" refers to a molecule that is associated either quantitatively or qualitatively with a biological change. Examples of biomarkers include polypeptides, proteins or fragments of a polypeptide or protein; and polynucleotides, such as a gene product, RNA or RNA fragment; and other body metabolites. In certain embodiments, a "biomarker" means a compound that is differentially present (i.e., increased or decreased) in a biological sample from a subject or a group of subjects having a first phenotype (e.g., having a disease or condition) as compared to a biological sample from a subject or group of subjects having a second phenotype (e.g., not having the disease or condition or having a less severe version of the disease or condition). A biomarker may be differentially present at any level, but is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); or that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more. Alternatively, the differential presence of a biomarker can be characterized by a -fold change in level including, for example, a level that is decreased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold; or that is increased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold. A biomarker is preferably differentially present at a level that is statistically significant (e.g., a p-value less than 0.05 and/or a q-value of less than 0.10 as determined using, for example, either Welch's T-test or Wilcoxon's rank-sum Test).

The term "one or more of" refers to combinations of various biomarker proteins. The term encompasses 1, 2, 3, 4, 5, 6, 7, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40 . . . N, where "N" is the total number of biomarker proteins in the particular embodiment. The term also encompasses at least 1, at least 2, at least 3, at least 4, at least 5, at least 6, at least 7, at least 8, at least 9, at least 10, at least 11, at least 12, at least 13, at least 15, 16, 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40 . . . N. It is understood that the recitation of biomarkers herein includes the phrase "one or more of" the biomarkers and, in particular, includes the "at least 1, at least 2, at least 3" and so forth language in each recited embodiment of a biomarker panel.

"Altered" as used herein can refer to an increase or decrease. An increase is any positive change, e.g., by at least about 5%, 10%, or 20%; by at least about 25%, 50%, 75%, or even by 100%, 200%, 300% or more, including values between the stated percentages. A decrease is a negative change, e.g., a decrease by at least about 5%, 10%, or 20%; by at least about 25%, 50%, 75%; or even an increase by 100%, 200%, 300% or more, including values between the stated percentages. In embodiments, an alteration or change may be by as little as 1%, 2%, 3%, 4%, 5%, 10%, 15%, 20%, 25%, 30%, 40%, 45%, 50%, 55%, 60%, or even by as much as 70%, 75%, 80%, 85%, 90%, 95%, or 100%.

The "blood-brain barrier" (BBB) is a dynamic interface that separates the brain from the circulatory system and protects the central nervous system (CNS) from potentially harmful agents and chemicals while regulating the transport of molecules (e.g., glucose and amino acids) that are essential for neural function and maintaining a stable environment. The BBB is formed by highly specialized brain endothelial cells that line brain capillaries, are connected by tight junctions and transduce signals from the vascular/circulatory system and from the brain. The structure and function of the BBB is dependent upon the complex interplay between the different cell types that include the BBB, such as astrocytes, endothelial cells, and pericytes, and the extracellular matrix of the brain and blood flow in the capillaries. The "barrier" results from the selectivity of the tight junctions between endothelial cells in CNS vessels that restricts the passage of solutes. (Pardridge, W. M., 2005, NeuroRX 2(1):3-14). At the interface between blood and the brain, the endothelial cells are tightly connected by the tight junctions, which are composed of smaller subunits, frequently biochemical dimers, of transmembrane proteins such as occludin, claudins, junctional adhesion molecule (JAM), or ESAM, for example. (Ballabh, P. et al., 2004, Neurobiology of Disease, 16(1):1-13; Stamatovic, S. M., 2008, Neuropharmacology, 6(3):179-192). The high-density cells of the BBB restrict passage of substances from the bloodstream (and prevent leakiness of substances, including blood) much more than do the endothelial cells in capillaries in other regions of the body For example, astrocyte cell projections, called "astrocytic feet" or "glia limitans," surround the endothelial cells of the BBB, providing biochemical support to those cells. The BBB effectively protects the brain from most pathogens. While blood-borne infections of the brain are very rare, viral or bacterial infections that do occur in the brain are often very serious and difficult to treat. Antibodies are too large to cross the BBB, and only certain antibiotics are able to penetrate. In some cases, drugs must be administered directly into the cerebrospinal fluid (CSF). The BBB often becomes more permeable during inflammation or edema (e.g., due to ischemic infarct), thus allowing some antibiotics and phagocytic cells to across the BBB.

A change or alteration to BBB permeability may occur as a result of head or brain injury or trauma, e.g., TBI, mTBI, or concussion, as described herein and below. A change or alteration in BBB permeability or vascular permeability can damage or cause insult to the normal integrity of the BBB, which may result in blood vessel leakiness, hemorrhage, or aneurysm, which may be detected or visualized by neuroimaging of the head/brain with MRI with contrast, or 3T MRI, or with CT imaging/scan.

The term "brain injury" refers to a condition in which the brain is damaged by injury caused by an event. As used herein, an "injury" is an alteration in cellular or molecular integrity, activity, level, robustness, state, or other alteration that is traceable to an event. For example, an injury includes a physical, mechanical, chemical, biological, functional, infectious, or other modulator of cellular or molecular characteristics. An event can include a physical trauma such as a single or repetitive impact (percussive) or a biological abnormality such as a stroke resulting from either blockade or leakage of a blood vessel. An event is optionally an infection by an infectious agent. A person of skill in the art recognizes numerous equivalent events that are encompassed by the terms injury or event.

More specifically, the term "brain injury" refers to a condition that results in central nervous system damage, irrespective of its pathophysiological basis. Among the most frequent origins of a "brain injury" are stroke and traumatic brain injury (TBI). A "stroke" is classified into hemorrhagic and non-hemorrhagic. Examples of hemorrhagic stroke include cerebral hemorrhage, subarachnoid hemorrhage, and intracranial hemorrhage secondary to cerebral arterial malformation, while examples of non-hemorrhagic stroke include cerebral infarction.

A distinction is made between intra-axial hemorrhage (blood inside the brain) and extra-axial hemorrhage (blood inside the skull but outside the brain). Intra-axial hemorrhage is due to intra-parenchymal hemorrhage or intraventricular hemorrhage (blood in the ventricular system). Intra-axial hemorrhage may be caused by brain trauma, hemorrhagic stroke and/or spontaneous bleeding into the brain. Likewise, in intraparenchymal hemorrhage, intraventricular hemorrhage, or intraventricular traumatic diffuse bleeding is caused by brain trauma, hemorrhagic stroke and/or spontaneous bleeding into the brain.

The term "traumatic brain injury" or "TBI" refers to traumatic injuries to the brain which occur when physical trauma causes brain damage. For example, TBI can result from a closed head injury or a penetrating head injury. A "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, among others).

The term "mild traumatic brain injury (mTBI)" is also commonly known as "concussion" and refers to the occurrence of injury to the head or brain arising from blunt trauma or impact, or forceful motion of the head (acceleration or deceleration forces) causing one or more of the following conditions attributable to head injury: transient confusion, disorientation, or impaired consciousness; dysfunction of memory around the time of injury; or loss of consciousness lasting less than 30 minutes. One or more of the symptoms of mTBI can last a year or more following the initial head or brain injury. While early mTBI symptoms may appear to be mild, they can lead to significant, life-long impairment in an individual's ability to function physically, cognitively and psychologically. While the term "concussion" is used interchangeably with mTBI at times, concussions cover a clinical spectrum and may occur without loss of consciousness. Mild concussion may be present even if there is no external sign of trauma to the head. The spectrum of concussions related to sports injuries are defined by The Quality Standards Subcommittee of the American Academy of Neurology as follows: Grade 1 concussion: transient confusion, no loss of consciousness and duration of mental status abnormalities on examination that resolve in less than 15 minutes; Grade 2 concussion: transient confusion, no loss of consciousness, concussion symptoms or mental status abnormalities on examination that last more than 15 minutes; and Grade 3 concussion: any loss of consciousness, either brief (seconds) or prolonged (minutes). (Centers for Disease Control and Prevention).

The term "brain injury" also refers to subclinical brain injury, spinal cord injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness, medications particularly sedation and anesthesia.

As used herein, "secondary brain trauma" refers to damage to the brain of a patient post-acute brain injury, i.e., during the secondary injury phase of a TBI.

As used herein, "chronic brain injury" refers to a subject who has suffered a brain injury from three days post injury until at least 12 months previously yet continues to present symptoms of brain injury.

As used herein, "sub-acute brain injury" refers to a subject who has suffered a brain injury from about 2-5 days post injury.

A "spinal cord injury" refers to a condition in which the spinal cord receives compression/detrition due to a vertebral fracture or dislocation to cause dysfunction. As used herein, the term "anoxic-ischemic brain injury" refers to deprivation of oxygen supply to brain tissue resulting in compromised brain function and includes cerebral hypoxia. For example, anoxic-ischemic brain injury includes focal cerebral ischemia, global cerebral ischemia, hypoxic hypoxia (i.e., limited oxygen in the environment causes reduced brain function, such as with divers, aviators, mountain climbers, and fire fighters, all of whom are at risk for this kind of cerebral hypoxia), obstructions in the lungs (e.g., hypoxia resulting from choking, strangulation, the crushing of the windpipe).

The term "brain injury biomarker" (BIB), "brain injury biomarker protein", "brain injury biomarker peptide", brain injury biomarker polypeptide" and the like refer to a protein, including those described herein, that can be used in methods according to the principles of the invention, e.g., to diagnose and/or detect brain injury, e.g., mTBI or concussion, in a patient. As described herein, brain injury biomarker proteins include, but are not limited to, ALDOC, GFAP, OMG, NRGN, NSE, BDNF and SNCB. In embodiments, the brain injury biomarker protein, such as set forth above, is a polypeptide or a fragment thereof having at least about 85% amino acid sequence identity to the amino acid sequence of the specific biomarker protein. In embodiment, the polypeptide or a fragment thereof has at least about 90%, 95%, or 98% amino acid sequence identity to the amino acid sequence of the specific biomarker protein.

The term "brain injury biomarkers" also includes the isoforms and/or post-translationally modified forms of any of the foregoing. The invention contemplates the detection, measurement, quantification, determination and the like of both unmodified and modified (e.g., citrullination or other post-translational modification) proteins/polypeptides/peptides, as well as autoantibodies to any of the foregoing. Citrullination of brain injury biomarkers is disclosed in U.S. Patent Application Publication No. 2015/0031048. In certain embodiments, it is understood that reference to the detection, measurement, determination, and the like, of a biomarker refers to detection of the protein/polypeptide/peptide (modified and/or unmodified). In other embodiments, reference to the detection, measurement, determination, and the like, of a biomarker refers to detection of autoantibodies of the protein/polypeptide/peptide.

As used herein, the terms "comparing" or "comparison" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, a patient having brain injury, not having brain injury, is responding to treatment for brain injury, is not responding to treatment for brain injury, is/is not likely to respond to a particular treatment for brain injury, or having/not having another disease or condition. In a specific embodiment, the term "comparing" refers to assessing whether the level of one or more biomarkers of the invention in a sample from a patient is the same as, more or less than, different from or other otherwise correspond (or not) to levels/ratios of the same biomarkers in a control sample (e.g., predefined levels/ratios that correlate to uninfected individuals, standard brain injury levels/ratios, etc.).

In another embodiment, the terms "comparing" or "comparison" refers to making an assessment of how the proportion, level or cellular localization of one or more biomarkers in a sample from a patient relates to the proportion, level or cellular localization of another biomarker in the same sample. For example, a ratio of one biomarker to another from the same patient sample can be compared.

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient is improving, not improving, etc. In specific embodiments, the parameter may include the level of one or more biomarkers of the invention. A particular set or pattern of the amounts of one or more biomarkers may indicate that a patient has improved or worsened. In other specific embodiment, the parameter may include the level of one or more biomarkers as described herein and the finding of a change or alteration in normal BBB permeability by neuroimaging of the head/brain of a subject. For example, a change or alteration can be blood vessel leakiness or blood vessel damage.

In other embodiments, a particular set or pattern of the amounts of one or more biomarkers may be correlated to a patient being unaffected (i.e., indicates a patient does not have brain injury). In certain embodiments, "indicating," or "correlating," as used according to the invention, may be by any linear or non-linear method of quantifying the relationship between levels/ratios of biomarkers to a standard, control or comparative value for the assessment of the diagnosis, prediction of brain injury or progression thereof, assessment of efficacy of clinical treatment, identification of a patient that may respond to a particular treatment regime or pharmaceutical agent, monitoring of the progress of treatment, and in the context of a screening assay, for the identification of a therapeutic for brain injury.

"Computed tomography (CT)" scan (also called "CT imaging" herein) is a mode of neuroimaging analysis that combines a series of X-ray images taken from different angles, in which computer processing is used to create cross-sectional images, or slices of soft tissue, bone and blood vessels inside the body. CT imaging analyses can be used to visualize nearly all parts of the body and provide more detailed information about internal injury and/or trauma than do plain 2-dimensional X-rays, particularly for the purposes of determining whether intervention is needed, or to plan medical, surgical, or radiation treatment(s). In embodiments, a head CT scan is performed to detect abnormalities in the brain, such bleeding or hemorrhage.

"Magnetic resonance imaging (MRI)" of the brain is a noninvasive and painless neuroimaging test for detailed visualization and analysis that uses a magnetic field and radio waves to produce detailed images of the brain and the brain stem. Unlike a CAT scan (also called a CT scan; computed axial tomography scan), an MRI scan does not involve the use of radiation. In some cases, a dye (contrast dye) or contrast material (e.g., iodine, barium, or gadolinium) is used during the MRI to allow visualization of the brain structures (e.g., blood vessels and tissue) more clearly. For example, the dye may show blood flow and areas of inflammation or edema. In some cases, MRI is DCE-MRI, DTI-MRI or 3T MRI.

During an MRI scan, radio waves manipulate the magnetic position of the atoms of the body, e.g., the head or cranium, which are picked up by a powerful antenna and sent to a computer. The computer performs millions of calculations, resulting in clear, cross-sectional black and white images of the body. These images can be converted into three-dimensional (3-D) pictures of the scanned area, which assists in pinpointing problems in the brain and the brain stem when the scan focuses on those areas. MRI can detect a variety of conditions of the brain such as cysts, tumors, bleeding, swelling, developmental and structural abnormalities, infections, inflammatory conditions, or problems with the blood vessels. It can determine if a shunt is working and detect damage to the brain caused by an injury or a stroke.

MRI of the brain can be useful in evaluating problems such as persistent headaches, dizziness, weakness, and blurry vision or seizures, and it can help to detect certain chronic diseases of the nervous system, such as multiple sclerosis. In some cases, MRI can provide clear images of parts of the brain that cannot be seen as well with an X-ray, CAT scan, or ultrasound, making it particularly valuable for diagnosing problems with the pituitary gland and brain stem.

The terms "patient," "individual," or "subject" are used interchangeably herein, and refer to a mammal, particularly, a human. The patient may have a mild, intermediate or severe disease or condition. The patient may be an individual in need of treatment or in need of diagnosis based on particular symptoms or personal or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining or providing a patient sample and/or detecting the level (or amount) of a biomarker(s) in a sample. In one embodiment, the terms refer to obtaining or providing a patient sample and detecting the level of one or more biomarkers in the sample. In another embodiment, the terms "measuring" and "determining" mean detecting the level of one or more biomarkers in a patient sample. The term "measuring" is also used interchangeably throughout with the term "detecting." In certain embodiments, the term is also used interchangeably with the term "quantifying."

The terms "sample," "patient sample," "biological sample," "biologic sample," "biofluid sample," and the like, encompass a variety of sample types obtained from a patient, individual, or subject and can be used in a diagnostic or monitoring assay. The patient (or subject) sample may be obtained from a healthy subject or a patient suspected of having or having associated symptoms of brain injury. Moreover, a sample obtained from a patient can be divided and only a portion may be used for diagnosis. Further, the sample, or a portion thereof, can be stored under conditions to maintain sample for later analysis. The definition specifically encompasses blood, cerebrospinal fluid (CSF) and other liquid samples of biological origin (including, but not limited to, peripheral blood, serum, plasma, cord blood, amniotic fluid, tears, urine, saliva, sweat, sputum, stool, secretions and synovial fluid), solid tissue samples such as a biopsy specimen or tissue cultures or cells derived therefrom and the progeny thereof. In a specific embodiment, a sample includes a blood sample. In another embodiment, a sample includes a plasma sample. In yet another embodiment, a serum sample is used. In certain embodiments, a sample includes cerebrospinal fluid.

The definition of "sample" also includes samples that have been manipulated in any way after their procurement, such as by centrifugation, filtration, precipitation, dialysis, chromatography, treatment with reagents, washing, or enriched for certain cell populations. The terms further encompass a clinical sample, and also include cells in culture, cell supernatants, tissue samples, organs, and the like. Samples may also include fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control," a "control sample," a "reference" or simply a "control." A "suitable control," "appropriate control," "control sample," "reference" or a "control" is any control or standard familiar to one of ordinary skill in the art useful for comparison purposes. A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "brain injury-positive reference level" of a biomarker means a level of a biomarker that is indicative of brain injury in a subject, and a "brain injury-negative reference level" of a biomarker means a level of a biomarker that is indicative of no brain injury of in a subject.

A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., ELISA, FLISA, PCR, LC-MS, GC-MS, etc.), where the levels of biomarkers may differ based on the specific technique that is used.

In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the invention may be assayed for levels/ratios in a sample from an unaffected individual (UI) (e.g., no brain injury) or a normal control individual (NC) (both terms are used interchangeably herein). For example, a "suitable control" or "appropriate control" can be a value, level, feature, characteristic, property, ratio, etc. determined prior to performing a therapy (e.g., brain injury treatment) on a patient or a value, level, feature, characteristic, property, ratio, etc. determined prior to disease development (e.g., a baseline test). In yet another embodiment, a protein level/ratio, transcription rate, mRNA level, translation rate, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, ratio, etc. A "suitable control" can be a profile or pattern of levels/ratios of one or more biomarkers of the invention that correlates to brain injury, to which a patient sample can be compared. The patient sample can also be compared to a negative control, i.e., a profile that correlates to not having brain injury.

As used herein, the term "predetermined threshold value of expression" of a biomarker refers to the level of expression of the same biomarker (expressed, for example, in ng/ml) in a corresponding control/normal sample or group of control/normal samples obtained from normal, or healthy, subjects, i.e., subject who do not have brain injury. Further, the term "altered level of expression" of a biomarker in a sample refers to a level that is either below or above the predetermined threshold value of expression for the same biomarker and thus encompasses either high (increased) or low (decreased) expression levels. In particular embodiments, the biomarkers described herein are increased or decreased relative to age-matched (and/or sex-matched) controls.

The terms "specifically binds to," "specific for," and related grammatical variants refer to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M. As used herein, the terms "specific binding" or "specifically binding" when used in reference to the interaction of an antibody and a protein or peptide means that the interaction is dependent upon the presence of a particular structure (i.e., the epitope) on the protein.

As used herein, the terms "binding agent specific for" or "binding agent that specifically binds" refers to an agent that binds to a biomarker and does not significantly bind to unrelated compounds. Examples of binding agents that can be effectively employed in the disclosed methods include, but are not limited to, proteins and antibodies, such as monoclonal or polyclonal antibodies, or antigen-binding fragments thereof. In certain embodiments, a binding agent binds a biomarker (e.g., a polypeptide biomarker) with an affinity constant of, for example, greater than or equal to about $1 \times 10^{-6}$ M.

By "antibody" is meant any immunoglobulin polypeptide, or fragment thereof, having immunogen or antigen binding function or ability. As used herein, the terms "antibody fragments", "fragment", or "fragment thereof" refer to a portion of an intact antibody, in particular, an immunogen- or antigen-binding portion of the antibody. Examples of antibody fragments include, but are not limited to, linear antibodies; single-chain antibody molecules and fragments thereof, e.g., scFv; Fc or Fc' peptides, F(ab) and F(ab')2 fragments, and multi-specific antibodies formed from antibody fragments, which bind to an antigen. In most embodiments, the terms also refer to fragments that bind an antigen of a target molecule (e.g., a biomarker protein described herein) and can be referred to as "antigen-binding fragments." As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies that specifically binds the target antigen.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

By "an effective amount" is meant the amount of a required to ameliorate the symptoms of a disease relative to an untreated patient. The effective amount of active compound(s) used to practice the invention for therapeutic treatment of brain injury varies depending upon the manner of administration, the age, body weight, and general health of the subject. Ultimately, the attending physician or veterinarian will decide the appropriate amount and dosage regimen. Such amount is referred to as an "effective" amount.

The term "vascular permeability" refers to the property of blood capillary or microvasculature endothelium to allow for the selective exchange of substances between the blood and the surrounding tissues and through membranous barriers such as the blood-brain barrier (BBB), blood-aqueous barrier, blood-air barrier, blood-nerve barrier, blood-retinal barrier, or blood-testis barrier. While small lipid-soluble molecules, e.g., oxygen and carbon dioxide, move freely by diffusion, water and water soluble molecules cannot pass through the walls of the endothelium and are dependent on microscopic pores for passage. Tight junctions in pore areas serve to limit the movement of large molecules through the endothelial walls. In areas of the brain, changes to the BBB or vasculature (e.g., microvasculature), e.g., caused by injury, damage, insult, or inflammation, can result in a change or alteration in normal BBB permeability or vascular permeability, which permits the aberrant and often dangerous passage of large molecules and cells through tight junctions and into surrounding tissue, as well as blood vessel leakiness in the vasculature in BBB areas. The BBB is a unique barrier that prevents the brain from exposure to the blood and the adverse consequence of edema, which may be detrimental for the tightly enclosed brain. The brain vasculature has, in addition to adherens junctions, high-resistance tight junctions and an abundant basement membrane. Perivascular components, e.g., astrocytes, pericytes, and neurons, participate functionally in creating the BBB. (Claesson-Welsh, L., 2015, *Ups J Med Sci*, 120(3):135-143). In normal or healthy brains, normal BBB permeability or vascular permeability exist, i.e., no leakage of blood from blood vessels into surrounding tissue, no hemorrhaging or other damage in BBB areas. In embodiments, a change or alteration in normal BBB permeability, which may occur as a result of head or brain injury, e.g., mTBI or concussion, is detected by neuroimaging of the head/brain of a subject whose sample has been determined to have certain levels of biomarker proteins (e.g., increased or decreased) relative to control levels. In embodiments, the biomarker proteins include at least one, or at least two of ALDOC, GFAP, OMG, NRGN, NSE, BDNF and SNCB.

Ranges provided are understood to be shorthand for all of the values within the range. For example, a range of 1 to 50 is understood to include any number, combination of numbers, or subrange from the group consisting of, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, or 50.

Unless specifically stated or obvious from context, as used herein, the term "or" is understood to be inclusive.

As used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the invention.

All publications cited herein are hereby incorporated by reference herein including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the invention.

DESCRIPTION OF THE FIGURES AS EXEMPLARY EMBODIMENTS OF THE INVENTION

Figure 1D:
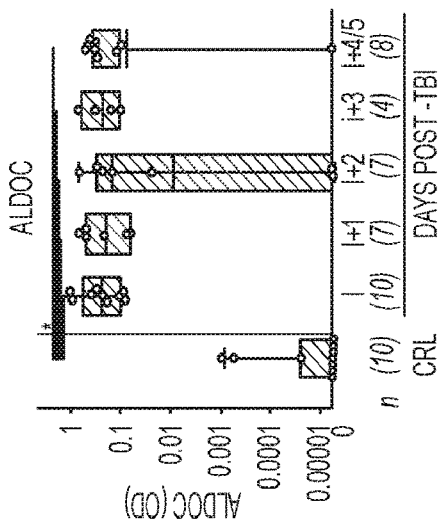
Figure 1C:
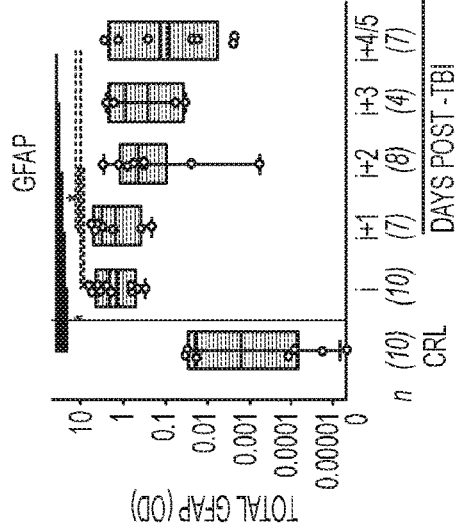
Figure 1B:
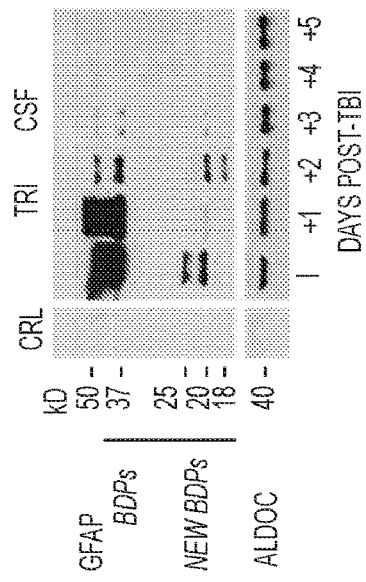
Figure 1F:
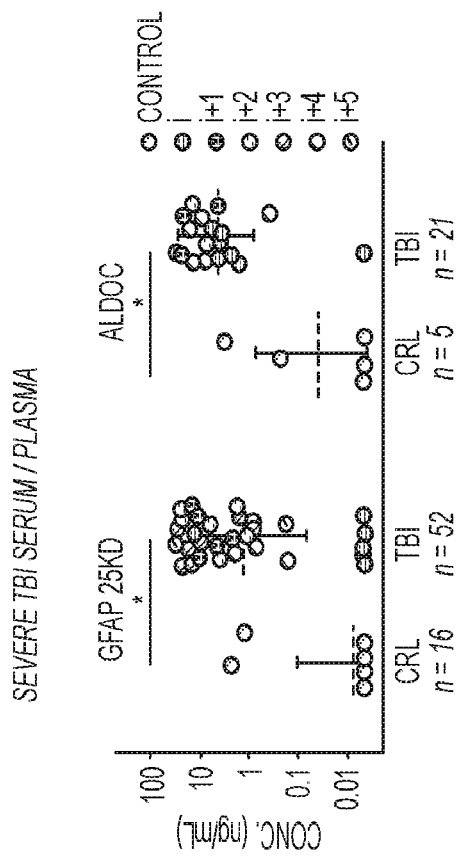
Figure 1E:
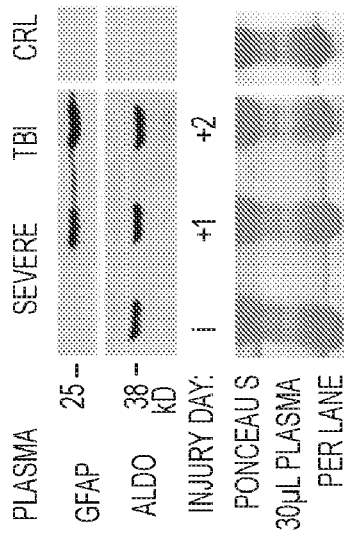
Figure 1G:
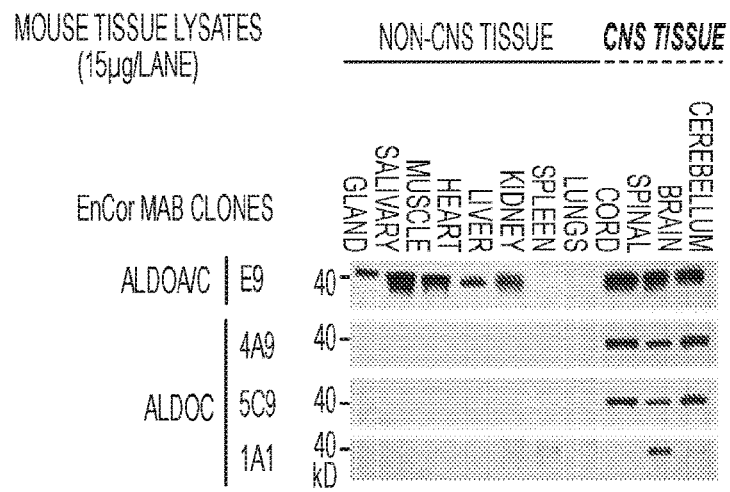

FIGS. 1A-1G show a schematic, Western blots and densitometry plots demonstrating that Aldolase C (ALDOC), a brain-specific isoform of the Aldolase proteins that constitutes 1-2% of the brain protein mass, is a biomarker that is released within minutes after head or brain trauma. FIGS. 1B-1F illustrate the detection of ALDOC and GFAP in cerebrospinal fluid (CSF) from TBI patients versus controls. FIG. 1A shows mass-spectrometry protein identification in cerebrospinal fluid (CSF) of control (9) and TBI patients (19). Selection criteria were: (1) trauma-release, (2) astrocyte-enriched and (3) absence in healthy plasma. FIGS. 1B-1D: analysis of cerebrospinal fluid (CSF) from 25 patients with severe TBI and 11 controls. FIG. 1B demonstrates the detection of ALDOC and GFAP breakdown products (BDPs) in CSF by Western blot versus a healthy control during first post-injury week. FIGS. 1C and 1D show quantification of these proteins by densitometry measurement. Total GFAP BDP levels decreased significantly (red*) on post-injury days (FIGS. 1B and 1C), while ALDOC levels (FIGS. 1B and 1D) were stable (repeated measures ANOVA). CSF with low biomarker signals had overall low protein amounts. FIG. 1E shows a Western blot of depleted plasma showing a 25 kD BDP of GFAP and ALDOC detected in a patient with severe TBI (sTBI). FIG. 1F depicts a plot of the data from the same cohort showing median GFAP-BDP and ALDOC levels using densitometry with recombinant protein calibration (Mann-Whitney rank sum test). Shown are analyses of serum/plasma concentrations from immunoblot scaled densitometry, standardized using known amounts of the respective pure proteins in a cohort of patients with severe (sTBI) on injury day (red) and at different times (days) post-injury relative to control levels. GFAP (25 kD) levels were more elevated after the initial day of injury (first postinjury day onward); ALDOC levels were elevated after initial injury and on all days onward (repeated measures ANOVA, mixed model). FIG. 1G presents a tissue Western blot showing binding of anti-Aldolase antibodies to various mouse CNS and non-CNS tissues. The Western blot shows that anti-ALDOC monoclonal antibody clones 4A9, 5C9 and 1A1 (EnCor Biotechnology, Inc., Gainesville, Fla.) are specific for the ALDOC isoform, and showed specificity for mouse CNS tissues (spinal cord, brain and cerebellum), while no binding signal for the anti-ALDOC antibodies was detected in other tissues. Antibody clone E9 detected both the ALDOA and ALDOC isoforms and showed cross-reactivity with non-CNS tissues (salivary gland, muscle, heart, liver and kidney). Compared with antibody E9, the anti-ALDOC-specific monoclonal antibodies 4A9, 5C9, and 1A1 were selected for further studies.

Figure 2A:
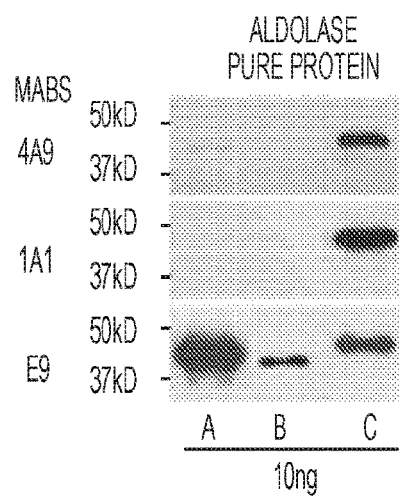
Figure 2B:
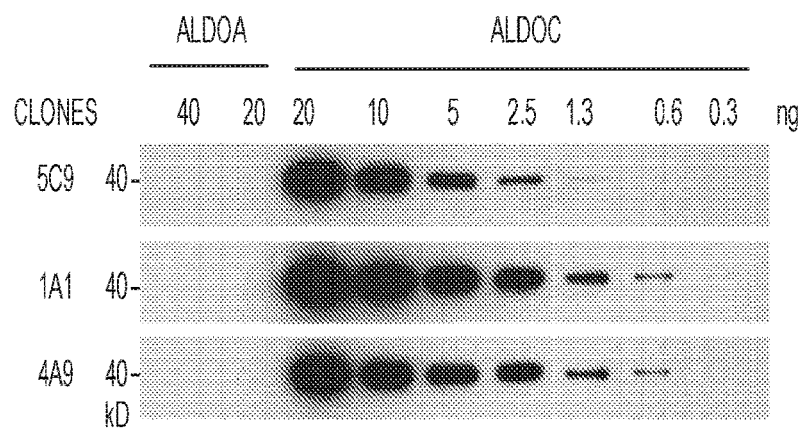
Figure 2C:
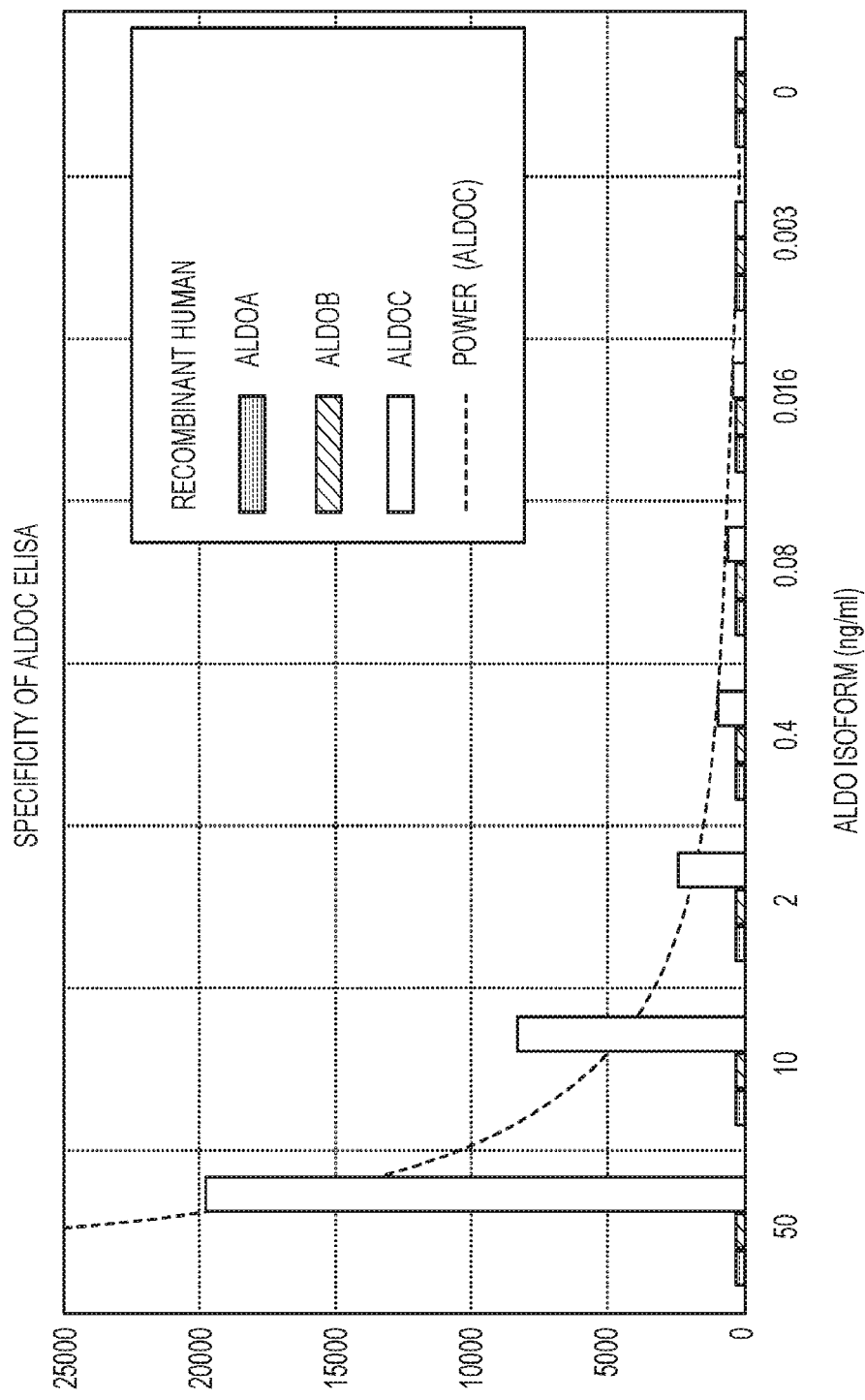

FIGS. 2A-2C show Western blots and a graph illustrating the specificity of anti-ALDOC antibody for binding to recombinant ALDOC versus recombinant Aldolase A (ALDO-A) and Aldolase B (ALDO-B) isoforms. The Western blot in FIG. 2A shows the detection of ALDOC by monoclonal antibody clones 4A9 and 1A1 (Encor Biotechnology, Inc.), and the detection of ALDO-A, ALDO-B and ALDOC recombinant proteins by monoclonal antibody clone E9. FIG. 2B presents a Western blot demonstrating the specificity of the 5C9, 1A1 and 4A9 anti-ALDOC monoclonal antibody clones described above for binding to recombinant ALDOC versus recombinant ALDO-A. For the blot, various amounts of pure ALDOA and ALDOC were detected using 3 monoclonal antibody clones as shown. Antibody was used at a 1:1000 dilution. Antibody 5C9 detected 0.6 ng of ALDOC when used at a 1:300 dilution. No cross-reactivity to ALDOA and ALDOB (not shown) was detected. FIG. 2C presents a sandwich ELISA (ImmunArray Meso Scale Discovery (MSD) ELISA) analysis using purified recombinant human ALDO-A, ALDO-B, and ALDO-C, ("ALDOC"); an antibody specific for ALDOC, clone 4A9, as capture antibody; and polyclonal rabbit antisera as detecting antibody. Shown in the x-axis of the graph is recombinant human ALDO isoform (ng/ml). The specificity of the anti-ALDO-C antibody for recombinant human ALDO-C in the ELISA is observed, with no signal detected for the same concentrations of the ALDOA and ALDOB isoforms.

Figure 3A:
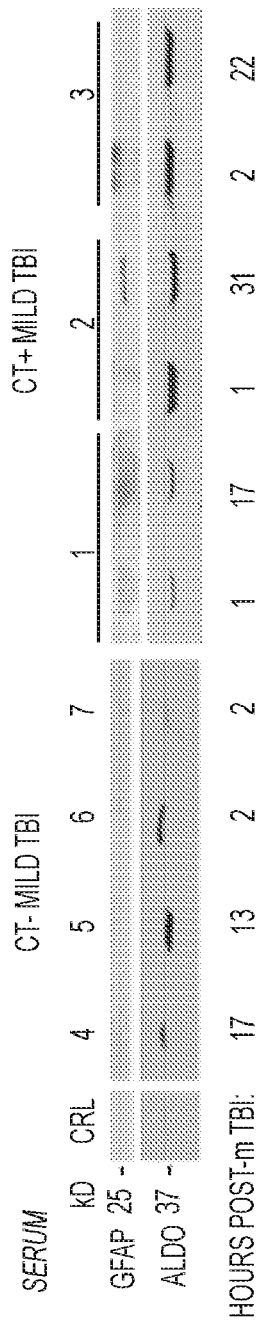
Figure 3B:
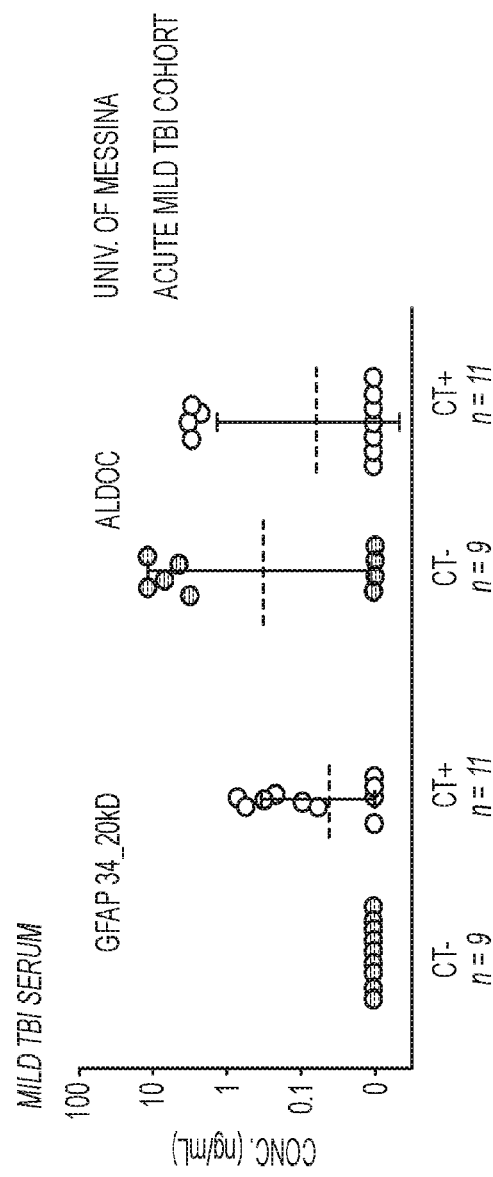
Figure 3C:
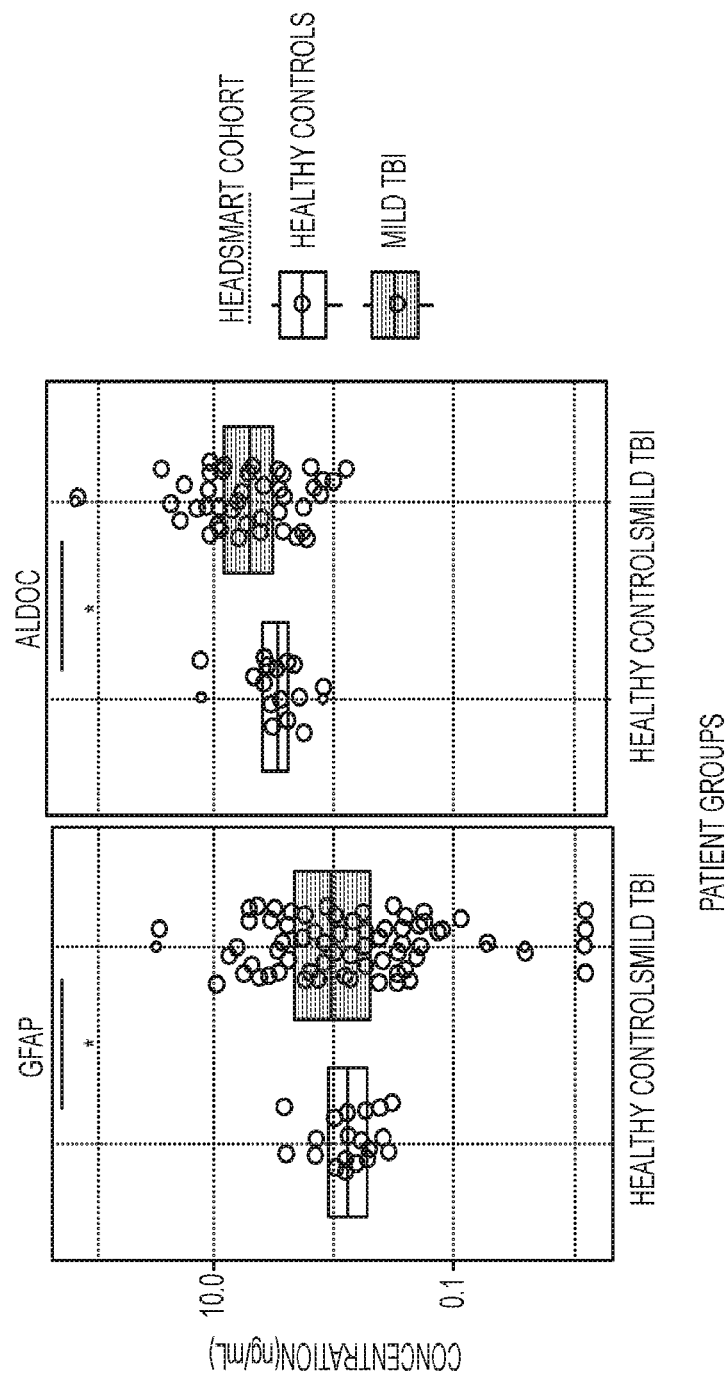

FIGS. 3A-3C show Western blots and plots ("jitterplots") assessing ALDOC and GFAP in 4 separate cohorts or brain-injured patients versus athletic controls. (Example 1). A small number of age-matched male patients were studied for comparisons with athletic samples (males, aged 18-40; n=90). Median baseline blood draw was 4.2 hours from injury. Serum biomarker concentrations for ALDOC and GFAP were assessed in replicate using a high sensitivity ELISA assay (ImmunArray, Richmond, Va.). (See, Example 1). FIG. 3A shows a Western blot of serum samples from CT− patients with mTBI (left) and CT+ patients with mTBI probed for the presence of GFAP and ALDOC at different times post mTBI injury. Explorative measurement of GFAP BDPs (20-34 kD) and ALDOC was performed using the EC9 anti-ALDOC specific monoclonal antibody in CT− and CT+ mTBI patients between 1-31 hours post injury. ALDOC was elevated regardless of CT-status, while GFAP-BDPs were elevated only in CT-mTBI patients. FIG. 3B is a plot of the concentration of GFAP and ALDOC in the sera of CT− and CT+ patients with mTBI. FIG. 3C presents data from a MesoScale Discovery ELISA analysis of a HeadSmart cohort (healthy controls and patients with mTBI) showing the distribution for total GFAP (n=139) and ALDOC (n=86) concentrations in healthy controls (n=20) versus patients with mTBI, with the ALDOC biomarker levels being correlated with mTBI in the patient group analyzed. *Paired T-test for GFAP, 0.0199 and ALDOC, 0.0160. The HeadSmart ("Head Injury Serum Markers for Assessing Response to Trauma Study") study of the Johns Hopkins Univerity was designed to examine blood-based biomarkers for diagnosing and determining prognosis of patients with TBI. (See, Peters, M. E. et al., January, 2017, *Brain Injury, p.* 1-9).

Figure 4A:
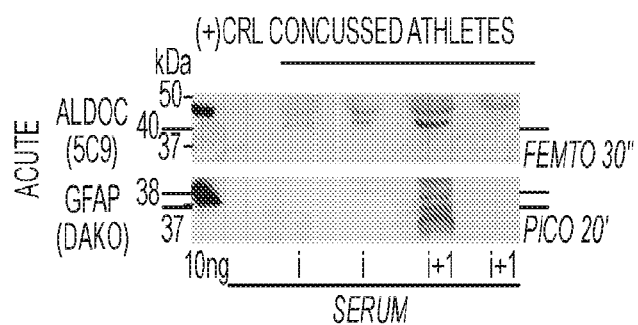
Figure 4B:
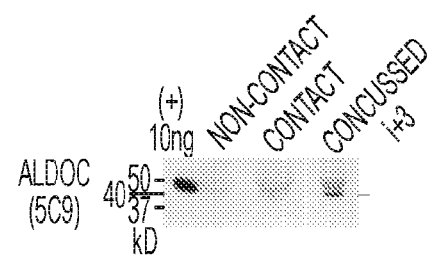
Figure 4C:
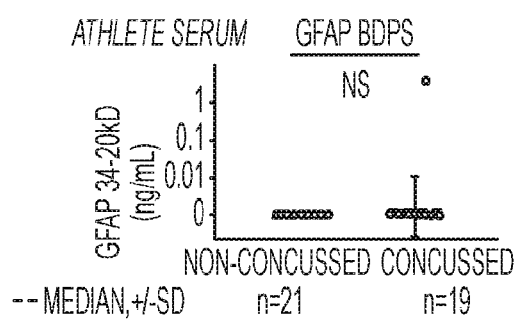
Figure 4D:
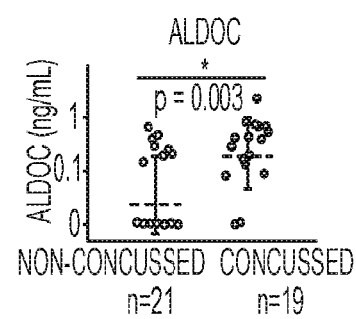
Figure 4E:
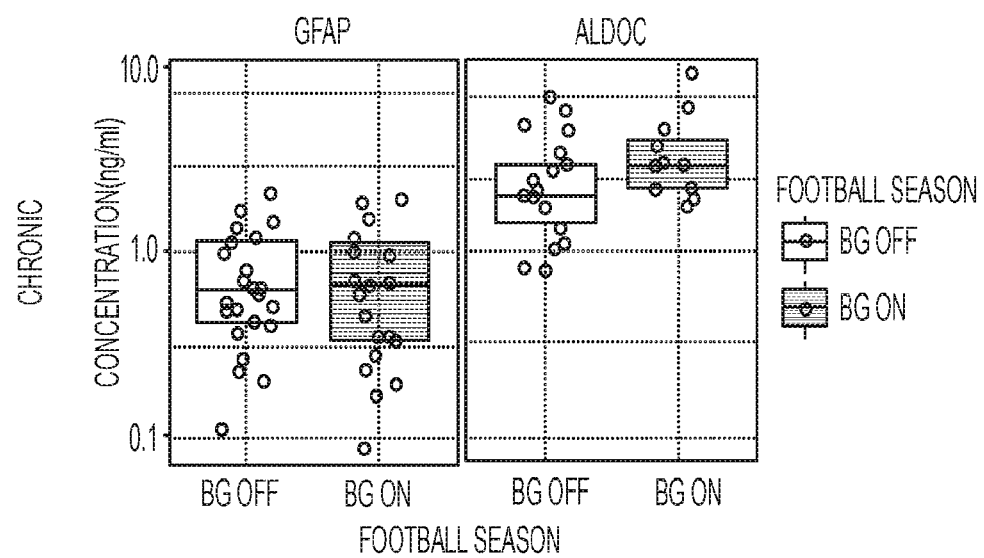

FIGS. 4A-4J show Western blots, plots (box plots), a Spearman correlation chart and a table illustrating the relationship of the detection of ALDOC and GFAP to sports concussion in athletes. FIGS. 4A-4D reflect data related to acute concussion, while FIGS. 4E-4G reflect data related to chronic concussion. FIG. 4A shows a Western blot illustrating the detection of ALDOC signal in depleted sera of all concussed athletes tested versus control athletes (non-contact sports, i.e., track, basketball) using the monoclonal antibody clone EC9 (Encor) on the day of injury (i) and on the first day post-injury (i+1). In contrast, GFAP signal (BDPs) as detected by a polyclonal rabbit antibody (Dako) was present in the serum sample of one injured athlete post-injury. FIG. 4B shows a Western blot illustrating the detection of ALDOC in sera tested from uninjured athletes in non-contact sports and in contact sports compared with serum tested from a concussed football player (contact sports athlete). The results shown in FIG. 4B demonstrate that ALDOC levels are elevated after concussion on the third day post-injury (i+3). The ALDOC specific anti-ALDOC monoclonal antibody, clone 5C9, was used for probing the Western blot in FIG. 4B. In FIGS. 4A and 4B, the calibrant (+) lanes show 10 ng of recombinant ALDOC protein or GFAP-BDP. No signal was detected in the serum of the non-contact sports player, and a faint signal was detected in the serum of a control player of contact sports (with no head injury or concussion). FIGS. 4C and 4D show quantification of Western blot results using recombinant proteins to estimate protein amounts. The results indicate a significant elevation of ALDOC (Mann-Whitney rank sum) in concussed versus non-concussed athletes, and no significant change in GFAP-BDPs. FIGS. 4E-4G illustrate data showing the relationship between ALDOC and GFAP after chronic concussion in athletes who play a contact sport (football). FIG. 4E shows ImmunArray ELISA assay results in football players during the active season ("ON") compared with outside of the season ("OFF"). In FIG. 4E, ALDOC level was elevated, while GFAP level was not.

Figure 4I:
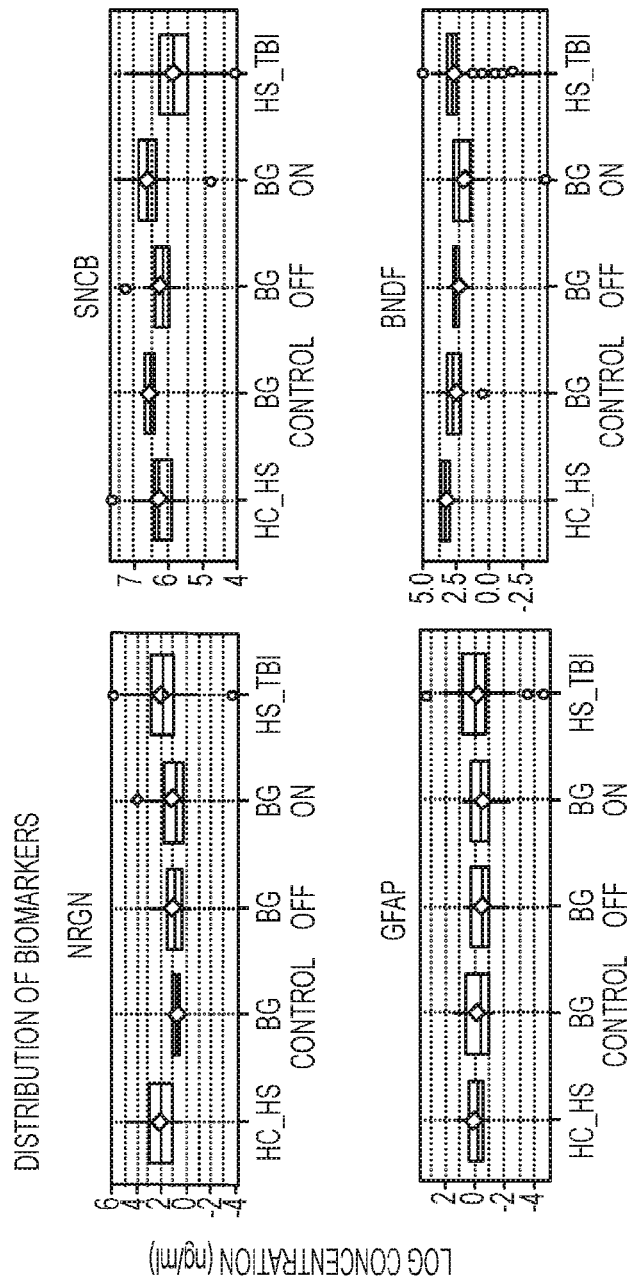
Figure 4I:
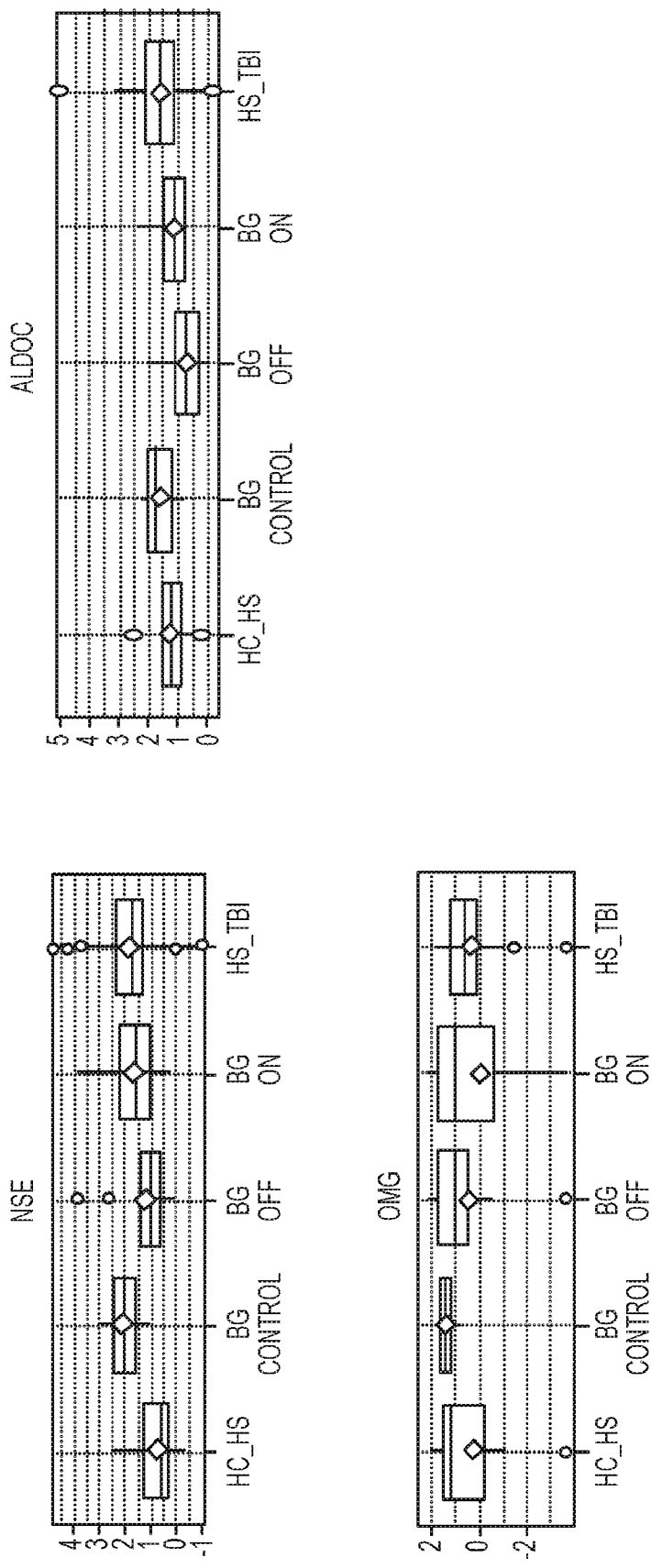
Figure 4I:
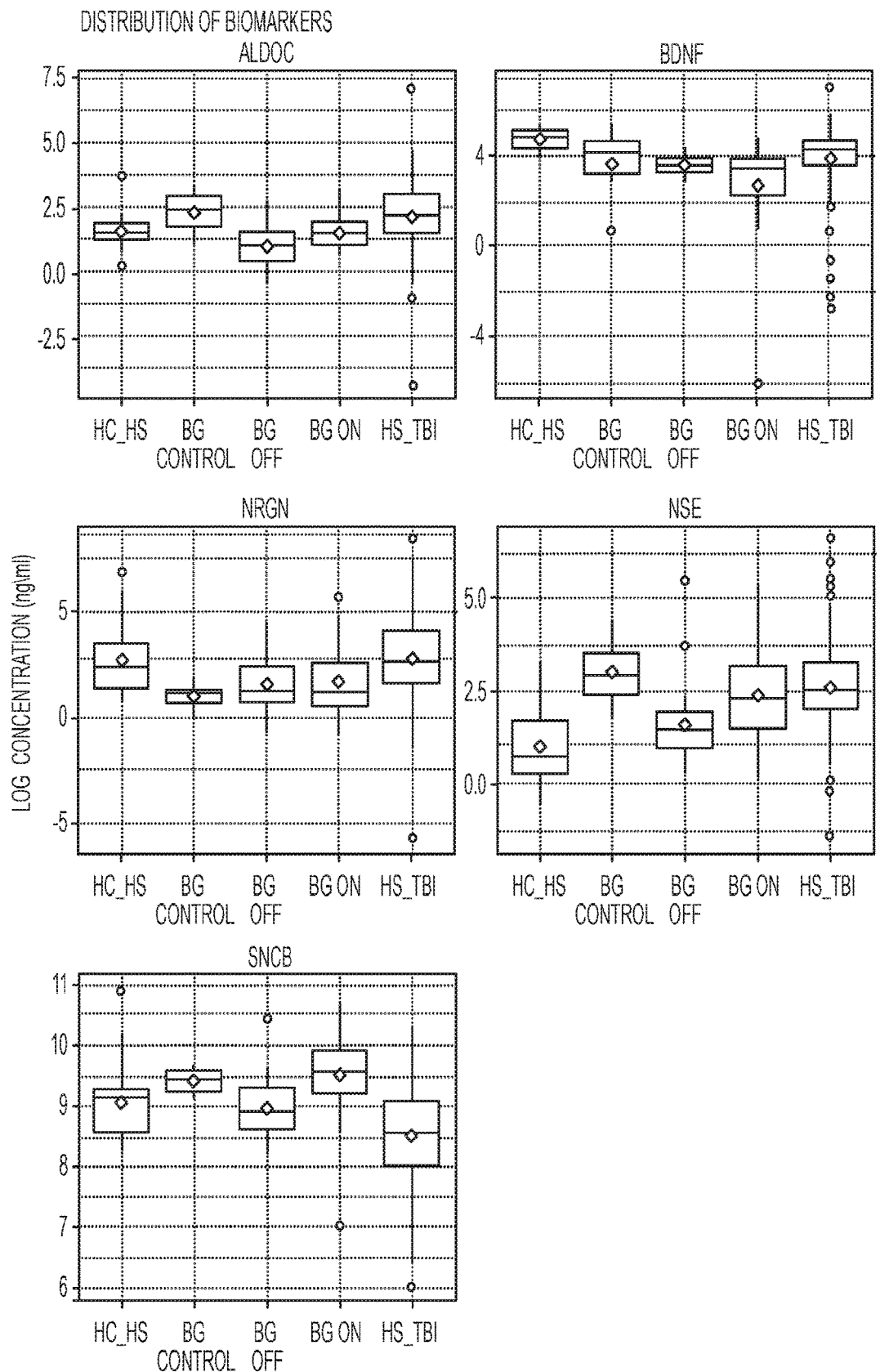
Figure 4I:
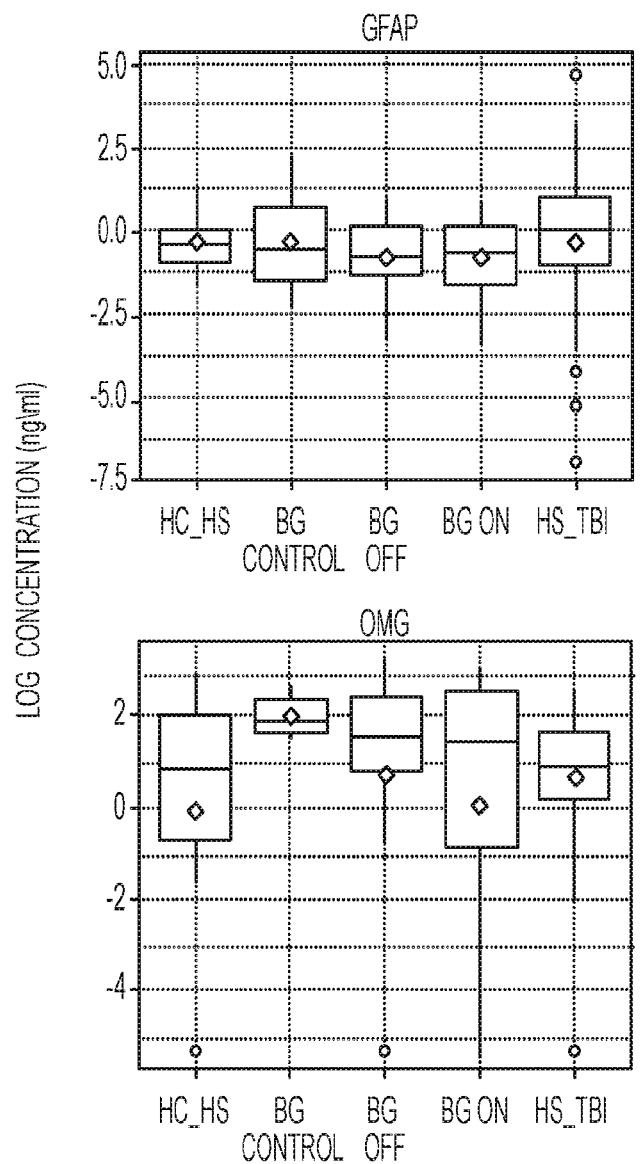
Figure 4J:
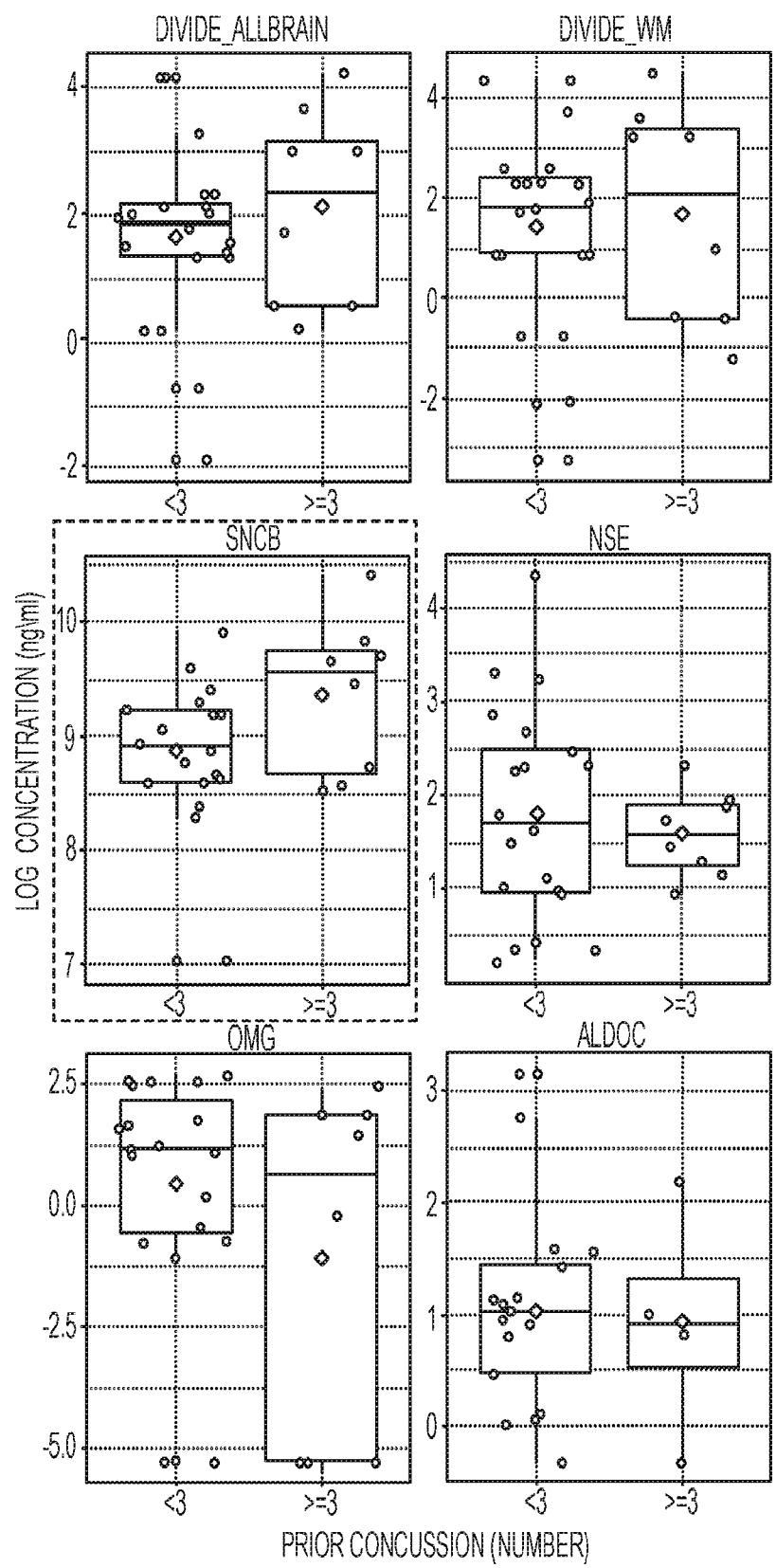
Figure 4J:
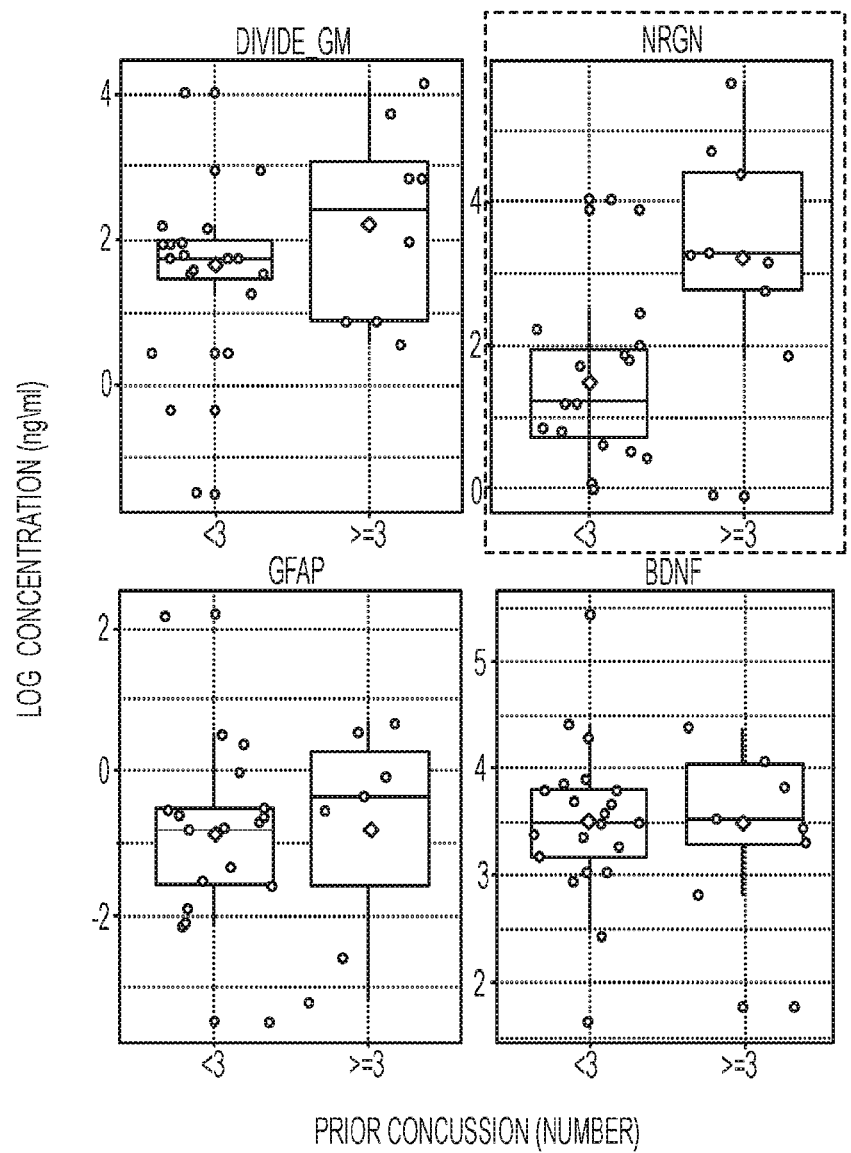

FIGS. 4F and 4G show correlations of biomarkers with contrast-enhanced (dynamic contrast enhanced or DCE) MRI results reflecting BBB leakage and normalized to local blood flow. DCE MRI signal reflects BBB (vascular) leakage. BBB permeability values were compared in whole brain (DIVIDE-Allbrain), white matter only (–WM), or gray matter only (–GM). Spearman pairwise correlation coefficient in football players with previous history of concussion and sub-concussive impacts showed a stronger correlation between ALDOC and BBB permeability (DIVIDE) and between ALDOC and GFAP levels during the active playing season, compared with the off season (based on MRI measurements and ImmunArray USA, Inc. ELISA serum detection). FIG. 4H presents a table illustrating the correlation between ALDOC and GFAP with fiber tract lesions by DTI (Spearman). FIG. 4I and FIG. 4IA present a series of box plots showing the distribution of biomarkers in healthy controls, athletic controls, athletes, and TBI patients. FIG. 4I shows the initial distributions seen in evaluation of biomarkers in these cohorts. FIG. 4IA is an addendum that represents a greater number of patients examined by the same assays, and thus is updated data, the distributions of which represent the subsequent data table updates. Serum biomarkers were detected by MSD chemiluminescent ELISA assays. (ImmunArray USA, Inc., Richmond, Va.). FIG. 4J presents box plots showing biomarker levels in serum samples obtained from football players with 3 or more concussions versus others. Specifically, serum biomarker levels of Neurogranin (NRGN) and Synuclein Beta (SNCB), emphasized by rectangular outlines of the respective box plots, were detected at higher levels in football players with 3 or more concussions versus players with 2 or fewer concussions.

Figure 5A:
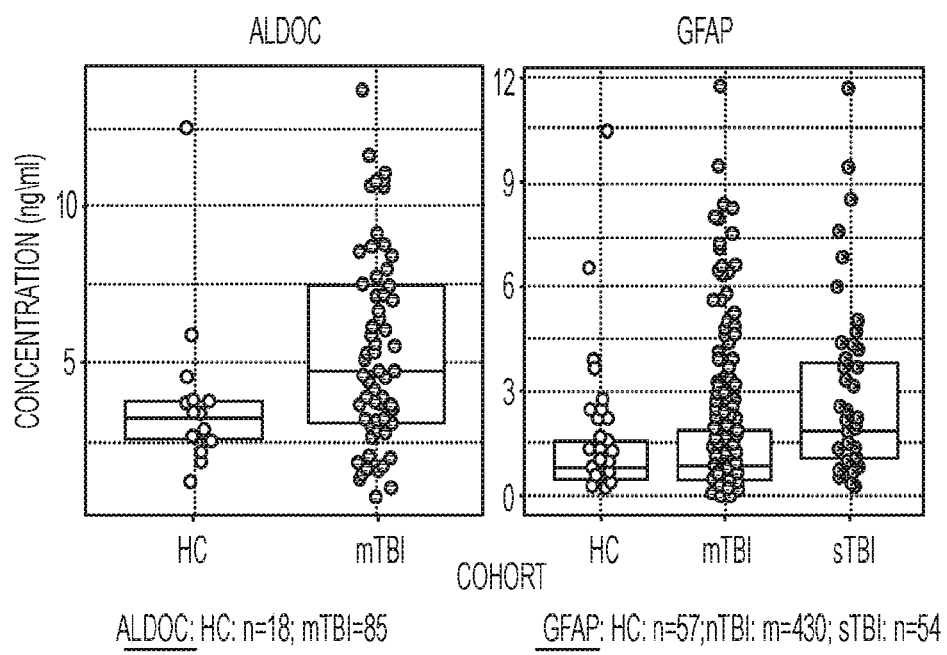
Figure 5B:
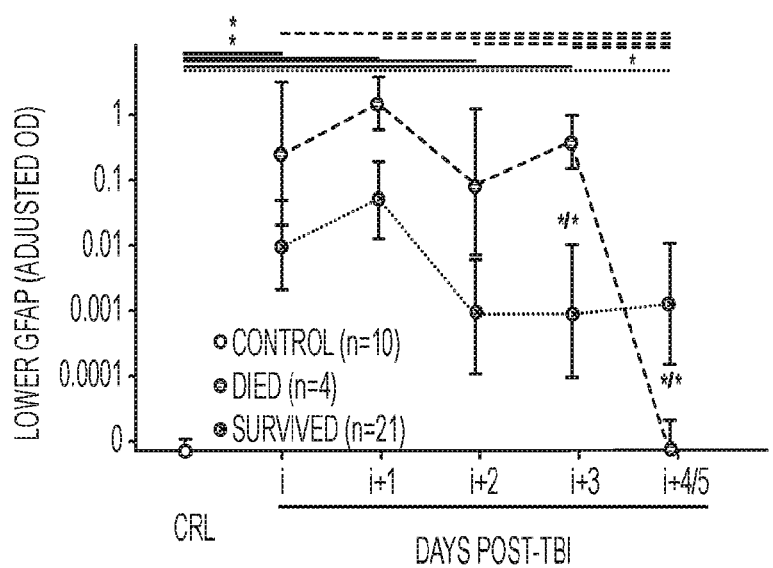
Figure 5C:
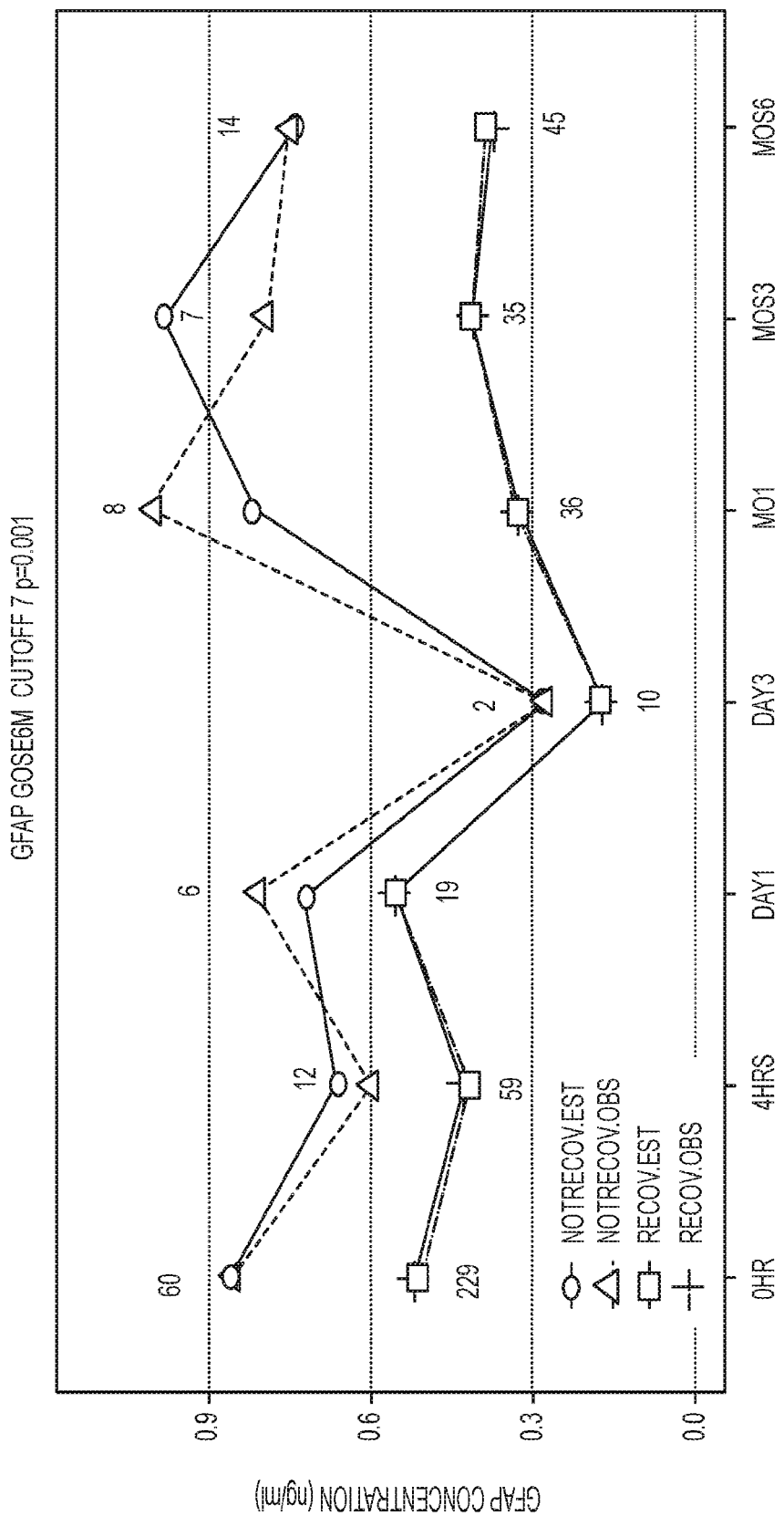

FIGS. 5A-5EA show box plots, graphs and a Spearman's correlation chart illustrating the distributions of ALDOC, GFAP and other biomarkers in serum obtained from patients with TBI and healthy controls (HC). FIG. 5A shows box plots depicting the results of sandwich ELISA analysis of ALDOC and GFAP in healthy controls and in subjects with mild or severe traumatic brain injury (TBI). Shown in the ALDOC (left plot) and GFAP (right plot) are protein biomarker concentrations in the serum of healthy controls (HC) and patients with mTBI. In the ALDOC panel (left plot), HC (healthy control), n=18; and mTBI (mild TBI), n=85. In the GFAP panel (right plot), HC, n=57; mTBI (mild TBI), n=430; and sTBI (severe TBI), n=54. Outliers were removed from the plots. FIG. 5B shows a graph of GFAP levels in patients who died (blue, n=4) or survived (red, n=21) relative to control (n–10) on the day of TBI injury (i), one day post-TBI injury (i+1), two days post-TBI injury (i+2); three days 3 post-TBI injury (i+3), or 4/5 days post-TBI injury (i+4/5). FIG. 5C shows a graph representing a longitudinal model for GFAP predicting good recovery by GOS-E (prediction of outcome based on models built with 500 patients with mTBI). Longitudinal linear mixed effects models were developed using serial sampling of 500 HeadSMART mild TBI patients and complete clinical information, developed on longitudinal biomarker level measurement by ImmunArray's MSD-ELISA, performed for 8 time point blood draws per patient, over a 6 month recovery period. Shown is GFAP concentration (ng/ml) versus various time points post injury for patients (estimated and observed) who had or had not recovered.

Figure 5D:
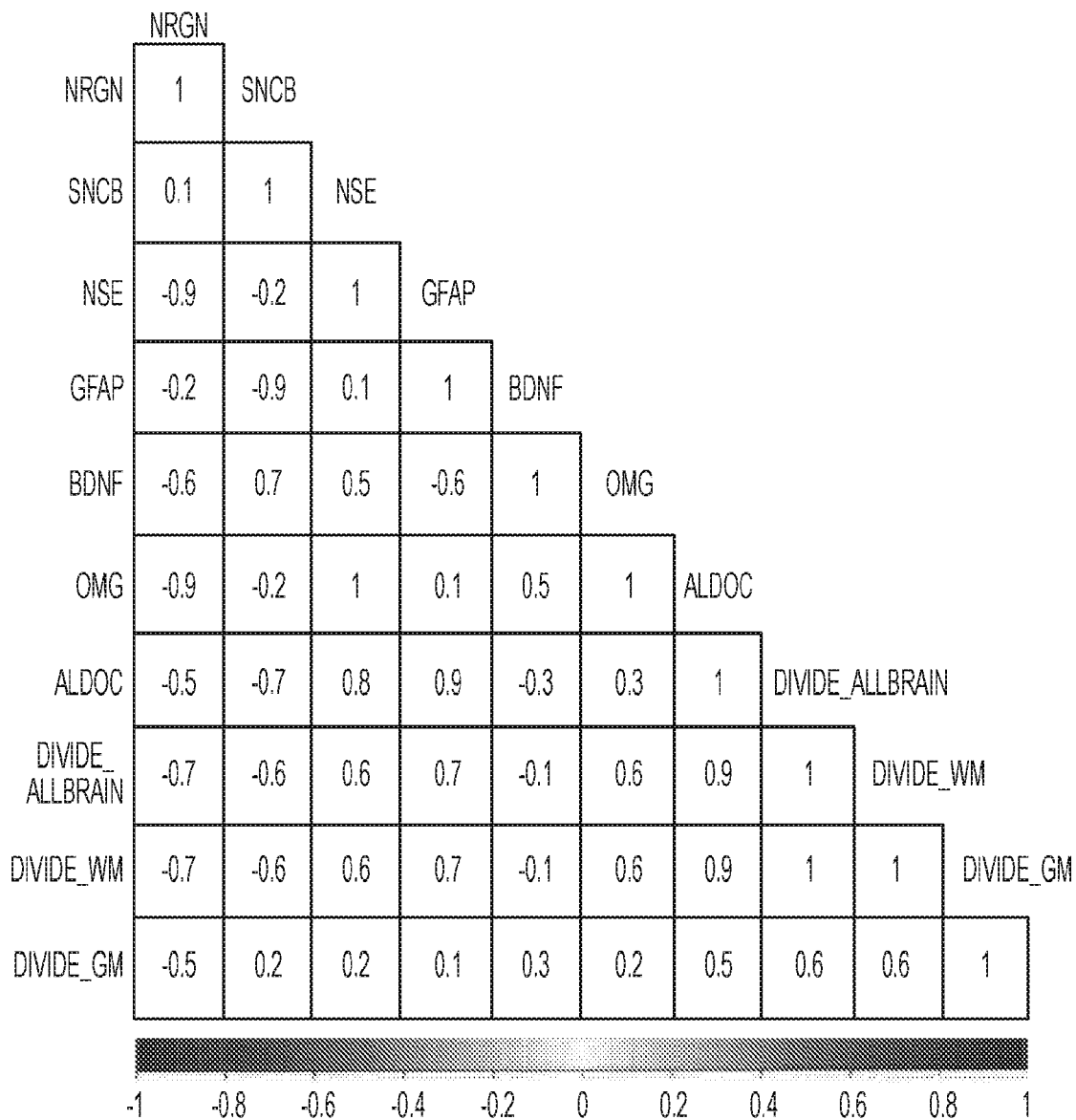
Figure 5D:
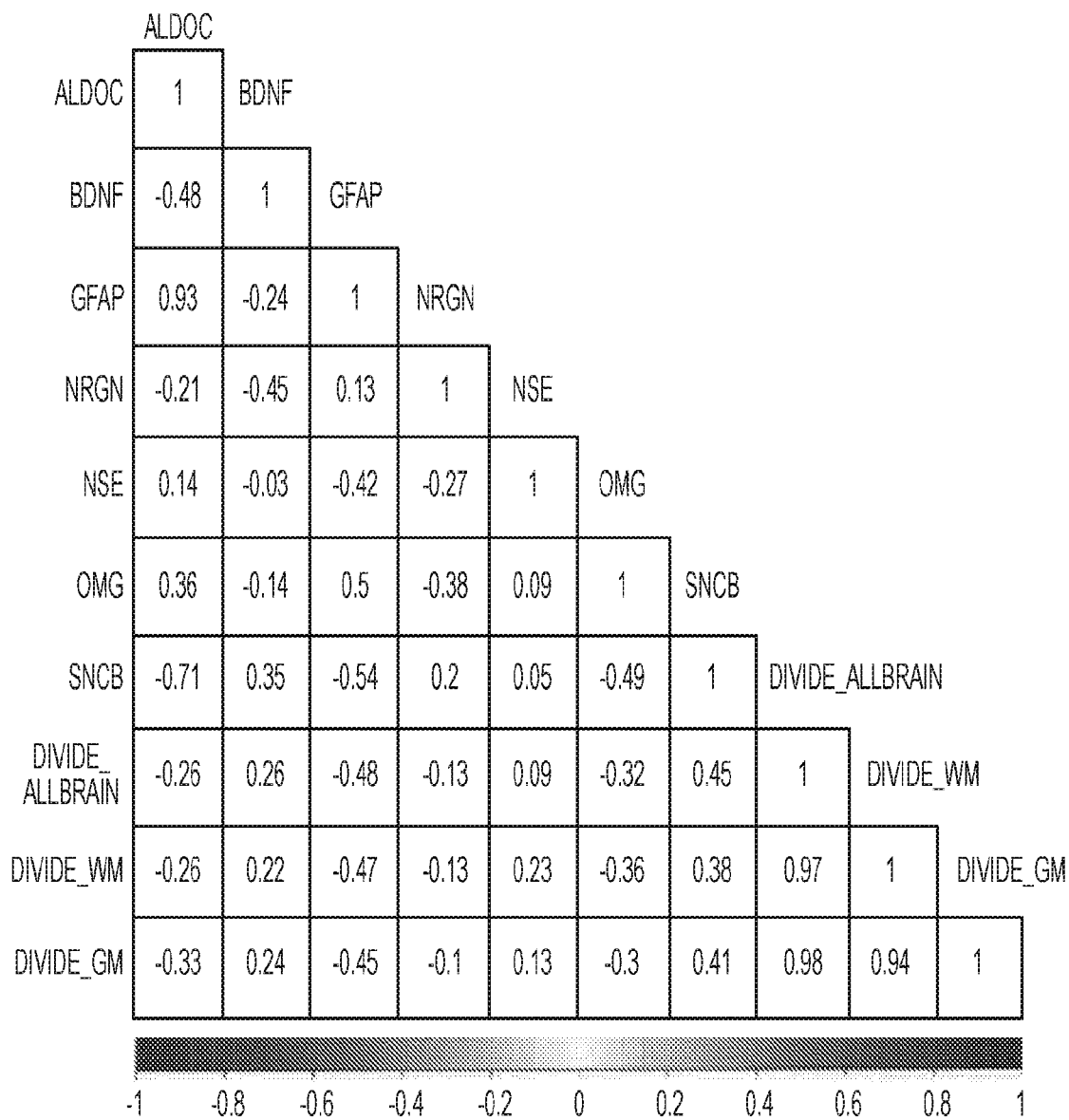
Figure 5E:
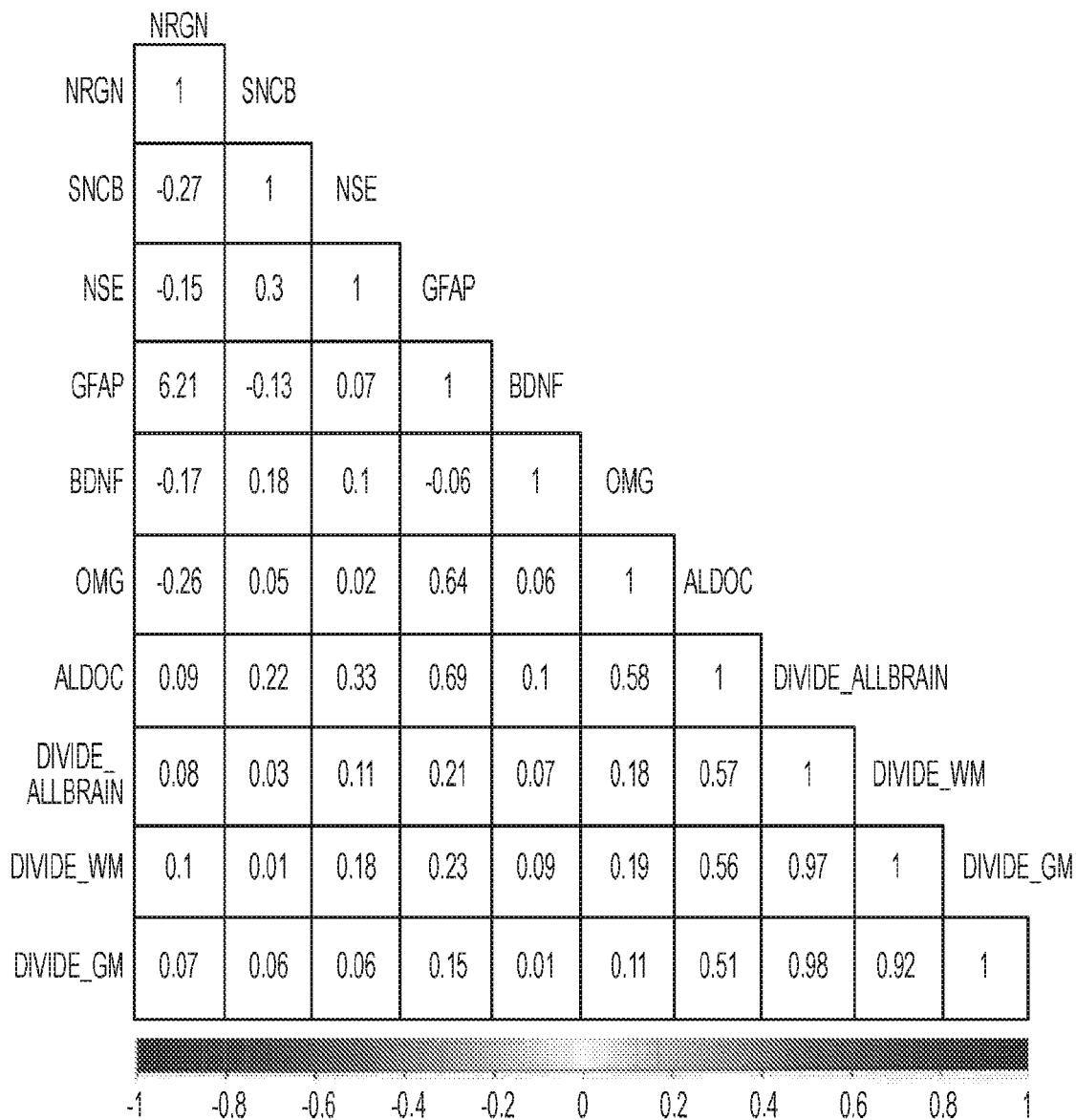
Figure 5E:
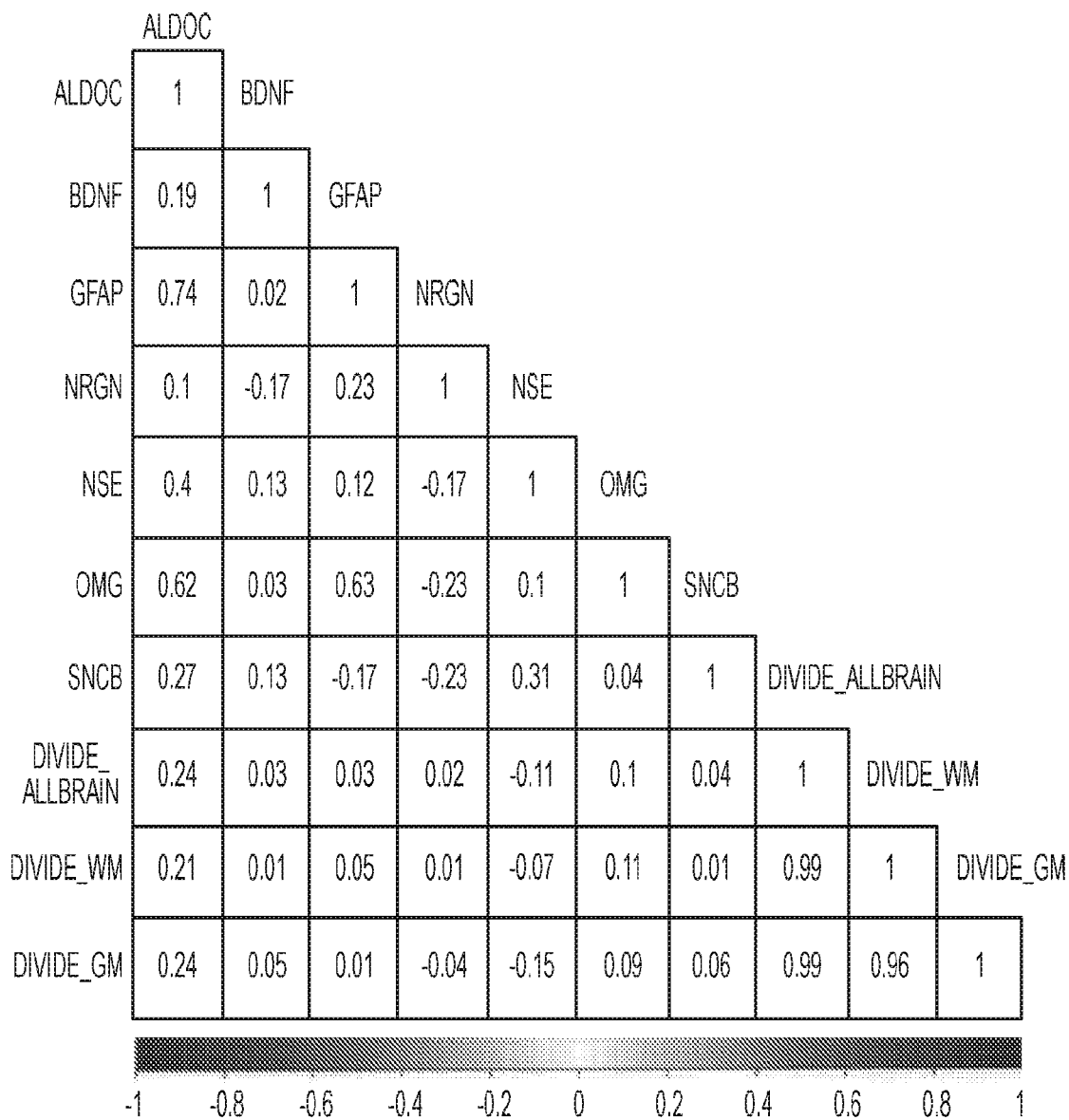

Similar to FIGS. 4F and 4G, FIGS. 5D, 5DA, 5E and 5EA present Spearman's pairwise correlation data of ALDOC, GFAP and other biomarkers relative to BBB permeability assessed by MRI analysis. FIG. 5D shows Spearman's pairwise correlation data related to blood-brain barrier (BBB) permeability changes and biomarker levels in ON season football players. MRI analysis was performed and blood samples were taken during the active athletic season in patients with mTBI and athletic controls, i.e., non-contact sports athlete controls. Shown are correlations of serum biomarker detection and MRI findings for BBB disruption. Spearman's coefficient (ρ) identifies relationships between biomarkers and brain volumes (voxels) of brain enhancement after MRI with gadolinium contrast agent to assess BBB leakage (vascular damage or leaking). Measurements for BBB leakage in total brain volume ("DIVIDE_Allbrain"), total white matter BBB leakage ("DIVIDE_WM"), or total gray matter ("DIVIDE_GM"), after normalization for local blood flow are shown. The results show strong positive correlations between ALDOC and GFAP serum protein levels (both proteins enriched in astrocytes lining blood vessels and maintaining the BBB); BDNF and SNCB (both markers decreased after injury, as in TBI); and strong correlation with BBB leakage volume in total brain and white matter, with moderate positive correlation with gray matter BBB leakage. Strong inverse correlations are shown for NRGN and NSE and OMG, and between GFAP and SNCB. FIG. 5DA is an addendum that represents a greater number of patients examined by the same assays, and thus is updated data, the distributions of which represent the subsequent data table updates. FIG. 5E shows Spearman's pairwise correlation data related to all athletes: Correlations in a larger athlete group, including on season and off season football players, as well as non-contact sport athlete controls. FIG. 5EA is an addendum that represents a greater number of patients examined by the same assays, and thus is updated data, the distributions of which represent the subsequent data table updates.

Figure 6A:
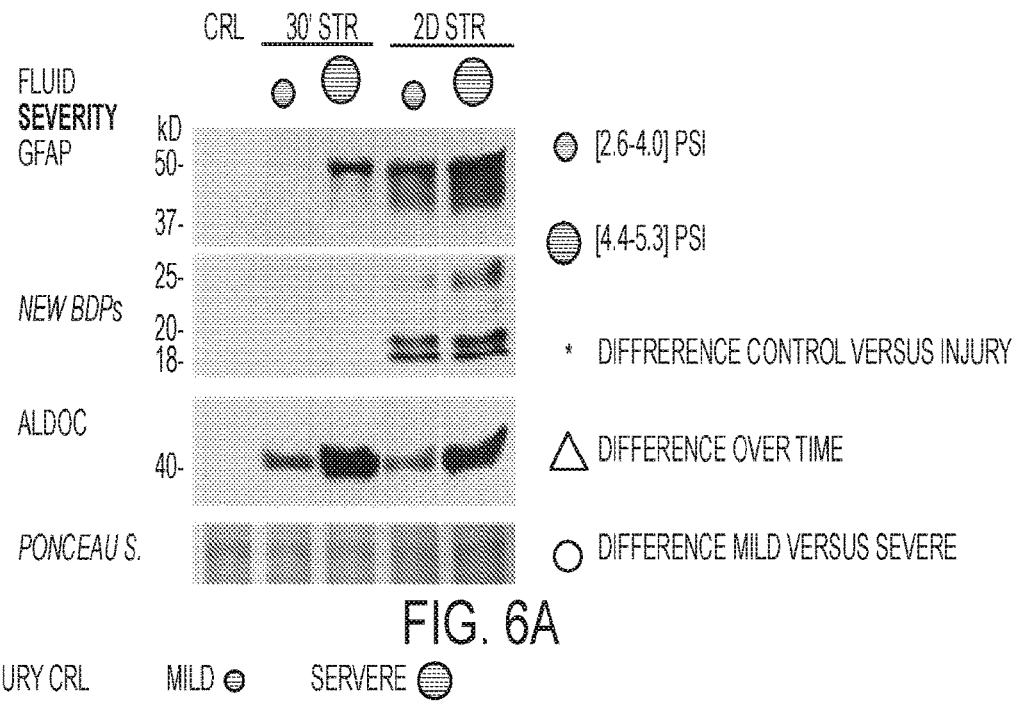
Figure 6B:
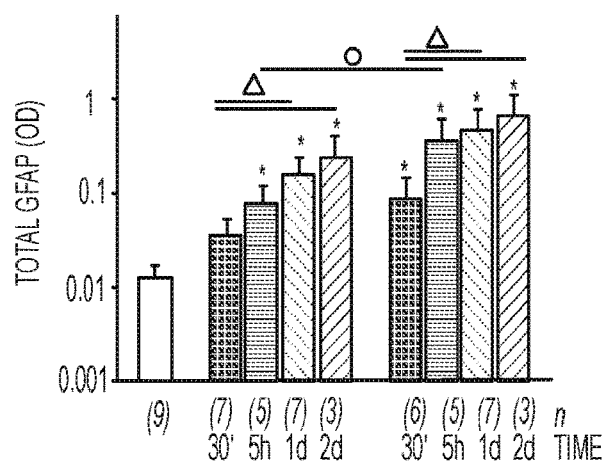
Figure 6C:
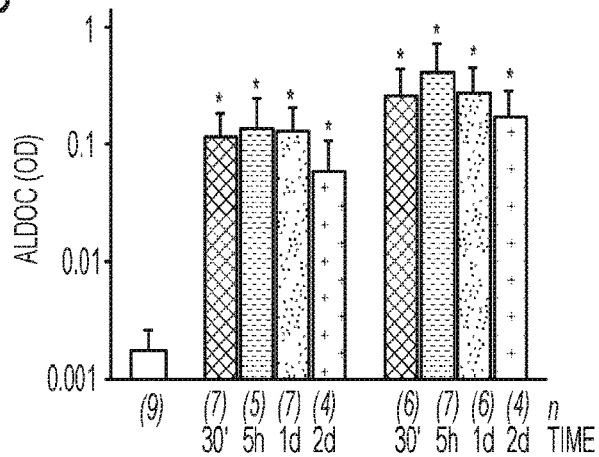
Figure 6D:
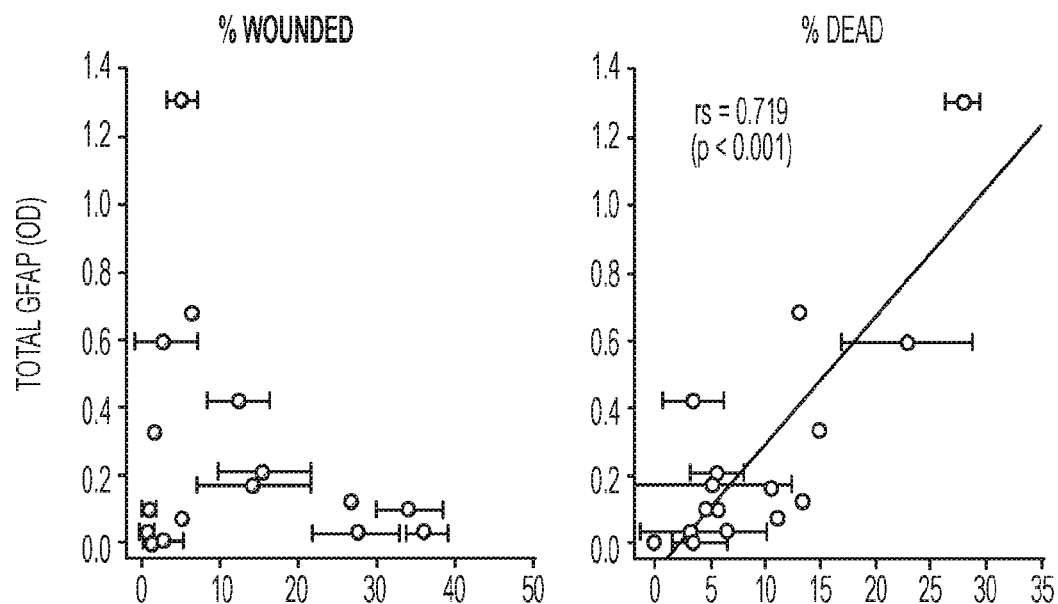
Figure 6E:
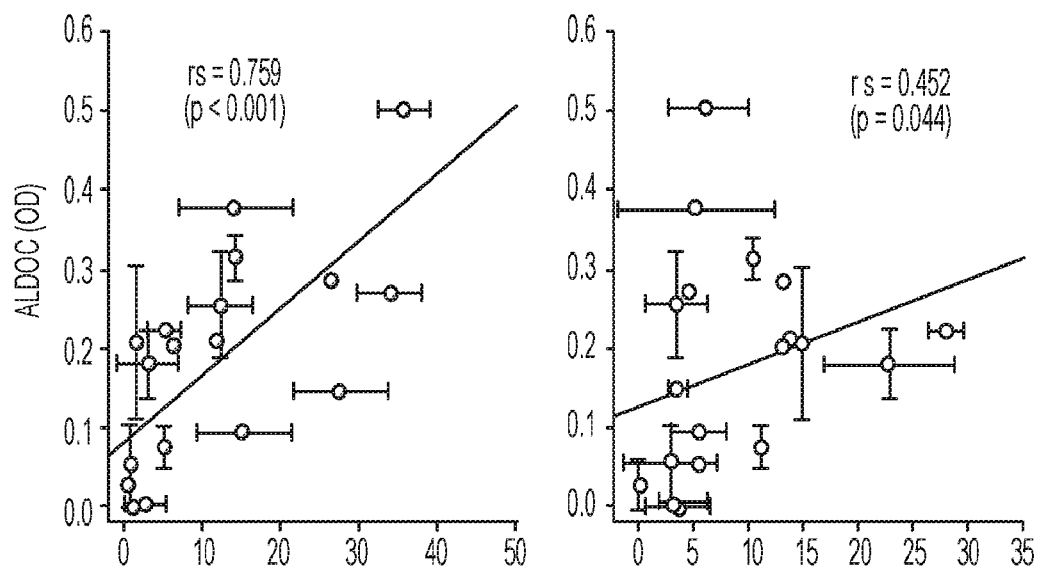
Figure 6F:
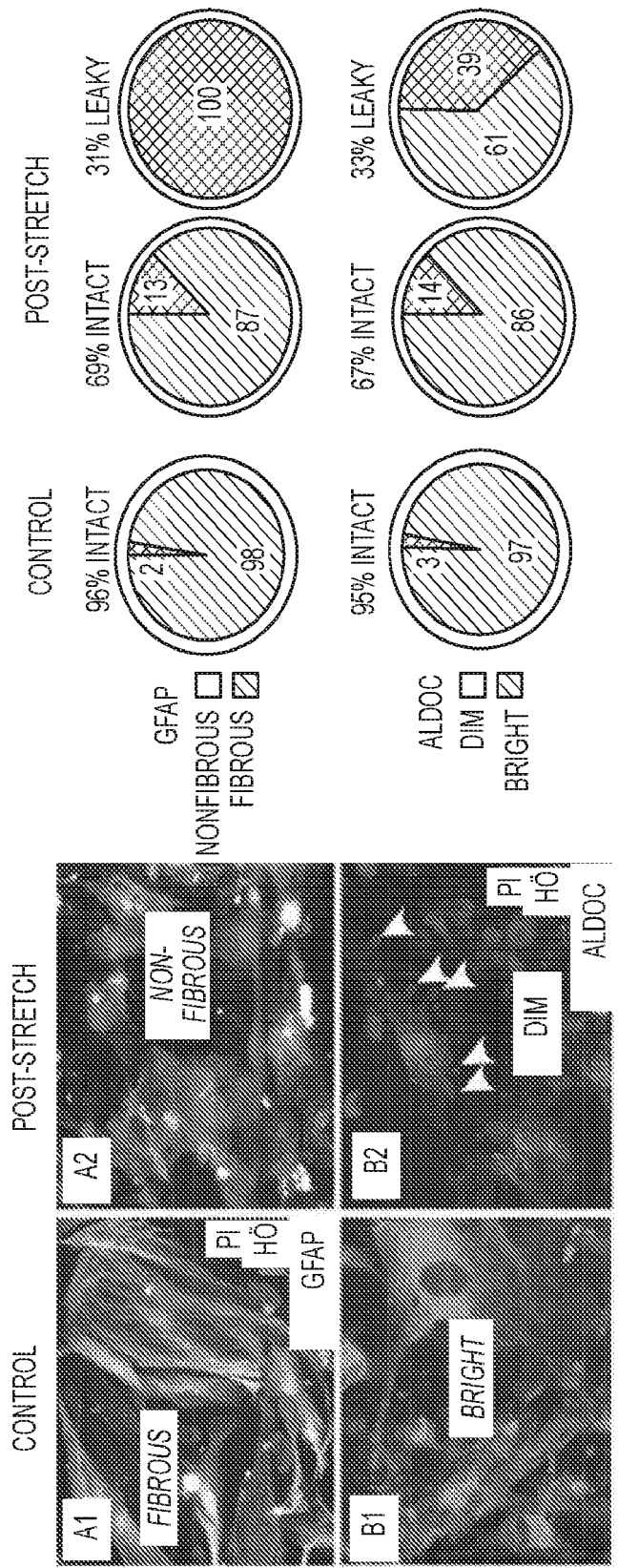

FIGS. 6A-6F present Western blot, bar graph, plots, micrograph images and diagrams illustrating that protein biomarker release was found to be associated with cell wounding and cell death (e.g., astroglial cells or astrocytes) in a human brain trauma model. FIG. 6A presents a Western blot analysis showing that ALDOC levels are detected relative to control after 30 minutes and after 2 days in fluid samples (e.g., released from astroglial cells, such as wounded or dead astroglial cells) after severe (sTBI) or less severe (mTBI) injury, while GFAP BDPs were not detected at 30 minutes following mild (mTBI) injury, but were detected after more severe (sTBI) injury and at a later time following either mTBI or sTBI. In addition, new, small GFAP BDPs were seen on day two following both mTBI and sTBI. FIGS. 6B and 6C show bar graphs of GFAP (FIG. 6B) and ALDOC (FIG. 6C) levels relative to control following mild or severe injury. While ALDOC levels show a more consistent presence early after injury and over time, GFAP (BDP) levels show an increased presence over time following injury (mTBI and sTBI). FIGS. 6D and 6E show plots of percent cell wounding and percent cell death and associated ALDOC or GFAP release from cells. FIG. 6F shows a photomicrographic image of cells (control versus post stretch, fibrous and nonfibrous) stained for GFAP or ALDOC, and the percentages of intact versus leaky cells associated with GFAP and ALDOC staining.

Figure 7A:
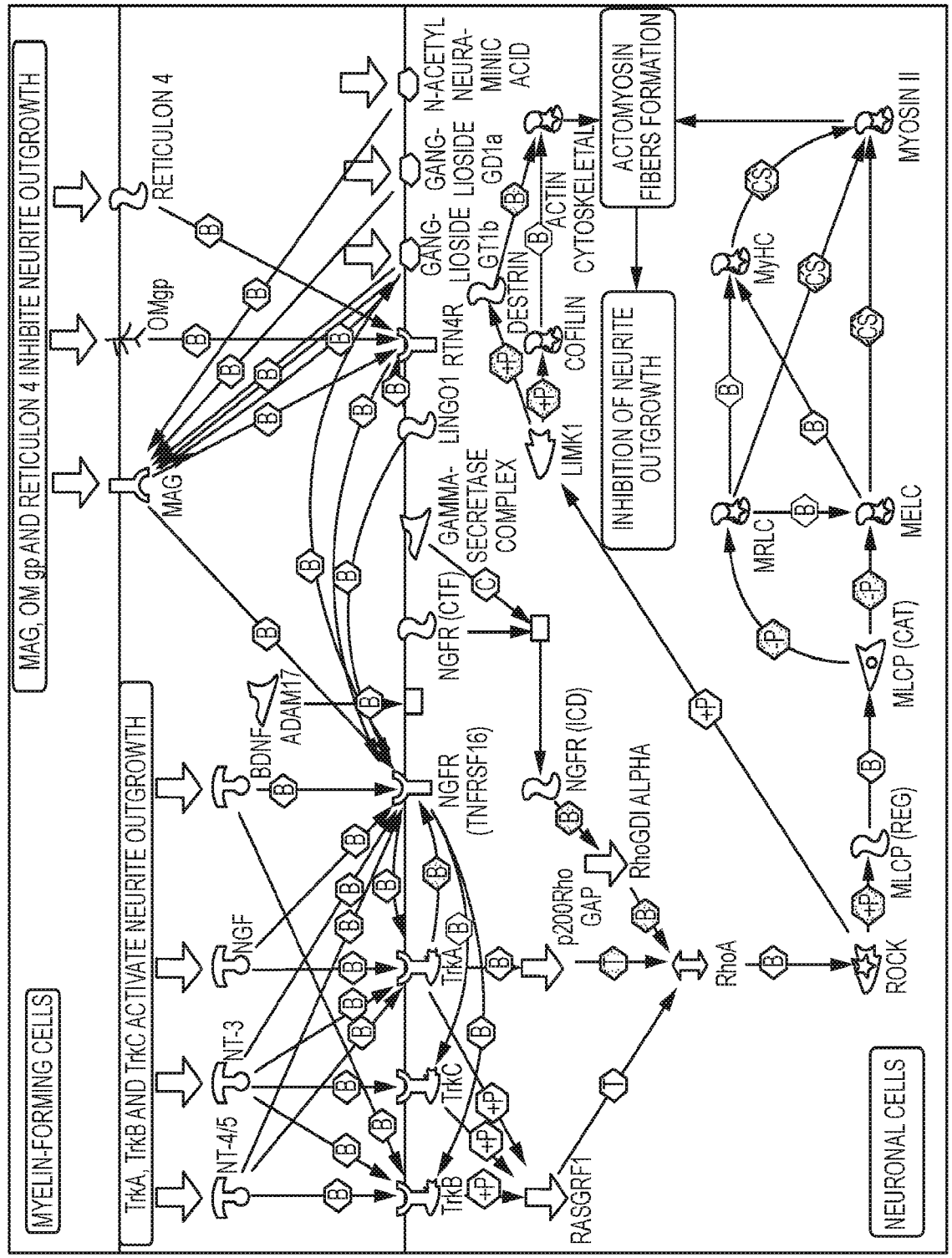
Figure 7B:
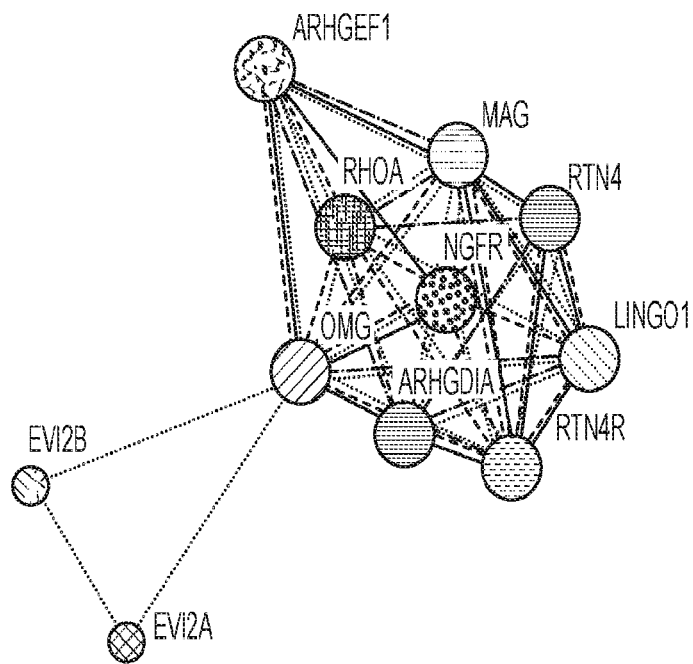

FIGS. 7A and 7B show schematics related to OMG in brain injury detection. FIG. 7A provides a reference chart highlighting functional aspects of OMG protein level. The interaction between OMG protein on oligodendrocyte processes that ensheath neuronal axons and the Reticulon-4 Receptor on neuronal membranes (RTN4R) are shown. (lsresearch.thomsonreuters.com/static/maps/735_map.png). FIG. 7B shows protein-protein interactions predicted using by STRING (Search Tool for the Retrieval of Interacting Genes/Proteins), a biological database and web resource of known and predicted protein-protein interactions. The STRING database is freely accessible, regularly updated and contains information from numerous sources, including experimental data, computational prediction methods and public text collections. As a resource STRING also highlights functional enrichments in user-provided lists of proteins, using a number of functional classification systems such as GO, Pfam and KEGG (Kyoto Encyclopedia of Genes and Genomes). The 10.0 version contains information about 9.6 million proteins from more than 2000 organisms. STRING has been developed by a consortium of academic institutions including Novo Nordisk Foundation Center for Protein Research (CPR), The European Molecular Biology Laboratory (EMBL), the University of Copenhagen (KU), the Swiss Institute of Bioinformatics (SIB), TU Dresden (TUD) and the University of Zurich (UZH). Protein-protein interaction networks are an integral component understanding cellular processes at the system level. Such networks can be used for filtering and assessing functional genomics data and for providing an intuitive platform for annotating structural, functional and evolutionary properties of proteins. Like many other databases that store protein association knowledge, STRING imports data from experimentally derived protein-protein interactions through literature curation. STRING also stores computationally predicted interactions from text mining of scientific texts; interactions computed from genomic features; and interactions transferred from model organisms based on orthology. All predicted or imported interactions are benchmarked against a common reference of functional partnership as annotated by KEGG.

Figure 8:
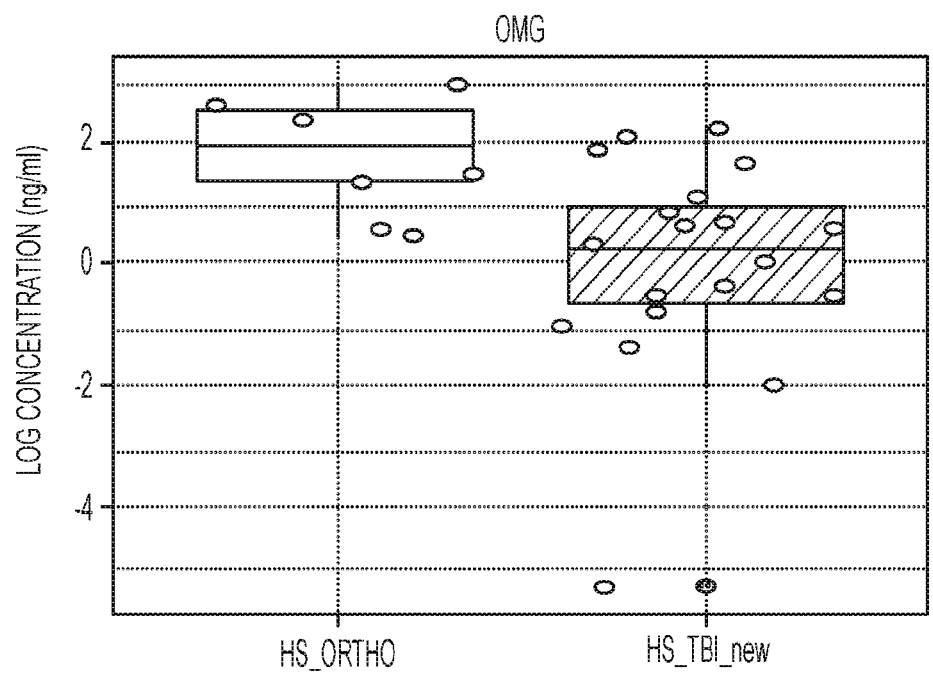

FIG. 8 provides a box plot showing a comparison of OMG levels in serum samples of individuals with no brain injury (trauma controls) versus those in serum samples from individuals with traumatic brain injury (TBI). In FIG. 8, orthopedic and non-TBI trauma injury patient serum samples (HS_Ortho) and traumatic brain injury (TBI) patient samples (HS_TBI_new) were collected in the HeadSMART study at Johns Hopkins University) as described in the above examples. ELISA assays (MSD ELISA) were performed for OMG. Results were compared to identify TBI related changes in OMG. Compared with non-TBI and orthopedic controls, individuals with traumatic brain injury showed decreased concentrations of OMG in their serum samples.

Figure 9:
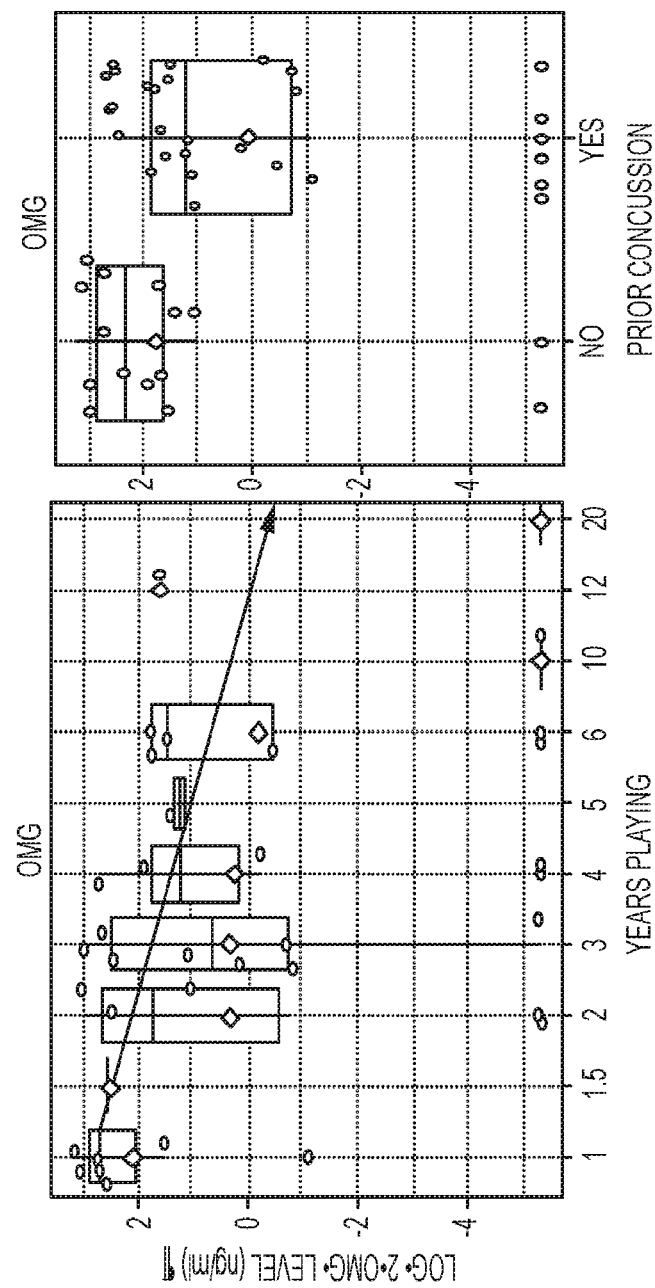

FIG. 9 provides box plots showing OMG levels in football players having over 20 years of active play. Both median (horizontal black line in each box) and mean (diamonds) OMG levels decreased with increasing years of football (FIG. 9, left panel) and also decreased in players with a history of prior concussion (FIG. 9, right panel). Athletes were recruited to the study at Ben Gurion University, Israel. The results demonstrate a decrease in detectable serum OMG levels in football players involved in over 20 years of active play.

FIGS. 10A-10G provide tables showing correlations between serum biomarker levels and MRI changes in specific fiber tracts in football players during the active season. (Example 5). The biomarker proteins correlated with MRI signal metrics indicating fiber tract damage include Neurogranin (NRGN), FIG. 10A; Synuclein Beta (SNCB), FIG. 10B; Neuron Specific Enolase (NSE), FIG. 10C; Glial Fibrillary Acidic Protein (GFAP), FIG. 10D; Brain Derived Neurotrophic Factor (BDNF), FIG. 10E; Oligodendrocyte Myelin Glycoprotein (OMG), FIG. 10F; and Aldolase C (ALDOC), FIG. 10G. A Key to the nomenclature in the table is presented beneath FIG. 10G.

FIGS. 11A-11E provide box plots and associated tables showing biomarker levels associated with CT scan findings of types of bleeding/hemorrhage.

Figure 12A:
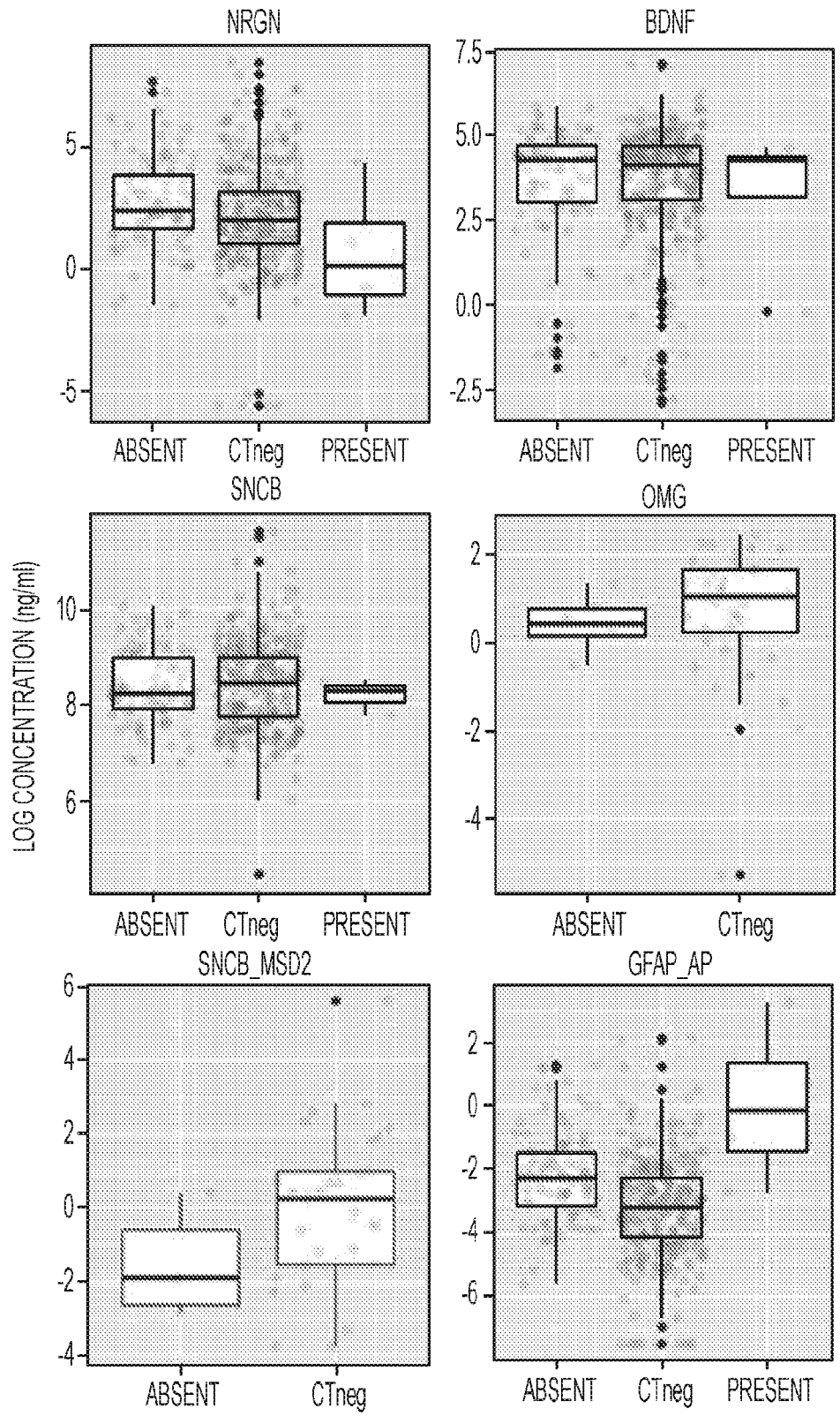
Figure 12A:
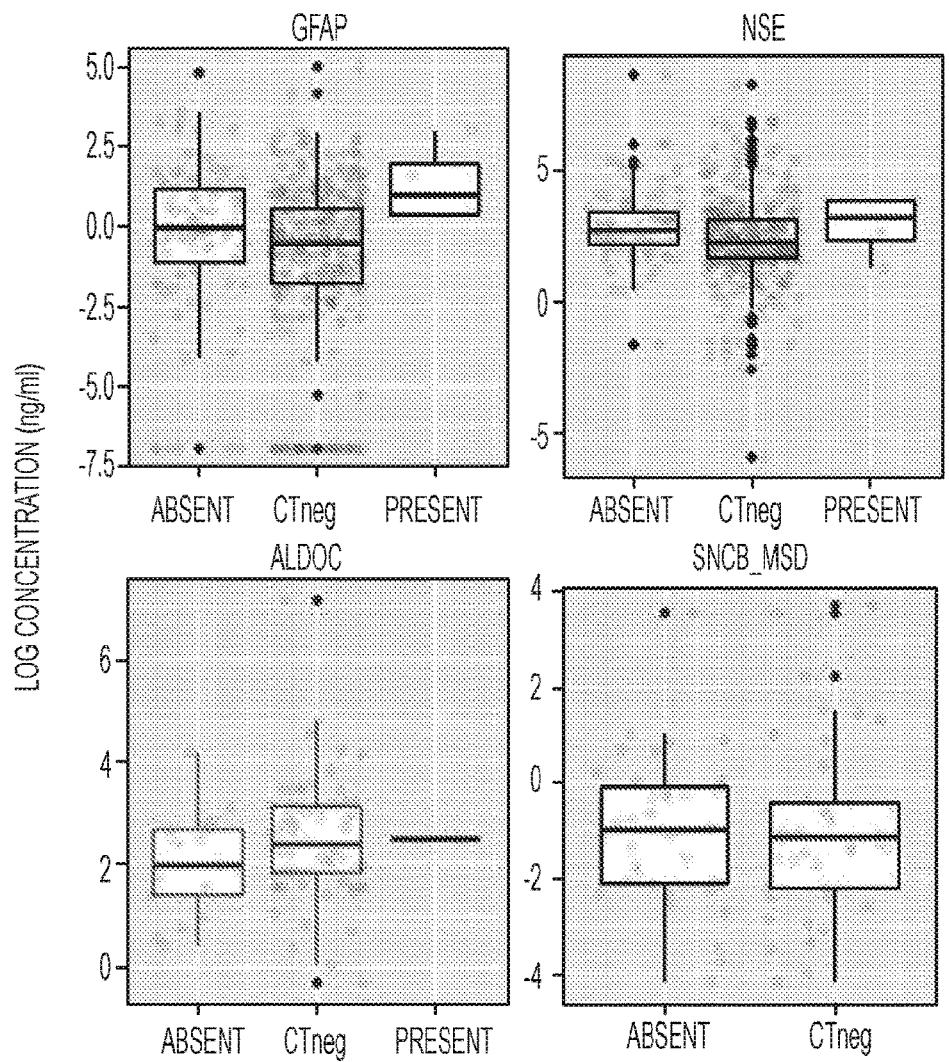
Figure 12B:
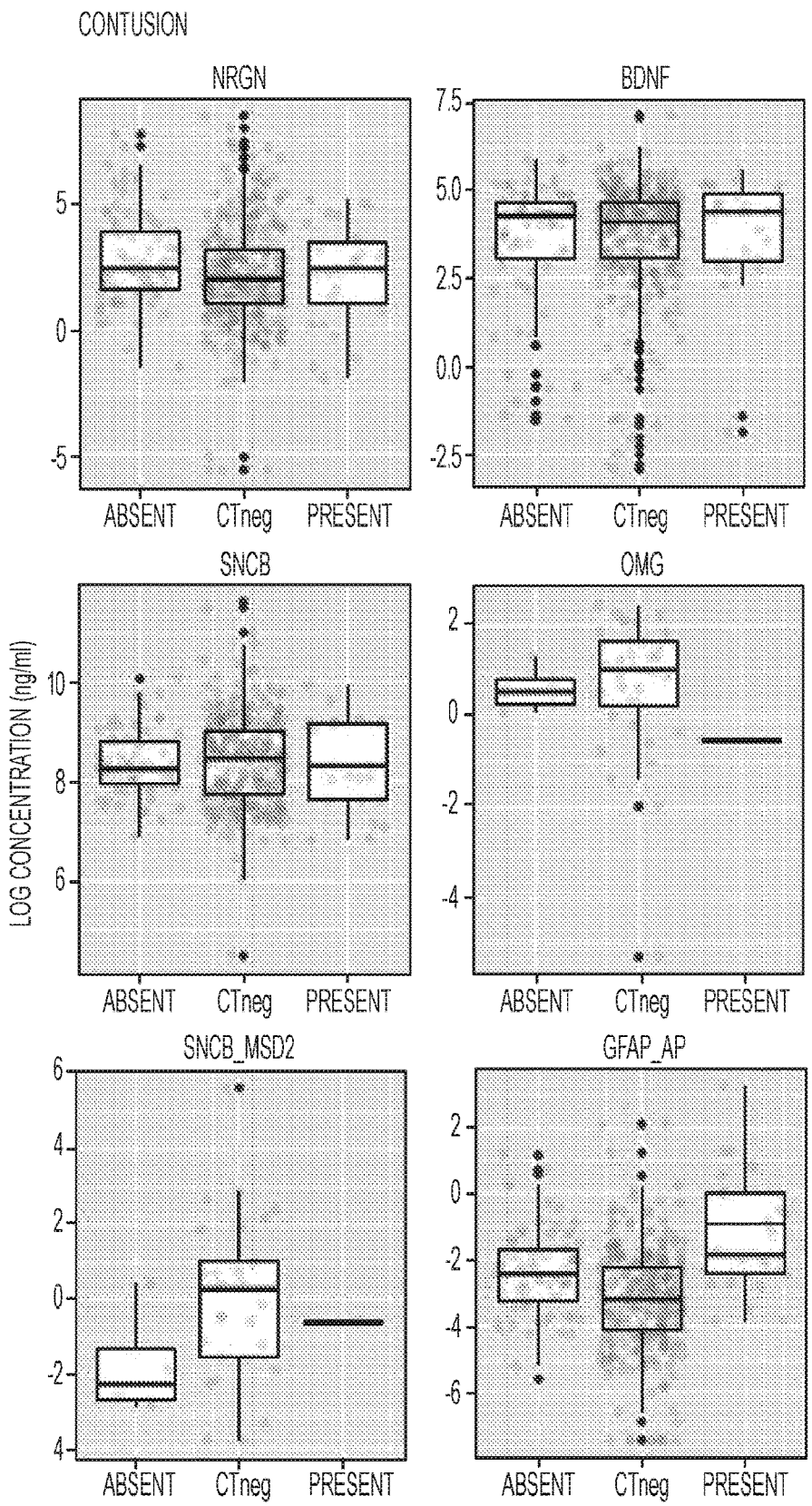
Figure 12B:
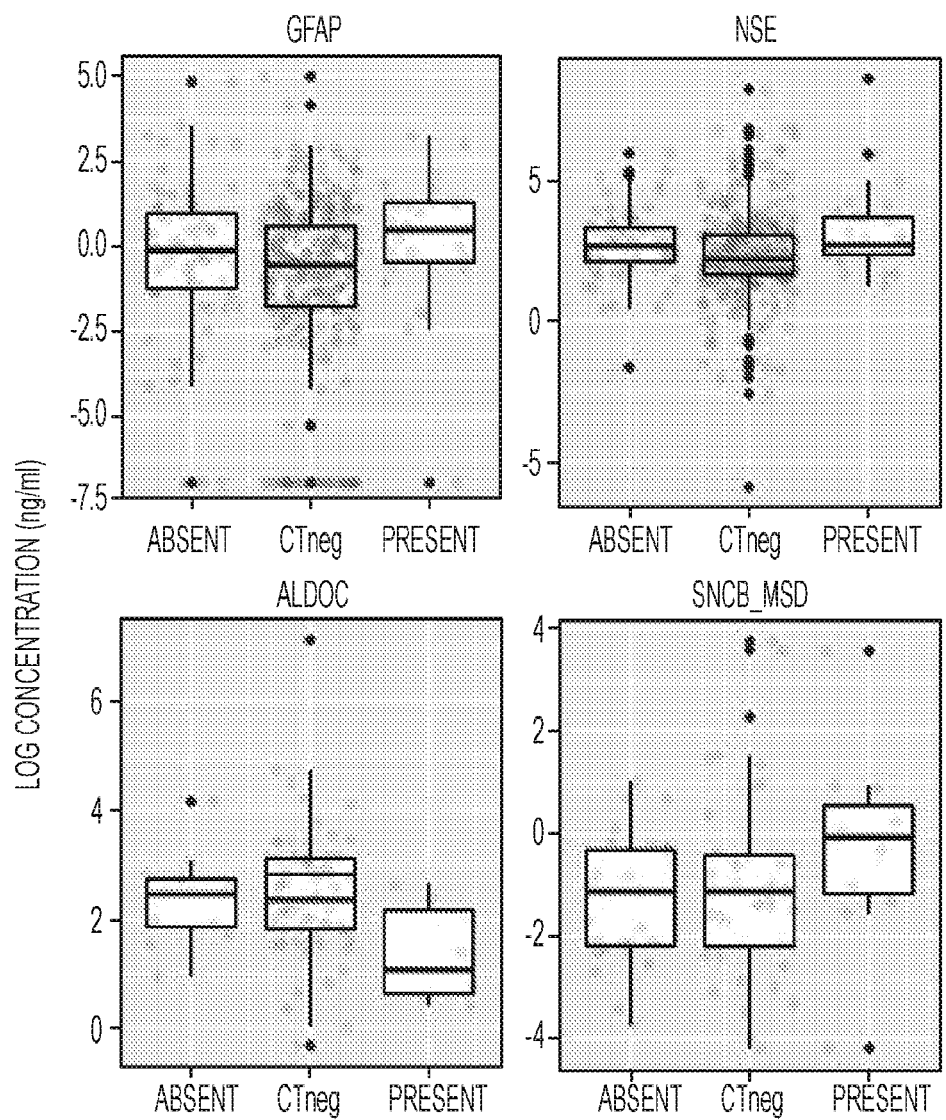

FIGS. 12A and 12B provide box plots and associated tables showing biomarker levels associated with non-hemorrhage CT scan findings.

DETAILED DESCRIPTION OF THE INVENTION

Traumatic brain injury (TBI) is an expanding global health concern, with mild TBI (mTBI) accounting for about 70-90% of all cases. Some proportion of those individuals with mTBI but not hospitalized may experience long-term problems, such as persistent headache, confusion, pain, fatigue, cognitive or memory problems, changes in sleep patterns, mood changes and/or sensory problems, such as changes in vision or hearing (post-concussion syndrome). Early mTBI symptoms may appear to be mild, but they can lead to significant, life-long impairment in an individual's ability to function physically, cognitively, and psychologically. Diagnosing mTBI can be challenging, because symptoms often are common to other medical problems, and onset of symptoms may occur days, weeks, or months after the initial injury. Although there are currently no standards for treatment and management of mTBI, appropriate detection, diagnosis, monitoring and treatment methods, such as those described herein, are critical for helping mTBI patients to achieve optimal recovery and to reduce or avoid significant adverse symptoms following injury.

The blood-brain barrier (BBB) is composed of a network of vessels that form a structural and chemical barrier between the brain and the vasculature or systemic circulation. BBB vessels are composed of specialized endothelial cells that lack fenestration, i.e., pores that allow rapid exchange of molecules between vessels and tissue. The BBB vessels also contain very few pinocytic vesicles, which minimizes the uptake of extracellular substances, and have extensive tight junctions that significantly restrict cell permeability. The limited cell permeability restricts movement of substances from the systemic circulation to the brain; this, in turn, buffers the brain from rapid changes in ionic or metabolic conditions. In addition, limited BBB permeability also protects the brain from exposure to molecules that are potentially toxic to neurons in the brain. A number of factors and cell types influence BBB permeability, for example, the extracellular matrix, neurons and non-neuronal cells, e.g., astrocytes, pericytes and vascular endothelial cells, all of which act coordinately to regulate BBB permeability and maintain the integrity and function of the central nervous system (CNS).

Under normal physiological conditions, BBB permeability is limited by the neurovascular system, which prevents the transport of bacteria and large (and most small) molecules into the brain. To enter the brain, a molecule must be lipid soluble, have a molecular weight of less than about 400 Daltons and must not be an active efflux transporter (AET) substrate. If a molecule does not have the foregoing characteristics, it can only pass the BBB if it is transported by a carrier-mediated transporter (CMT) or via receptor-mediated transport (RMT). Waste products and small molecules that cannot pass through the BBB can leave the BBB only as substrates of AET. Under certain conditions, e.g., inflammation, traumatic brain injury, mTBI, concussion, or ischemic stroke, the integrity of the BBB becomes compromised and allows passage of larger and hydrophilic substances, which changes or alters normal BBB permeability. This can lead to more serious repercussions in the brain, such as leakage from blood vessels, hemorrhage (intracranial hemorrhage), aneurysm, as well as symptoms of injury, e.g., headache, confusion, tinnitus, or memory, attention, concentration, or thinking problems.

According to some embodiments of the invention, blood, serum, or plasma biomarker protein levels (e.g., Aldolase C (ALDOC), and one or more of Brain Derived Neurotrophic Factor (BDNF), Glial Fibrillary Acidic Protein (GFAP), Neurogranin (NRGN), Neuron Specific Enolase (NSE), Oligodendrocyte Myelin Glycoprotein (OMG) and Synuclein Beta (SNCB)) can provide clinically useful information relevant to TBI, in particular, mTBI or concussion, particularly when evaluated in conjunction with neuroimaging analysis of a subject's brain to detect changes in vascular or BBB permeability in areas of the brain, for determining and identifying TBI, mTBI, or concussion in a subject, or for discriminating between subjects with mTBI or concussion and those without mTBI or concussion. According to some embodiments, blood, serum, or plasma biomarker protein levels GFAP, BDNF, NRGN, NSE, OMG, SNCB, MT3 and ICAM 5 or combinations thereof can provide clinically useful information relevant to TBI, particularly in TBI or concussion, and are useful in each of the methods of the invention. One or more biomarkers, selected from ALDOC, GFAP, BDNF, NRGN, NSE, OMG, SNCB, Intercellular Adhesion Molecule 5 (ICAM5) and Metallothionein 3 (MT3), for various brain injuries are have been described. See e.g., U.S. Pat. No. 9,746,481, U.S. Patent Application Publication Nos. 2016/0178643 and 2018/0024145, and International Patent Application Publication No. WO 2016/179426.

The glycolytic enzyme ALDOC is a brain-specific isoform that constitutes 1-2% of the brain protein mass. In embodiments, the biomarkers evaluated include the biomarker panels ALDOC and OMG; ALDOC, NRGN and OMG; ALDOC, BDNF and NSE; BDNF and SNCB; ALDOC, NRGN and BDNF; or GFAP, NRGN and BDNF. In embodiments, the biomarkers evaluated include the biomarker panels GFAP and OMG; GFAP, NRGN and OMG; GFAP, BDNF and NSE; or GFAP, NRGN and BDNF.

It will be understood that in accordance with the described methods, a finding of a change or alteration in BBB permeability upon neuroimaging analysis of areas of the brain by MRI (e.g., MRI with contrast or 3T MRI) reflects abnormality, pathology, or damage in an area of the BBB, for example, breakdown or leakage of a blood vessel or the blood vasculature in an area of the BBB. In addition, performing neuroimaging of the brain of a subject, in particular, using MRI analysis, more specifically, MRI with gadolinium contrast, or 3T MRI, or CT scan analysis, in conjunction with detection and measurement of the biomarkers as described herein, provides advantages for both the practitioner and the subject in the detection, diagnosis and treatment of brain injury and trauma, e.g., mTBI or concussion.

In an embodiment, a method is provided for assessing, diagnosing, or identifying whether a subject has sustained TBI, mTBI, or concussion, and in particular, mTBI or concussion, in which the level of the biomarker proteins ALDOC and one or more of Brain Derived Neurotrophic Factor (BDNF), Glial Fibrillary Acidic Protein (GFAP), Neurogranin (NRGN), Neuron Specific Enolase (NSE), Oligodendrocyte Myelin Glycoprotein (OMG) and Synuclein Beta (SNCB) is measured in the biologic sample of a subject relative to the levels in a control. If the biomarker level, e.g., ALDOC and/or GFAP, or biomarker subset levels, e.g., ALDOC, GFAP and OMG, ALDOC and OMG; ALDOC, NRGN and OMG; ALDOC, BDNF and NSE; BDNF and SNCB; ALDOC, NRGN and BDNF; or GFAP and OMG; GFAP, NRGN and OMG; GFAP, BDNF and NSE; or GFAP, NRGN and BDNF, is/are increased or decreased in the subject's sample relative to control levels as a result of the practice of the method, then the step of neuroimaging the brain of the subject by MRI (e.g., DCE-MRI) is optimally performed to determine if there is a change in vascular or BBB permeability in areas of the subject's brain. In an embodiment, the levels of ALDOC and OMG, GFAP and OMG; ALDOC and NSE; or GFAP and NSE are increased in the subject's sample relative to control levels, and neuroimaging is performed on the subject. The more granular level of analysis afforded by the step of neuroimaging the brain to detect potential sites of BBB damage or insult can better inform a medical practitioner as to whether the subject has sustained a change to BBB permeability or vascular damage in areas of the brain that is visualized upon neuroimaging analysis. In addition, neuroimaging analysis further allows the medical practitioner to understand those functional areas of the brain that may be at greater risk for undergoing exacerbated injury, such as risk of an aneurysm or more widespread hemorrhage, at a time subsequent to the subject's initial injury.

In certain embodiments, the methods provide both analysis of levels of biomarkers or a biomarker panel, as well as neuroimaging analysis of the brain to detect changes in vascular permeability as being indicative of mTBI or concussion in a subject, as well as the extent of damage or abnormality in BBB areas of the brain. While an increase or decrease in the levels of biomarkers affords a first level of detection or diagnosis of brain injury or trauma, such as mTBI or concussion, in a patient, neuroimaging analysis using advanced MRI techniques, or CT scanning analysis, allows for added, improved and more fine-tuned detection of more subtle or minor damage or pathology in BBB areas of the brain, such as minor hemorrhage, bleeding and the like, which may lead to greater risk for more serious brain injury or pathology, e.g., severe hemorrhage or aneurysm. Thus, the described methods allow the medical practitioner to make more reliable and accurate diagnosis of mTBI, concussion, or TBI and to determine an optimum treatment for the individual who is identified or diagnosed as having vascular or BBB permeability alterations in areas of the brain, in addition to biomarker levels that may be increased or decreased relative to the norm following brain injury.

The described methods further allow the medical practitioner to determine, based on a finding of changes in vascular permeability in areas of the brain, the best course of treatment, for example, if the detected change in vascular permeability is only minor, then the practitioner may make an informed decision to allow the damage to repair or resolve itself over time. In contrast, if the detected vascular permeability is more serious in nature (e.g., severe blood vessel leakage, hemorrhage and the like), then drug therapy or surgical intervention may be recommended or undertaken as treatment for the subject's mTBI. In an embodiment, the described methods can be repeated at predetermined time intervals following initial injury to monitor the status of injury in a subject who has been diagnosed or identified as having mTBI or concussion and in whom vascular permeability damage has been detected by neuroimaging analysis. Such monitoring of a given subject can inform the medical practitioner as to whether minor vascular permeability damage or alteration has progressed to a more major or serious condition at the time of subsequent assessment of the subject, and/or as to whether intervention, further intervention, a different treatment course, or maintenance of the same course of treatment is advisable for the subject. Moreover, use of the described methods to monitor the biomarker status and BBB permeability status of a subject who has been identified as having mTBI, for example, is also advantageous for assessing whether an area of BBB damage causing a change in vascular permeability as detected by the methods is healing or resolving properly. In some embodiments, the subject undergoing analysis by the practice of the described methods has sustained repetitive injury to the head and/or brain. In an embodiment, the subject is an athlete, in particular, an athlete who plays a contact sport.

In a particular embodiment, altered, e.g., elevated or decreased, levels of ALDOC and OMG; ALDOC, NRGN and OMG; ALDOC, BDNF and NSE; BDNF and SNCB; ALDOC, NRGN and BDNF; or GFAP and OMG; GFAP, NRGN and OMG; GFAP, BDNF and NSE; or GFAP, NRGN and BDNF protein biomarkers relative to control levels are detected in biofluid samples from subjects having mTBI or concussion. In an embodiment, elevated ALDOC and GFAP levels are highly correlated with areas of BBB damage and changes in vascular permeability in subjects having mTBI or concussion, as assessed by MRI techniques, more specifically, contrast MRI techniques (e.g., 3T MRI), or CT scan. In a particular embodiment, the subjects are athletes who play a contact sport, such as football, and the controls are normal healthy individuals (e.g., age and sex-matched) not having mTBI. In an embodiment, the biomarkers BDNF and SNCB also correlate with mTBI in subjects with mTBI (e.g., football players), and their levels are found to decrease in the subjects with mTBI relative to the levels of these proteins in healthy controls. In an embodiment, the correlation between elevated (or increased) levels of certain protein biomarkers and changes in vascular permeability of the BBB was high in individuals (e.g., athletes) who had prior histories of concussion. In an embodiment, the levels of a subset of biomarkers, including ALDOC, GFAP and OMG; and ALDOC, GFAP and NSE, are elevated in a biological sample of an individual with mTBI relative to control levels and correlate with changes in vascular permeability in the BBB as assessed by neuroimaging analysis (by 3T MRI or by CT scan) of the brain of the individual.

The described methods have broad applicability for diagnostics in athletes whose serum biomarker levels and neuroimaging analysis for detection of change in BBB vascular permeability may be used to determine whether the athlete has both altered biomarker levels and damage to the integrity of the BBB indicative of significant mTBI or concussion (may not return to play immediately) or has not had altered biomarker levels and has no change to the integrity of the BBB, indicating no significant mTBI or concussion (may return to play immediately). Similar determinations may be made in connection with an individual (e.g., non-athlete) returning or not returning to work.

For athletes, especially those who play contact sports, military personnel and other subjects suspected of sustaining mTBI or concussion, the current diagnostic paradigm is based on subjective patient report of symptoms and physical exam findings. As a result, the described methods provide a solution to the clinical need for diagnostic, evaluative, and assessment tests that can objectively and more meticulously determine that a subject has mTBI or concussion and discriminate TBI, mTBI or concussion among subjects who present with undifferentiated blunt head injuries.

Detection of Brain Injury Biomarkers
Detection by Immunoassay

In specific embodiments, the biomarkers of the invention can be detected and/or measured by immunoassay. Immunoassay requires biospecific capture reagents/binding agents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The invention contemplates traditional immunoassays including, for example, sandwich immunoassays including enzyme-linked immunosorbent assays (ELISA) or fluorescence-based immunoassays, such as fluorescence-linked immunosorbent assay (FLISA), immunoblots, Western Blots (WB), as well as other enzyme immunoassays. Nephelometry is an assay performed in liquid phase, in which antibodies are in solution. Binding of the antigen to the antibody results in changes in absorbance, which is a parameter measured in the immunoassay. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

In certain embodiments, the expression levels of the biomarkers employed herein are quantified by immunoassay, such as ELISA or FLISA technology. In specific embodiments, the levels of expression of the biomarkers are determined by contacting the biological sample with antibodies, or antigen binding fragments thereof, that selectively bind to the biomarkers; and detecting binding of the antibodies, or antigen binding fragments thereof, to the biomarkers. In certain embodiments, the binding agents employed in the disclosed methods and compositions are labeled with a detectable moiety.

For example, the level of a biomarker in a sample can be assayed by contacting the biological sample with an antibody, or antigen binding fragment thereof, that selectively binds to the target biomarker (referred to as a capture molecule or antibody or a binding agent), and detecting the binding of the antibody, or antigen-binding fragment thereof, to the biomarker. The detection can be performed using a second antibody to bind to the capture antibody complexed with its target biomarker. A target biomarker can be an entire protein, or a variant or modified form thereof. Kits for the detection of biomarkers as described herein can include pre-coated strip plates, biotinylated secondary antibody, standards, controls, buffers, streptavidin-horse radish peroxidase (HRP), tetramethyl benzidine (TMB), stop reagents, and detailed instructions for carrying out the tests including performing standards.

Embodiments of the invention also provide methods for diagnosing brain injury, e.g., mTBI or concussion, in a subject, wherein the levels of expression of the biomarkers in a biological sample are determined simultaneously. For example, in one embodiment, methods are provided that include: (a) contacting a biological sample obtained from the subject with a plurality of binding agents that selectively bind to a plurality of biomarkers disclosed herein for a period of time sufficient to form binding agent-biomarker complexes; (b) detecting binding of the binding agents to the plurality of biomarkers, thereby determining the levels of expression of the biomarkers in the biological sample; and (c) comparing the levels of expression of the plurality of biomarkers in the biological sample with predetermined threshold values, wherein levels of expression of at least one of the plurality of polypeptide biomarkers above or below the predetermined threshold values indicates, for example, brain injury in the subject. Examples of binding agents that can be effectively employed in such methods include, but are not limited to, antibodies or antigen-binding fragments thereof, aptamers, lectins and the like.

In a further aspect, embodiments of the invention provide compositions that can be employed in the disclosed methods. In certain embodiments, such compositions include a solid substrate and a plurality of binding agents immobilized on the substrate, wherein each of the binding agents is immobilized at a different, indexable, location on the substrate and the binding agents selectively bind to a plurality of biomarkers disclosed herein. In a specific embodiment, the locations are pre-determined. In one embodiment, the binding agents selectively bind to a plurality of biomarkers described herein. Binding agents that can be employed in such compositions include, but are not limited to, antibodies, or antigen-binding fragments thereof, aptamers, lectins and the like.

In a related aspect, methods for assessing brain injury, e.g., mTBI or concussion, in a subject are provided, such methods including: (a) contacting a biological sample obtained from the subject with a binding agent or a composition disclosed herein for a period of time sufficient to form binding agent-polypeptide biomarker complexes; (b) detecting binding of the plurality of binding agents to the plurality of polypeptide biomarkers, thereby determining the levels of expression of the plurality of polypeptide biomarkers in the biological sample; and (c) comparing the levels of expression of the plurality of polypeptide biomarkers in the biological sample with predetermined threshold values, wherein levels of expression of at least one of the plurality of polypeptide biomarkers above or below the predetermined threshold values indicates brain injury status in the subject.

In yet another aspect, embodiments of the invention provide compositions including a solid substrate and a plurality of polypeptide biomarkers disclosed herein immobilized on the substrate, wherein each of the polypeptide biomarkers is immobilized at a different, indexable, location on the substrate. In certain embodiments, the plurality of polypeptide biomarkers include ALDOC or GFAP and one or more of NRGN, OMG, BDNF, NSE, SNCB; ALDOC and OMG; ALDOC, NRGN and OMG; ALDOC, BDNF and NSE; BDNF and SNCB; ALDOC, NRGN and BDNF; GFAP and OMG; GFAP, NRGN and OMG; GFAP, BDNF and NSE; GFAP, NRGN and BDNF; or GFAP, NRGN and BDNF.

Although antibodies are useful because of their extensive characterization, any other suitable agent (e.g., a ligand molecule, a peptide, an aptamer, or a small organic molecule) that specifically binds a biomarker of the invention may be optionally used in place of the antibody in the above described immunoassays. For example, an aptamer that specifically binds a biomarker and/or one or more of its breakdown products might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

In specific embodiments, the assay performed on the biological sample can include contacting the biological sample with one or more capture agents (e.g., antibodies, peptides, aptamer, etc., combinations thereof) to form a biomarker capture agent complex. The complexes can then be detected and/or quantified. A subject can then be identified as having brain injury based on a comparison of the detected/quantified/measured levels of biomarkers to one or more reference controls as described herein.

In one method, a first, or capture, binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker (or to the bound capture antibody) is then used to detect binding of the polypeptide biomarker to the capture antibody. The detection antibody is preferably conjugated, either directly or indirectly, to a detectable moiety. Examples of detectable moieties that can be employed in such methods include, but are not limited to, chemiluminescent and luminescent agents; fluorophores such as fluorescein, rhodamine and eosin; radioisotopes; colorimetric agents; and enzyme-substrate labels, such as biotin.

In another embodiment, the assay is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

Solid phase substrates, or carriers, that can be effectively employed in such assays are well known to those of skill in the art and include, for example, 96 well microtiter plates, glass, paper, and microporous membranes constructed, for example, of nitrocellulose, nylon, polyvinylidene difluoride, polyester, cellulose acetate, mixed cellulose esters and polycarbonate. Suitable microporous membranes include, for example, those described in U.S. Patent Application Publication No. US 2010/0093557 A1. Methods for the automation of immunoassays are well known in the art and include, for example, those described in U.S. Pat. Nos. 5,885,530, 4,981,785, 6,159,750 and 5,358,691.

The presence of several different polypeptide biomarkers in a test sample can be detected simultaneously using a multiplex assay, such as a multiplex ELISA. Multiplex assays offer the advantages of high throughput, a small volume of sample being required, and the ability to detect different proteins across a board dynamic range of concentrations.

In certain embodiments, such methods employ an array, wherein multiple binding agents (for example capture antibodies) specific for multiple biomarkers are immobilized on a substrate, such as a membrane, with each capture agent being positioned at a specific, pre-determined, location on the substrate. Methods for performing assays employing such arrays include those described, for example, in US Patent Application Publication Nos. US 2010/0093557A1 and US 2010/0190656A1, the disclosures of which are hereby specifically incorporated by reference.

Multiplex arrays in several different formats based on the utilization of, for example, flow cytometry, chemiluminescence or electron-chemiluminescence technology, can be used. Flow cytometric multiplex arrays, also known as bead-based multiplex arrays, include the Cytometric Bead Array (CBA) system from BD Biosciences (Bedford, Mass.)

and multi-analyte profiling (xMAP®) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis.

In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate.

Detection by Mass Spectrometry

In one aspect, the biomarkers of the invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic co-elution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application the terms SRM and MRM or also SRM/MRM can be used interchangeably, since they both refer to the same mass spectrometer operating principle. As a matter of clarity, the term MRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method includes matrix assisted laser desorption/ionization time-of-flight (MALDI-TOF MS or MALDI-TOF). In another embodiment, method includes MALDI-TOF tandem mass spectrometry (MALDI-TOF MS/MS). In yet another embodiment, mass spectrometry can be combined with another appropriate method(s) as would be understood by one of ordinary skill in the art. For example, MALDI-TOF can be utilized with trypsin digestion and tandem mass spectrometry as described herein.

In an alternative embodiment, the mass spectrometric technique includes surface enhanced laser desorption and ionization or "SELDI," as described, for example, in U.S. Pat. Nos. 6,225,047 and 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes including energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that includes antibodies that bind the biomarkers, wash the resin to remove unbound material, elute the biomarkers from the resin and detect the eluted biomarkers by MALDI or by SELDI.

Detection by Electrochemiluminescent Assay

In several embodiments, the biomarker biomarkers of the invention may be detected by means of an electrochemiluminescent assay developed by Meso Scale Discovery (Gaithersburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. Nos. 7,497,997; 7,491,540; 7,288,410; 7,036,946; 7,052,861; 6,977,722; 6,919,173; 6,673,533; 6,413,783; 6,362,011; 6,319,670; 6,207,369; 6,140,045; 6,090,545; and 5,866,434. See also U.S. Patent Applications Publication No. 2009/0170121; No. 2009/006339; No. 2009/0065357; No. 2006/0172340; No. 2006/0019319; No. 2005/0142033;

No. 2005/0052646; No. 2004/0022677; No. 2003/0124572; No. 2003/0113713; No. 2003/0003460; No. 2002/0137234; No. 2002/0086335; and No. 2001/0021534.

Other Methods for Detecting Biomarkers

The biomarkers of the invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally include solid substrates and have a generally planar surface, to which a capture reagent (also called an adsorbent or affinity reagent) is attached. Frequently, the surface of a biochip includes a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremont, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. Nos. 6,537,749; 6,329,209; 6,225,047; 5,242,828; PCT International Publication No. WO 00/56934; and PCT International Publication No. WO 03/048768.

In a particular embodiment, the invention includes a microarray chip. More specifically, the chip includes a small wafer that carries a collection of binding agents bound to its surface in an orderly pattern, each binding agent occupying a specific position on the chip. The set of binding agents specifically bind to each of the one or more one or more of the biomarkers described herein. In particular embodiments, a few micro-liters of blood serum or plasma are dropped on the chip array. Biomarker proteins present in the tested specimen bind to the binding agents specifically recognized by them. Subtype and amount of bound mark is detected and quantified using, for example, a fluorescently-labeled secondary, subtype-specific antibody. In particular embodiments, an optical reader is used for bound biomarker detection and quantification. Thus, a system can include a chip array and an optical reader. In other embodiments, a chip is provided.

Determination of Brain Injury or Brain Injury Status in an Individual

The invention generally relates to the use of biomarkers to assess brain injury (or head injury), especially mTBI or concussion, in conjunction with neuroimaging analysis, in particular, MRI with gadolinium contrast, (e.g., using MRI (1.5T- or 3T MRI) to detect changes in vascular permeability, e.g., blood vessel leakage or hemorrhage, in the brain. More specifically, the biomarkers of the invention can be used in diagnostic tests along with BBB permeability assessment by neuroimaging analysis to determine, qualify, and/or assess brain injury, for example, to assess brain injury (e.g., mTBI or concussion), in an individual, subject or patient, presenting for the first time or having repetitive injury. More specifically, one or more biomarkers showing a high degree of correlation with a change in vascular permeability in a BBB area of the brain in mTBI or concussion, and thus, the level of which is particularly suitable for being detected in assessing mTBI or concussion brain injury, includes, but is not limited to, Aldolase-C (ALDOC), and Aldolase-C (ALDOC) and Glial Fibrillary Acidic Protein (GFAP). Other biomarkers whose levels correlate with change in BBB vascular permeability and can be detected in addition to the ALDOC and GFAP biomarker include one or more of Brain Derived Neurotrophic Factor (BDNF), Neurogranin (NRGN), Neuron Specific Enolase (NSE), Oligodendrocyte Myelin Glycoprotein (OMG) and Synuclein Beta (SNCB).

Biomarker Panels

The biomarkers of the invention can be used in panels of several biomarkers in diagnostic tests to assess, determine, evaluate and/or qualify (used interchangeably herein) mTBI or concussive brain injury in an individual (patient). By way of example, the biomarker panels may include one or more of Neurogranin (NRGN), Synuclein Beta (SNCB), Neuron Specific Enolase (NSE), Glial Fibrillary Acidic Protein (GFAP), Brain Derived Neurotrophic Factor (BDNF), Oligodendrocyte Myelin Glycoprotein (OMG), or Aldolase C (ALDOC); ALDOC and OMG; ALDOC, NRGN and OMG; ALDOC, BDNF and NSE; BDNF and SNCB; ALDOC, NRGN and BDNF; GFAP and OMG; GFAP, NRGN and OMG; GFAP, BDNF and NSE; GFAP, NRGN and BDNF; or GFAP, NRGN and BDNF. The phrase "brain injury status" includes any distinguishable manifestation of brain injury, as the case may be, e.g., mTBI or concussion, including not having brain injury. For example, brain injury status includes, without limitation, brain injury or non-injury in a patient, the stage or severity of brain injury, the progress of brain injury (e.g., progress of brain injury over time), or the effectiveness or response to treatment of brain injury (e.g., clinical follow up and surveillance of brain injury after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the invention may show a statistical difference in different brain injury statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers can be differentially present in UI (NC or non-brain injury) and brain injury, and, therefore, are useful in aiding in the determination of brain injury status. In certain embodiments, the biomarkers are measured in a patient sample using the methods described herein and compared, for example, to predefined biomarker levels/ratios and correlated to brain injury status. In particular embodiments, the measurement(s) may then be compared with a relevant diagnostic amount(s), cut-off(s), or multivariate model scores that distinguish a positive brain injury status from a negative brain injury status. The diagnostic amount(s) represents a measured amount of a biomarker(s) above which or below which a patient is classified as having a particular brain injury status. For example, if the biomarker(s) is/are up-regulated compared to normal, then a measured amount(s) above (or greater than) the diagnostic cutoff(s) provides an assessment of brain injury status. Alternatively, if the biomarker(s) is/are down-regulated, then a measured amount(s) at or below the diagnostic cutoff(s) provides an assessment of brain injury status. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different brain injury statuses, and drawing the cut-off to suit the desired levels of specificity and sensitivity.

In other embodiments, the relative or normalized amounts biomarkers to each other are useful in aiding in the determination of brain injury status. In certain embodiments, the biomarker ratios are indicative of diagnosis. In other embodiments, a biomarker ratio can be compared to another biomarker ratio in the same sample or to a set of biomarker ratios from a control or reference sample.

Furthermore, in certain embodiments, the values measured for markers of a biomarker panel are mathematically combined and the combined value is correlated to the underlying diagnostic question. Biomarker values may be combined by any appropriate state of the art mathematical method. Mathematical methods useful for correlating a marker combination to a brain injury status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. In one embodiment, the method used in correlating a biomarker combination of the invention, e.g. to assess brain injury, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF THE COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

Oligodendrocyte Myelin Glycoprotein (OMG)

Oligodendrocyte myelin glycoprotein (Gene name: OMGP, protein name: OMG, OMGp) is an oligodendrocyte-specific polypeptide molecule that localizes to the myelin sheath that wraps around neuronal axons. Oligodendrocytes damaged during brain injury and disease shed OMG protein from the cell membrane as part of the repair process, and thus OMG plays a role in central nervous system development during myelination. While axonal damage may cause decreased OMG levels through the loss of axonal myelin, such damage more likely includes an active dismantling process in which myelin proteins are removed from damaged axons, or through upregulation of the Reticulon 4 receptor (RTN4R), the receptor for OMG, the internalization of RTN4R, or another similar process by other cellular receptors that bind OMG. Any of these events could lead to a decrease in serum levels of OMG, as well as inhibition of neurite outgrowth. RTN4R mediates axonal growth inhibition and may play a role in regulating axonal regeneration and plasticity in the adult central nervous system. As described herein, OMG is a biomarker of brain injury, e.g., TBI, mTBI or concussion, detectable in a sample, e.g., a body fluid sample, alone or in combination with one or more of the other biomarkers of brain injury according to the invention.

Determining Risk of Brain Injury

In a specific embodiment, the invention provides methods for determining the risk of brain injury, such as mTBI, in a patient. Biomarker percentages, ratios, amounts or patterns are characteristic of various risk states, e.g., high, medium or low. The risk of brain injury is determined by measuring the relevant biomarkers and then either submitting them to a classification algorithm or comparing them with a reference amount, i.e., a predefined level or pattern of biomarkers that is associated with the particular risk level.

Determining Severity of Brain Injury

In other embodiments, the invention provides methods for determining the severity of brain injury, e.g., mTBI, in a patient. Each grade or stage of brain injury likely has a characteristic level of a biomarker or relative levels/ratios of a set of biomarkers (a pattern or ratio). The severity of brain injury is determined by measuring the relevant biomarkers and then either submitting them to a classification algorithm or comparing them with a reference amount, i.e., a predefined level or pattern of biomarkers that is associated with the particular stage. In embodiments, severity of brain injury, e.g., mTBI, is further determined by performing neuroimaging analysis to detect damage or insult to the BBB, such as a change in vascular permeability, such as, for example, blood vessel leakage or hemorrhage in areas of the brain. Neuroimaging analysis, e.g., using contrast MRI or 3T MRI, allows for the detection and visualization of more subtle or minor effects of a change in vascular or BBB permeability in areas of the brain, such as bleeding, hemorrhage, or other insult or damage to the integrity of the BBB.

Determining Brain Injury Prognosis

In one embodiment, the invention provides methods for determining the course of brain injury, e.g., mTBI or concussion, in a patient, e.g., a patient who has experienced repetitive injury. Brain injury course refers to changes in brain injury status over time, including brain injury progression (worsening) and brain injury regression (improvement). Over time, the level, amount, or relative level or amount (e.g., the pattern or ratio) of the biomarkers changes. For example, biomarker "X" may be increased with brain injury, while biomarker "Y" may be decreased with brain injury. Therefore, the trend of these biomarkers, either increased or decreased over time toward brain injury or recovery, indicates the course of the condition. Accordingly, this method involves measuring the level of one or more biomarkers in a patient at least two different time points, e.g., at a first time point and at a second time point, and comparing the change, if any. The course of brain injury is determined based on these comparisons. As described, measuring the level of one or more biomarkers in a biologic sample of a subject may be performed in combination with neuroimaging analysis of the brain of the subject to detect a change in vascular permeability, such as blood vessel leakage or damage in the BBB.

Patient Management

In certain embodiments of the methods of qualifying brain injury status, e.g., mTBI or concussion, the methods further include determining and/or managing patient treatment based on the status. Such management includes the decisions and actions of the medical practitioner, physician, or clinician subsequent to determining brain injury status, mTBI or concussion. For example, if a physician makes a diagnosis of TBI, mTBI or concussion, then a certain monitoring regimen would follow. An assessment of the course of brain injury using the methods of the invention may then require a certain therapy regimen. Alternatively, a diagnosis of no brain injury might be followed with further testing or monitoring. Also, further tests may be called for if the diagnostic test gives an inconclusive result for brain injury status.

Performing neuroimaging analysis to determine changes in vascular permeability in BBB areas, after detecting changes in levels of biomarkers, or biomarker panels, e.g., changes in levels of at least one or at least two of the biomarkers or biomarker panels that indicate mTBI or concussion as described herein, e.g., ALDOC and OMG; ALDOC, NRGN and OMG; ALDOC, BDNF and NSE; BDNF and SNCB; ALDOC, NRGN and BDNF; BDNF and SNCB; BDNF, NRGN and SNCB; GFAP and OMG; GFAP, NRGN and OMG; GFAP, BDNF and NSE; or GFAP, NRGN and BDNF, can also better inform the treatment or therapy that a patient receives after injury (or during recovery). If change to the BBB vasculature is minor or does not exist, for example, little to no bleeding or blood vessel leakage is determined upon neuroimaging analysis, the injury may be allowed to resolve itself. If, however, more severe changes to brain vasculature are found and the BBB integrity is damaged, or severe bleeding or hemorrhage has occurred, surgical intervention (to relieve swelling or prevent bleeding) or treatment with drugs or medication may be deemed to be warranted. Nonlimiting examples of medications that may be administered for a condition of more serious TBI or mTBI include corticosteroids, diuretics to reduce swelling, painkillers, antianxiety medications, anticonvulsants to control the possibility of seizures, as well as anti-angiogenic drugs, such as agents that reduce endothelial cell vascular endothelial growth factor (VEGF) production or stimulation.

Determining Therapeutic Efficacy of Pharmaceutical Drug

In another embodiment, the invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern, profile or ratio) of one or more of the biomarkers of the invention may change toward a brain injury status profile, such as mTBI or concussion. Therefore, one can follow the course of one or more biomarkers in the patient during the course of treatment. In addition, one can follow BBB permeability status by neuroimaging of the brain via contrast MRI during the course of treatment. Accordingly, this method involves measuring one or more biomarkers in a patient receiving drug therapy, and correlating the biomarker levels/ratios with the brain injury status of the patient (e.g., by comparison to predefined levels/ratios of the biomarkers that correspond to different brain injury statuses). An embodiment of this method further involves determining changes in vascular permeability in the subject's BBB areas by neuroimaging analysis, if the biomarker levels/ratios correlate with a diagnosis of brain injury, e.g., mTBI or concussion. An embodiment of this method involves determining the levels/ratios of one or more biomarkers for at least two different time points during a course of drug therapy, e.g., a first time and a second time, and comparing the change in levels/ratios of the biomarkers, if any. For example, the levels/ratios of one or more biomarkers can be measured before and after drug administration or at two different time points during drug administration. The effect of therapy is determined based on these comparisons. If a treatment is effective, then the level/ratio of one or more biomarkers will trend toward normal, while if treatment is ineffective, the level/ratio of one or more biomarkers will trend toward a particular brain injury status. In a similar manner, if a treatment is effective, the neuroimaging analysis will show improvement in or resolution of vascular permeability status in the BBB, such as, for example, a significant reduction in bleeding or hemorrhage or the absence thereof in the affected brain areas.

Generation of Classification Algorithms for Qualifying Brain Injury Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may include raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., brain injury versus no brain injury).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application Publication No. 2002/0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

Kits for the Detection of Biomarkers

In another aspect, embodiments of the invention provide kits for qualifying brain injury status, e.g., qualifying mTBI or concussion, which kits are used to detect the biomarkers described herein. In a specific embodiment, the kit is provided as an ELISA kit including antibodies, or an antigen binding fragment thereof, that bind to the biomarkers of the invention including, but not limited to, Aldolase-C (ALDOC), Brain-derived neurotrophic factor (BDNF), Glial Fibrillary Acidic Protein (GFAP), Neurogranin (NRGN), Neuron Specific Enolase (NSE), Oligodendrocyte Myelin glycoprotein (OMG) and Synuclein Beta (SNCB) and combinations thereof. In particular embodiments, the kit includes an antibody or an antigen binding fragment thereof that binds to the ALDOC and OMG; ALDOC, NRGN and OMG; ALDOC, BDNF and NSE; BDNF and SNCB; ALDOC, NRGN and BDNF; or GFAP and OMG; GFAP, NRGN and OMG; GFAP, BDNF and NSE; or GFAP, NRGN and BDNF biomarkers. In a particular embodiment, the kit includes antibodies or antigen binding fragments thereof that bind to the biomarkers ALDOC, BDNF, GFAP, OMG, NSE and SNCB. In a particular embodiment, the kit includes antibodies or antigen binding fragments thereof that bind to the biomarkers ALDOC, NRGN and OMG. In a particular embodiment, the kit includes antibodies or antigen binding fragments thereof that bind to the biomarkers ALDOC, BDNF and NSE. In a particular embodiment, the kit includes antibodies or antigen binding fragments thereof that bind to the biomarkers BDNF and SNCB. In a particular embodiment, the kit includes antibodies or antigen binding fragments thereof that bind to the biomarkers GFAP and NSE. In a particular embodiment, the kit includes antibodies or antigen binding fragments thereof that bind to the biomarkers GFAP and NRGN.

The kit may be an ELISA or FLISA kit and include a solid support, such as a chip, microtiter plate (e.g., a 96-well plate), bead, or resin having biomarker capture reagents attached thereon. The kit may further include a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit may be provided as an immuno-chromatography strip including a membrane on which the antibodies are immobilized, and a means for detecting, e.g., gold particle bound antibodies, where the membrane, includes NC membrane and PVDF membrane. The kit may include a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

In certain embodiments, a patient can be diagnosed by adding to the kit a biological sample (e.g., blood or serum) obtained from the patient and detecting the relevant biomarkers conjugated with antibodies, specifically, by a method which includes the steps of: (i) collecting blood or serum from the patient; (ii) adding the blood or serum from patient to a diagnostic kit; and, (iii) detecting the biomarkers conjugated with antibodies. In this method, the antibodies are brought into contact with the patient's blood or serum. If the biomarkers are present in the sample, the antibodies or antigen binding fragments thereof will bind to the sample, or a portion thereof. In other kit and diagnostic embodiments, blood or serum is not collected from the patient (i.e., it is already collected). Moreover, in other embodiments, the sample may include a tissue sample or a clinical sample.

The kit can also include a washing solution or instructions for making a washing solution, in which the combination of the capture reagents and the washing solution allows capture of the biomarkers on the solid support for subsequent detection by, e.g., antibodies or mass spectrometry. In a further embodiment, a kit can include instructions for suitable operational parameters in the form of a label or separate insert. For example, the instructions may inform a consumer about how to collect the sample, how to wash the probe or the particular biomarkers to be detected, etc. In yet another embodiment, the kit can include one or more containers with biomarker samples, to be used as standard(s) for calibration or normalization.

The practice of the invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

Without further elaboration, it is believed that one skilled in the art, using the preceding description, can utilize the invention to the fullest extent. The following examples are illustrative only, and not limiting of the remainder of the disclosure or claims in any way whatsoever. In addition, the examples are put forth so as to provide those of ordinary skill in the art with a complete disclosure, description and exemplification of how to make and use the assay, screening, assessing, monitoring and therapeutic methods of the invention, and are not intended to limit the scope of what the inventors regard as their invention.

EXAMPLES

In the following examples, efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Methods

Samples:
Biomarker assays were performed on 4 separate cohorts of TBI patients from several collaborating centers, along with athletic controls. All studies were conducted under IRB-approved study protocols at each respective institution. HeadSMART, a prospective study being conducted at Johns Hopkins University, was the largest TBI cohort used in the study. From 500 TBI patients, a smaller number of age-matched male patients was studied for comparisons with athletic samples (males, aged 18-40; n=90). Median baseline blood draw was 4.2 hours from injury. Mild TBI sera from the University of Messina, Italy were analyzed (n=15, average age 58 years, 60% male). NCAA collegiate football players of the Laureate Institute for Brain Injury (LIBR, Univ. of Tulsa, Okla.) were enrolled (average age 20-21 years, male: n=concussed football players, n=18 non-concussed football players and n=14 non-contact sports controls: basketball, cross-country track; Meier, T. B. et al., 2015, *JAMA Neurology*, 72(5):530-8; Meier, T. B. et al., 2016a, *J Neurotrauma*, 33(4):330-8; Meier, T. B. et al., 2016b, *Brain Imaging and Behavior*, 11(1): 129-140). 50 athletes from the Univ. of Ben Gurion, Israel were enrolled (average age 26.5+/−3, male) to study chronic effects of concussion and repeated sub-concussive impacts during game season ("ON") and outside of the season ("OFF"); and 10 non-contact athlete controls; n=31 athletes and 17 paired athletes.

Biomarker Assay Methods:
For Western blotting, ALDOC isoform-specific monoclonal antibodies (MAbs) were used (EnCor Biotechnology, Inc., Gainesville, Fla.). Standardized Western blotting assays were developed at the Semel Institute at UCLA. Sub-saturated densitometry of enhanced chemiluminescence exposures was used for measuring protein bands. Data were analyzed using standardized detection and exposure conditions alongside known amounts of recombinant proteins (EnCor). Data were analyzed using standardized exposure conditions alongside known amounts of recombinant proteins (EnCor). MSD-ELISA Assays, Serum Aldolase C (ALDOC) and Glial Fibrillary Acidic Protein (GFAP) concentrations were assessed in replicate tests using high sensitivity sandwich ELISA tests developed using antibodies purchased and optimized at ImmunArray. Serum samples were tested across replicate assays, using a MesoScale Discovery (MSD) electro-chemiluminescence on a Quick-Plex120 instrument. Statistical analyses included repeated measures ANOVA, Mann-Whitney rank sum test, univariable logistic regression, Wilcoxon test for median differences, paired T-tests for mean differences and permutation tests (exact match). Tests were performed with an $\alpha$=0.05, 95% confidence level. Correlations of biomarkers and dynamic contrast enhanced magnetic resonance imaging, MRI, (e.g., DCE-MRI) findings were performed with Spearman's pairwise correlation coefficient $\rho$. Only $\rho$ values greater than 0.5 or less than −0.5 were reported. By way of example, DCE imagining techniques (e.g., DCE-MRI) are reviewed in O'Connor, J. P. B. et al., 2011, Br. J. Radiol., 84 (Spec Iss 2):5112-5120; and Weissberg et al. (2014, JAMA Neurology, 71(11):1453-1455), incorporated by reference herein, report on the use of DCE-MRI for mapping and assessing BBB lesions and dysfunction in patients with mTBI.

Example 2: Astroglial Injury-Defined Biomarkers in Diagnostic Monitoring after mTBI and the Potential for Aldolase C (ALDOC) as a Robust Biomarker in Biological Samples Traumatic brain injury (TBI) is an expanding global public health concern, with mild TBI (mTBI) accounting for 70-90% of all cases. Assessing brain injury severity and determining the risk for lasting symptoms among mTBI subjects is a challenge for clinical practice, sports events and military care. Despite being common, diagnostic evaluation and monitoring of subjects with head injury remains imprecise and subjective, and would greatly benefit from robust blood-based biomarkers for objective real-time testing. The astroglial intermediate filament protein, Glial Fibrillary Acidic Protein (GFAP), as a TBI biomarker provides insufficient sensitivity and timely presence among mTBI patients with a negative computed tomography (CT) finding, lacking lesions. Thus, a new class of biomarkers would be highly beneficial for assessment of hyper-acute and sufficient elevation for point-of care detection and release based on trauma pathophysiology beyond tissue demise to adequately represent reversible compromise after mTBI.

A recent proteomic screen discovered substantial cytosolic protein release within minutes after mechanical trauma to astrocytes (Levine, J. et al., 2016, *Glia*, 64(5):668-694). Among confirmed trauma-released proteins was the glycolytic enzyme Aldolase C (ALDOC), a brain-specific isoform that constitutes 1-2% of the brain protein mass (Thompson et al., 1980). Robust elevation of ALDOC in TBI patients' CSF, serum and plasma using mass spectrometry and standardized immunoblotting densitometry was confirmed (Halford et al., 2017, "New astroglial injury defined biomarkers for neurotrauma assessment." (manuscript accepted)). Novel biofluid kinetics, stability and association to mechanoporation, (membrane wounding) distinguished ALDOC from GFAP, in that GFAP release and rapid proteolytic degradation were found to be associated with delayed cell death, dependent on injury severity (Halford et al., Ibid.).

This Example presents results of an analysis of clinical samples to examine serum-based ALDOC and GFAP levels in various cohorts of mTBI patients and sports-related concussion victims.

Methods: The study established highly specific serum detection of ALDOC compared with that of GFAP in two well-characterized mTBI patient cohorts, in a healthy population and in two collections of football players. Serum samples were drawn from subjects during the on-season and off-season and from athletes with concussions or with a history of concussion versus non-concussed contact sports players. High sensitivity mesoscale discovery electrochemiluminescence (MSD)-ELISA assays and standardized sub-saturated immunoblotting densitometry methods were used to detect ALDOC and GFAP protein levels and their breakdown products (BDPs) in the various samples. Site-specific and isoform-specific antibody binding was characterized using recombinant Aldolase proteins. Antibody targets were defined on immunoblots prior assay assembly. Biomarker levels were compared between groups using Rank Sum Tests, paired T-tests and permutation and normality tests. 3T series and gadolinium contrast MRI analysis was performed to assess blood-brain barrier permeability. Spearman's paired correlation coefficient (rho) was used to evaluate relationships between MRI metric changes and biomarker levels in same subjects.

Results: The ALDOC biomarker was exclusively expressed in CNS tissues, and antibodies were specific for ALDO-C versus ALDO-A and ALDOC-B isoforms in both assay types. ELISA results detected ALDOC and GFAP in TBI patients, confirming results of immunoblot densitometry, both showing robust detection of ALDOC in biofluids after TBI versus healthy controls. (FIGS. 1A-1G and 2A-2C). ALDOC was also elevated in serum samples of a small cohort of Italian mTBI patients irrespective of their CT-status, already present at one hour post-mTBI. (FIGS. 4A-4D). This contrasted to GFAP elevation that was seen with delay only in mTBI patients with positive CT findings. (FIGS. 3A-3C). In HeadSMART mTBI patients (males, aged 18-40, n=139), ALDOC levels were significantly elevated in mTBI patients versus healthy control subjects (age matched n=20; p<0.05), as was GFAP. (FIG. 3C). In the Laureate Institute's NCAA athlete study, median ALDOC levels were significantly elevated in concussed NCAA athletes within three days after injury, compared to those of healthy controls and non-concussed players. In contrast, GFAP levels were not elevated using in immunoblot densitometry for multiple GFAP breakdown products. (FIGS. 4A-4D). The Ben Gurion University study of a cohort of football players (aged 18-40), found significantly elevated ALDOC levels during the on-season versus off season (n=25 each group), which correlated with blood-brain barrier permeability changes by 3T MRI (Spearman's paired pairwise correlation rho=0.61 whole brain volumes, and 0.66 white matter). In contrast, GFAP levels were not elevated in these athletes using an ultra-sensitive GFAP-specific ELISA. Levels of ALDOC and GFAP were positively correlated, with stronger correlation during the active athletic season, and in players with a previous history of concussion (rho=0.34 vs. 0.93, respectively). (FIGS. 4A-4G and FIGS. 5D, 5DA, 5E and 5EA). ALDOC and GFAP levels also correlated with DTI (Spearman) analysis (FIG. 4H). Both ELISA and immunoblot assays confirmed ALDOC elevation after TBI (and mTBI) compared to healthy controls (all reported comparisons were significant at α=0.05).

The data in this Example documented serum ALDOC and GFAP levels in several mTBI and concussion cohorts that differed by country, age- and athlete groups, using two independent quantitative approaches. The findings showed robust ALDOC elevation in single to double digit ng/ml serum amounts after mTBI including sports concussions, while GFAP levels were by an order of magnitude lower or absent after mTBI and concussions.

In HeadSMART mTBI patients, ALDOC was significantly elevated versus healthy controls. ALDOC levels rose significantly in concussed NCAA athletes after injury, versus controls and non-concussed players. In Israeli football players, ALDOC elevation, but not GFAP, was detected in concussed players versus controls. ELISA testing and immunoblotting analysis for GFAP breakdown products found no GFAP elevation in either athlete study despite elevation in severe TBI and in some mTBI patients. Overall, multiple mTBI cohorts of different ages, athletic groups, and geographical location support ALDOC as a robust biomarker for mTBI. The data support the use of ALDOC as a more sensitive biomarker for identifying mTBI (mTBI), based on temporary astroglial wounding. (FIGS. 6A-6E). GFAP is also more informative for moderate to severe TBI with significant astroglial demise.

These studies support the use of a brain-specific Aldolase C isoform MSD platform assay to detect more subtle types of injury, including cell (e.g., astroglial cell) compromise, blood-brain barrier permeability changes and glial fiber damage that may persist long after acute injury. These studies provide a basis for the use of ALDOC together with other biomarkers employing modeling to predict patient outcomes, and associate distinct MRI analysis of changes in vascular permeability in the blood brain barrier to further understand mTBI pathophysiology and its reversible nature. (FIGS. 4F and 4G; FIGS. 5D, 5DA, 5E and 5EA).

This Example shows that the brain-specific Aldolase C isoform provides a reliable biomarker protein for the detection of more subtle types of injury, including concussion and mild TBI, as well as for the detection of non-lethal cell damage, blood-brain barrier permeability changes and glial fiber damage that may persist long after acute injury.

Example 3: MRI Findings Showing Changes in Vascular (BBB) Permeability and Correlated Brain Injury Biomarker Levels in Sera of Concussed Athletes: Comparison with Age-Matched Individuals with Mild TBI (mTBI)

The incidence of sports related concussion or mTBI ranges between 300,000 to nearly 4 million annually, depending on the age range studied. Despite this major public health concern, a lack of clinical guidelines exists for determining and assessing the condition and testing and providing effective treatments.

This Example describes a study which examined brain-specific protein biomarkers, e.g., central nervous system (CNS) biomarkers, detected in human serum and compared the findings with areas of blood brain barrier (BBB) damage, i.e., areas showing changes in vascular permeability or damage to the vasculature or BBB, as visualized using MRI neuroimaging, specifically, contrast MRI, e.g., 3T MRI (a 3 tesla unit-Magnetic Resonance Imaging machine/system, which provides improved spatial resolution and contrast, reduced imaging time and thinner slices compared with 1.5T MRI systems).

Serum biomarker levels were studied in different types of mild brain injury. Subgroups studied were healthy controls from the HeadSMART TBI study, samples from individuals with TBI from the HeadSMART study, athletic controls from an athletic study conducted in Ben Gurion University in Israel, and on and off season American football players from the same study at Ben Gurion University. The biomarkers included Aldolase-C (ALDOC), Brain-derived neurotrophic factor (BDNF), Glial Fibrillary Acidic Protein (GFAP), Neurogranin (NRGN), Neuron Specific Enolase (NSE), Oligodendrocyte Myelin glycoprotein (OMG) and Synuclein Beta (SNCB). The box plots in FIG. 4I and FIG. 4IA show the distribution of data from detected levels of each of seven biomarkers tested.

In the analysis, Aldolase C (ALDOC), a glycolytic enzyme that is abundant in the cytoplasm, was studied as a brain injury-associated biomarker, along with other biomarkers. ALDOC is expressed mainly in the brain and is specific for brain tissues; it is expressed in highest levels in astrocytes and has been shown to be concentrated in astrocytic end-feet, which are tightly bound to endothelial cells along the full surface area of brain blood vessels, thereby actively maintaining the blood brain barrier.

Blood/serum samples obtained from four clinical cohorts were analyzed in replicate ELISA immunoassays, namely, peroxidase-based detection or electro-chemiluminescent (MSD) ELISA assays. A cohort of 31 football players from Ben Gurion University (19 with paired off- and on-season serum samples) was studied and compared with athletic controls (non-contact sports athletes; n=10). These athletes were evaluated with National Football League (NFL) assessments, clinical histories, and advanced MRI techniques to assess blood brain barrier (BBB) permeability. As reference comparisons, age-matched male patients with mild TBI (mTBI), (HeadSMART, n=141, Johns Hopkins University (JHU), median age 26.0 years) and healthy controls (HeadSMART, Johns Hopkins University, n=20, median age 24.5 years) were studied and compared with the athletic cohorts.

Athletic cohorts were studied by structural MRI, dynamic contrast-enhanced MRI, and diffusion tensor-weighted imaging (DTI) and clinical assessments. Serum samples were tested for biomarker levels. The study demonstrated that in athletes with concussion, GFAP levels did not show a difference from those of controls. In contrast, the findings described in this example show that ALDOC was significantly altered in football players with a prior history of concussive injury, as demonstrated in Tables 1 and 1A below. Table 1A is an addendum that represents a greater number of patients examined by the same assays, and thus is updated data, and subsequent DIVIDE values were calculated using an alternate method.

TABLE 1

Statistical comparison of non-contact sport athletes (control) and football players with and without a prior history of concussion

| Summary of results Comparison | Measure> Method> | Median (Rank sum test) | Mean (paired T-test) | Permutation (exact match) | n |
|---|---|---|---|---|---|
| BG control vs BG on prior concussion | GFAP | 0.57 | 0.32 | 0.23 | 19 |
| | ALDOC | 0.048 | 0.105 | 0.02 | 12 |
| BG control vs BG on no prior | GFAP | 0.86 | 0.92 | 0.91 | 15 |
| | ALDOC | 1 | 0.99 | 1 | 8 |
| BG control vs BG off prior concussion | GFAP | 0.55 | 0.43 | 0.33 | 20 |
| | ALDOC | 0.006 | 0.025 | 0.004 | 17 |
| BG control vs BG off no prior | GFAP | 0.93 | 0.88 | 0.86 | 12 |
| | ALDOC | 0.69 | 0.42 | 0.4 | 8 |
| BG on vs BG off (*paired, so same individual) | GFAP | 0.54 | 0.12 | 0.47 | 16 |
| | ALDOC | 0.26 | 0.28 | 0.32 | 9 |
| | | p value | | | |
| Unvariable logistic regression models | GFAP | 0.82 | | | 46 |
| | ALDOC | 0.08 | Trend toward sig | | 33 |

BG: Ben Gurion; study control and football player athletes analyzed

TABLE 1A

Statistical comparison of non-contact sport control athletes and football players with and without a prior history of concussion.

| Summary of results Comparison | Measure> Method> | Median (Rank sum test) | Mean (T-test) | Permutation (exact match) | n |
|---|---|---|---|---|---|
| BG control vs BG on prior concussion | GFAP | 0.58 | 0.32 | 0.23 | 19 |
| | ALDOC | 0.048 | 0.105 | 0.02 | 12 |
| BG control vs BG on no prior | GFAP | 0.86 | 0.92 | 0.91 | 15 |
| | ALDOC | 1 | 0.99 | 1 | 8 |
| BG control vs BG off prior concussion | GFAP | 0.55 | 0.43 | 0.33 | 20 |
| | ALDOC | 0.006 | 0.025 | 0.004 | 17 |
| BG control vs BG off no prior | GFAP | 0.94 | 0.87 | 0.86 | 12 |
| | ALDOC | 0.69 | 0.42 | 0.4 | 8 |
| BG on vs BG off (*paired, so same individual) | GFAP | 0.12 | 0.12 | 0.47 | 16 |
| | ALDOC | 0.13 | 0.17 | 0.85 | 9 |
| Unvariable logistic regression models | GFAP | 0.87 | 0.82 | 0.82 | 46 |
| | ALDOC | 0.06 | 0.05 | 0.08 | 33 |

In the study, serum biomarker levels of Neurogranin (NRGN) and Synuclein Beta (SNCB) (FIG. 4J, shown in the box plots surrounded by rectangles) were detected at higher levels in football players with 3 or more concussions than in players with 2 or fewer concussions, thus suggesting a general threshold for the establishment of chronic deterioration after brain injury.

Tables 2 and 3 below present a comparison of serum biomarker levels in athletic control individuals versus off-season football players (Table 2 and Table 2A) or on-season football players with prior concussion (Table 3 and Table 3A). The DIVIDE values in Tables 2A and 3A were calculated using an alternate method.

TABLE 2

Serum biomarker levels in athletic control individuals compared with off-season football players

| Feature | P-value (Wilcoxon) | T-value | P-value (Perm-exact.mc) |
|---|---|---|---|
| NRGN | 0.7922 | 0.9252997 | 0.9310345 |
| SNCB | 0.1320 | 0.1194529 | 0.1139430 |
| NSE | 0.0260 | 0.0170555 | 0.0149925 |
| GFAP | 0.9372 | 0.8725172 | 0.8565717 |
| BDNF | 0.3939 | 0.8834738 | 0.9170415 |
| OMG | 0.6905 | 0.5439210 | 0.8535732 |
| ALDOC | 0.6857 | 0.4187137 | 0.4027986 |
| DIVIDE_Allbrain | 0.4762 | 0.4850248 | 0.5392304 |
| DIVIDE_WM | 0.4762 | 0.3002268 | 0.3308346 |
| DIVIDE_GM | 1.0000 | 0.6041399 | 0.6311844 |

TABLE 2A

Serum biomarker levels in athletic control individuals compared with off-season football players.

| Feature | P-value (Wilcoxon) | T-value | P-value (Perm-exact.mc) |
|---|---|---|---|
| NRGN | 0.792 | 0.925 | 0.931 |
| SNCB | 0.132 | 0.119 | 0.114 |
| NSE | 0.026 | 0.017 | 0.015 |
| GFAP | 0.937 | 0.873 | 0.857 |
| BDNF | 0.394 | 0.883 | 0.917 |
| OMG | 0.691 | 0.544 | 0.854 |
| ALDOC | 0.686 | 0.419 | 0.403 |
| DIVIDE_Allbrain | 0.310 | 0.309 | 0.312 |
| DIVIDE_WM | 0.180 | 0.861 | 0.187 |
| DIVIDE_GM | 0.699 | 0.412 | 0.448 |

TABLE 3

Serum biomarker levels in athletic control individuals compared with on-season football players with prior concussion

| Feature | P-value (Rank sum test) | T-value | P-value (Perm-exact.mc) | N (total) |
|---|---|---|---|---|
| NRGN | 0.1528 | 0.037979 | 0.113943 | 20 |
| SNCB | 0.8983 | 0.5448209 | 0.6911544 | 19 |
| NSE | 0.0874 | 0.0902947 | 0.065967 | 19 |
| GFAP | 0.5789 | 0.3156639 | 0.2333833 | 19 |
| BDNF | 0.3023 | 0.7179276 | 0.6116942 | 21 |
| OMG | 0.0375 | 0.0049799 | 0.0454773 | 18 |
| ALDOC | 0.0485 | 0.1052246 | 0.0204898 | 12 |
| DIVIDE_Allbrain | 0.08 | 0.0458705 | 0.1124438 | 19 |
| DIVIDE_WM | 0.08 | 0.0378702 | 0.1154423 | 19 |
| DIVIDE_GM | 0.08 | 0.0434655 | 0.1074463 | 19 |

TABLE 3A

Serum biomarker levels in athletic control individuals compared with on-season football players with prior concussion

| Feature | P-value (Rank sum test) | T-value | P-value (Perm-exact.mc) | N (total) |
|---|---|---|---|---|
| NRGN | 0.153 | 0.038 | 0.114 | 20 |
| SNCB | 0.898 | 0.545 | 0.691 | 19 |
| NSE | 0.087 | 0.09 | 0.066 | 19 |
| GFAP | 0.579 | 0.316 | 0.233 | 19 |
| BDNF | 0.302 | 0.718 | 0.612 | 21 |
| OMG | 0.038 | 0.005 | 0.045 | 18 |
| ALDOC | 0.048 | 0.105 | 0.02 | 12 |
| DIVIDE_Allbrain | 0.005 | 0.001 | 0.014 | 21 |
| DIVIDE_WM | 0.008 | 0.001 | 0.012 | 21 |
| DIVIDE_GM | 0.003 | 0.001 | 0.016 | 21 |

In Tables 2, 2A, 3 and 3A, Spearman's pairwise correlation of BBB permeability signals from dynamic contrast enhanced MRI signals and serum biomarker levels was performed for football players 2-5 months off-season and in age-matched athletic controls (non-contact athletes). Correlations between serum biomarker detection and MRI findings for BBB disruption were determined. In addition, Spearman's coefficient (p) was provided in heatmap format to identify relationships between biomarkers and brain volumes (voxels) of brain enhancement after MRI using gadolinium contrast agent to assess blood brain barrier leakage (vascular damage or leaking) in each comparison. Measurements of blood brain barrier (BBB) leakage in total brain volume ("DIVIDE Allbrain"), total white matter BBB leakage ("DIVIDE_WM"), or total gray matter ("DIVIDE_GM"), after normalization for local blood flow, were made. The results of the correlation analysis are shown in FIG. 5D and FIG. 5DA.

FIGS. 5E and 5EA present Spearman correlations in a larger athlete group (all athletes) including on-season and off-season football players, as well as non-contact sport athlete controls. The Spearman correlation showed positive correlation of GFAP, OMG, and ALDOC levels, as well as ALDOC levels correlated with DCE-MRI signals (DIVIDE DCE-MRI) from total brain volume (DIVIDE_Allbrain), white matter volume (DIVIDE_WM) and gray matter volume (DIVIDE_GM). DIVIDE signals also showed a positive correlation with GFAP biomarker levels. These findings are believed to provide the first evidence of a link between these seven specific biomarkers and blood-brain barrier breakdown in athletes. Weak correlations were also shown for levels of SNCB with levels of NSE, BDNF and ALDOC. Weak negative correlation was shown for levels of NRGN with levels of SNCB and OMG, and weak positive correlation was shown with levels of NRGN and GFAP.

Results: The levels of the BDNF and SNCB protein biomarkers were correlated in football players and in the individuals with mild TBI (rho=0.58, Spearman correlation), and the levels of both of these biomarker proteins were decreased compared with the levels of these proteins in healthy controls. GFAP and NSE levels were elevated in athletes with mTBI. Certain biomarkers, such as NSE, were also found to be elevated in athletic controls. The levels of ALDOC showed the strongest correlation with BBB permeability signals measured by MRI, while the level of GFAP protein biomarker was weakly correlated. Elevated biomarker levels and MRI correlations were strongest in athletes with prior concussion histories. ALDOC, GFAP and OMG were highly correlated. The levels of ALDOC, GFAP and NSE biomarker proteins were elevated in individuals with mTBI, but GFAP was not significantly elevated in football players. The level of BDNF was decreased in athletes (i.e., "on" season athletes sustaining injury), consistent with levels in individuals with mild TBI (in the HeadSMART study). (FIGS. 4E, 4F, 4G, 5D, 5DA, 5E and 5EA).

The results obtained in these studies showed that elevated levels of certain protein biomarkers in blood or serum are associated with BBB permeability. Thus, the association of measured/quantified biomarker levels with BBB permeability (detected by quantitative neuroimaging) provides a method for assessing and monitoring brain repair (and/or patient outcome) following injury. By way of example, in football players between the on and off seasons, such neuroimaging and biomarker level detection may offer useful information regarding the effects of head injury and repetitive sub-concussive hits, and can inform medical decisions related to return to work and play.

In football players between the on and off seasons, the detection and monitoring of the levels of one or more (or all) of these biomarker proteins in samples obtained from the individuals at various times can inform the medical practitioner or clinician, the athletes themselves, trainers, coaches and associated personnel regarding the effects of repetitive sub-concussive hits. In addition, the practice of the methods for detecting and monitoring the levels of these biomarker proteins can guide and inform decisions of the medical community, such as sports medical personnel, regarding the timing of returning to work and/or to play (or not to play) for both athletes and non-athletes.

Example 4: Serum Levels of Oligodendrocyte Myelin Glycoprotein (OMG)

As described supra, in studies correlated with MRI neuroimaging analysis, Oligodendrocyte Myelin Glycoprotein (OMG) is a biomarker of brain injury whose levels in a biological sample, e.g., a blood or serum sample, relative to control levels was elevated (along with elevated levels of ALDOC and GFAP) in subjects (e.g., athletes) with prior history of concussion. Oligodendrocytes damaged during brain injury and disease shed Oligodendrocyte Myelin Glycoprotein (OMG) protein form the cell membrane as part of the repair process. The OMG protein is 440 amino acids in length and has the amino acid sequence as set forth below (SEQ ID NO: 1):

```
MEYQILKMSLCLEILLFLTPGILCICPLQCICTERHRHVDCSGRNLSTL
PSGLQENIIHLNLSYNHFTDLHNQLTQYTNLRTLDISNNRLESLPAHLP
RSLWNMSAANNNIKLLDKSDTAYQWNLKYLDVSKNMLEKVVLIKNTLRS
LEVLNLSSNKLWTVPTNMPSKLHIVDLSNNSLTQILPGTLINLTNLTHL
YLHNNKFTFIPDQSFDQLFQLQEITLYNNRWSCDHKQNITYLLKWMMET
KAHVIGTPCSTQISSLKEHNMYPTPSGFTSSLFTVSGMQTVDTINSLSV
VTQPKVTKIPKQYRTKETTFGATLSKDTTFTSTDKAFVPYPEDTSTETI
NSHEAAAATLTIHLQDGMVTNTSLTSSTKSSPTPMTLSITSGMPNNFSE
MPQQSTTLNLWREETTTNVKTPLPSVANAWKVNASFLLLLNVVVMLAV
```

A polypeptide or peptide fragment thereof having at least about 85% or greater, e.g., 90%, 95%, 98%, or 99% amino acid identity to the above OMG amino acid sequence is encompassed herein.

FIG. 7B shows protein interactions using STRING.

Summary of Results for Detecting OMG Levels in the Sera of Human Patients

Significant differences in serum OMG levels were found using three separate statistical tests: Wilcoxon rank sum test comparing median values per group, paired T-tests to compare differences in mean values and exact match permutation tests. The results are summarized in Tables 4 and 5 below. Significant differences were found between healthy controls and TBI (HeadSMART TBI patients) and between healthy controls and Football players, or active, non-contact-sport athletic control subjects (swimmers and track runners) and football players sustaining repetitive injury or concussion during the active football season. In both cases, OMG levels were decreased in the brain injured population (FIG. 8).

TABLE 4

Statistical differences in control and TBI patients

| Comparison | Wilconxon p value (median difference) | Paired T-Test (mean difference) | Permutation test (Stringent test) | Samples analyzed (n) |
|---|---|---|---|---|
| Trauma control vs TBI | 0.0020* | 0.0010042* | 0.0039980* | 29 |
| Healthy control vs TBI | 0.3971 | 0.0854 | 0.03598* | 38 |

*Statistically different with 95% confidence, α level 0.05.

TABLE 5

Serum levels of OMG in athletes (non-contact versus American football)

| Comparison | Wilconxon p value (median difference) | Paired T-Test (mean difference) | Permutation test (Stringent test) | Samples analyzed (n) |
|---|---|---|---|---|
| Non-contact athlete control vs On-season repetitive injury (Football) | 0.0375 | 0.0049799 | 0.0454773 | 18 |
| Healthy controls vs On-season repetitive injury (Football) | 0.0165 | 0.0258 | 0.0315 | 22 |

*Statistically different with 95% confidence, α level 0.05.

Serum OMG levels were also shown to correlate with areas of blood brain barrier breakdown due to sports related injury, as detected using dynamic contrast-enhanced MRI imaging. Voxel volumes were compared in whole brain, gray matter and white matter and were correlated with biomarker levels using Spearman's pairwise correlation coefficient as described supra. OMG was positively correlated with other glial biomarkers, i.e., GFAP (p=0.64) and Aldolase C (ALDOC), (p=0.58); a weak negative correlation with NRGN (p=−0.26) was demonstrated. OMG also positively correlated with the volume of affected brain in the blood brain barrier permeability findings, including whole brain (0.57), white matter (0.56), and gray matter (0.51).

Effects of Repetitive Injury on OMG Levels

A history of prior concussion also increased the strength of some of the correlations, for example, the number of years playing football correlated with decreasing serum OMG levels, and OMG was found to be lower in football players with a history of concussion (FIG. 9).

Example 5: Fiber Tract-Specific Damage Detected in Football Players by MRI Neuroimaging Correlates with Changes in Specific Neuronal Biomarkers Detected in Patient Serum Patients can sustain life-altering head injuries despite having a normal cranial CT imaging. This example describes a study in which MRI neuroimaging, for example, Diffusion Weighted Tensor Imaging (DTI), and serum sample bioassays were employed to evaluate whether neuronal biomarkers are correlated with damage to specific tracts in the brains of subjects undergoing testing. Diffusion weighted tensor imaging evidence of white matter damage, a hallmark of sports-related concussion, and TBI were assessed in the study.

High sensitivity enzyme linked immunosorbent assays (ELISAs), e.g., FLISA or MSD ELISAs, as described supra were used to detect brain injury biomarker proteins in a sample obtained from a subject undergoing testing. Suitable samples are described above and may include blood, serum, plasma, cerebrospinal fluid, urine, sputum, etc. The brain injury biomarkers assayed in the serum samples were Brain-derived neurotrophic factor (BDNF), Neurogranin (NRGN), Neuron Specific Enolase (NSE), and Synuclein Beta (SNCB).

Serum concentrations were determined in replicate assays. A cohort of football players (n=31, 19 studied off-season and on-season), were enrolled from Ben-Gurion University (ages 18-40 years, median 25.5 years) along with age-matched athletic controls. Serum biomarker values were analyzed using univariable logistic regression and Spearman's pairwise correlation.

MRI volumes studied included 12 major fiber tracts and the corpus callosum, examining radial, axial, and mean diffusivity, and focal anisotropy. Biomarker levels were examined between groups for all tract-specific lesions using rank sum test, T-tests and permutation testing. Spearman's correlation (threshold>0.5 or <-0.5) was used to test associations with biomarkers (e.g., amounts/levels in serum) and DTI changes.

Study results: Paired samples obtained and assessed from football players on-season and off-season showed significant changes in the SNCB and NSE biomarker levels. NRGN, SNCB, and NSE biomarker levels were associated with changes affecting multiple long fiber tracts including the inferior fronto: occipital fasciculus (IFOF), the inferior lateral fasciculus (ILF) and the cingulum cingulate and hippocampal tracts. Increased BDNF biomarker levels were associated with changes in the cingulum cingulate tracts compared with normal controls, as detected by altered regional water content signals around the site of injury. In addition to blood brain barrier (BBB) permeability changes shown by DCE MRI signals (leaky vessels), correlations were also found between biomarkers and diffusion weighted tensor imaging (DTI-MRI) findings of fiber tract-specific lesions. These results are shown for football athletes tested during the active (within) season play. Biomarker changes may be associated with repetitive sub-concussive injury and may be the direct result of damage to specific fiber tracts, or fasciculae, in the brain. FIGS. 10A-10G present tables that summarize the results of Spearman's pairwise correlation of biomarkers, listed individually, indicating changes to specific fiber tracts in the brain. The FIG. 10A-10G tables present correlations between serum-biomarker (NRGN, SNCB, NSE, GFAP, BDNF, OMG, ALDOC, respectively) levels and MRI changes in specific fiber tracts in football players during the active (playing) season.

These preliminary findings are believed to be the first to relate serum levels of neuronal biomarkers to damage of anatomically specific fiber tract lesions that may have direct impacts on functional neuronal systems. Damage to the inferior fascicles may be related to visual deficits, and hippocampal tracts may affect memory function in patients. In football players and mild TBI patients in whom symptoms may be equivocal, these markers afford useful information regarding the effects of repetitive, sub-concussive impacts on specific brain regions.

Example 6: Biomarkers and Detection of Hemorrhage Using CT Scan/Imaging Analysis This Example describes a detailed analysis of biomarker levels in serum samples obtained from subjects involved in the HeadSMART study described herein, in conjunction with neuroradiology assessment, in particular, head (or brain) CT imaging (scanning). The analysis was conducted on the study findings to assess associations between biomarker levels and brain conditions or pathologies such as bleeding/hemorrhage and certain types of hemorrhage, namely, four types of hemorrhage: epidural hemorrhage, acute subarachnoid hemorrhage, acute subdural hemorrhage, and intraventricular hemorrhage.

Four separate statistical tests were used to determine significant changes in biomarker protein levels in an individual's sample compared to CT negative individuals: (i) P-value: (Wilcoxon, test of the rank sum test comparing median values for biomarker distributions in each group; (ii) T-value: compares means of biomarker distributions between groups (paired T-test); (iii): P-value: (Perm-exact.mc) Exact match permutation test comparing biomarker distributions; and (iv): Significance for all tests is set at 0.05-0.1 (90-95% confidence).

Figure 11B:
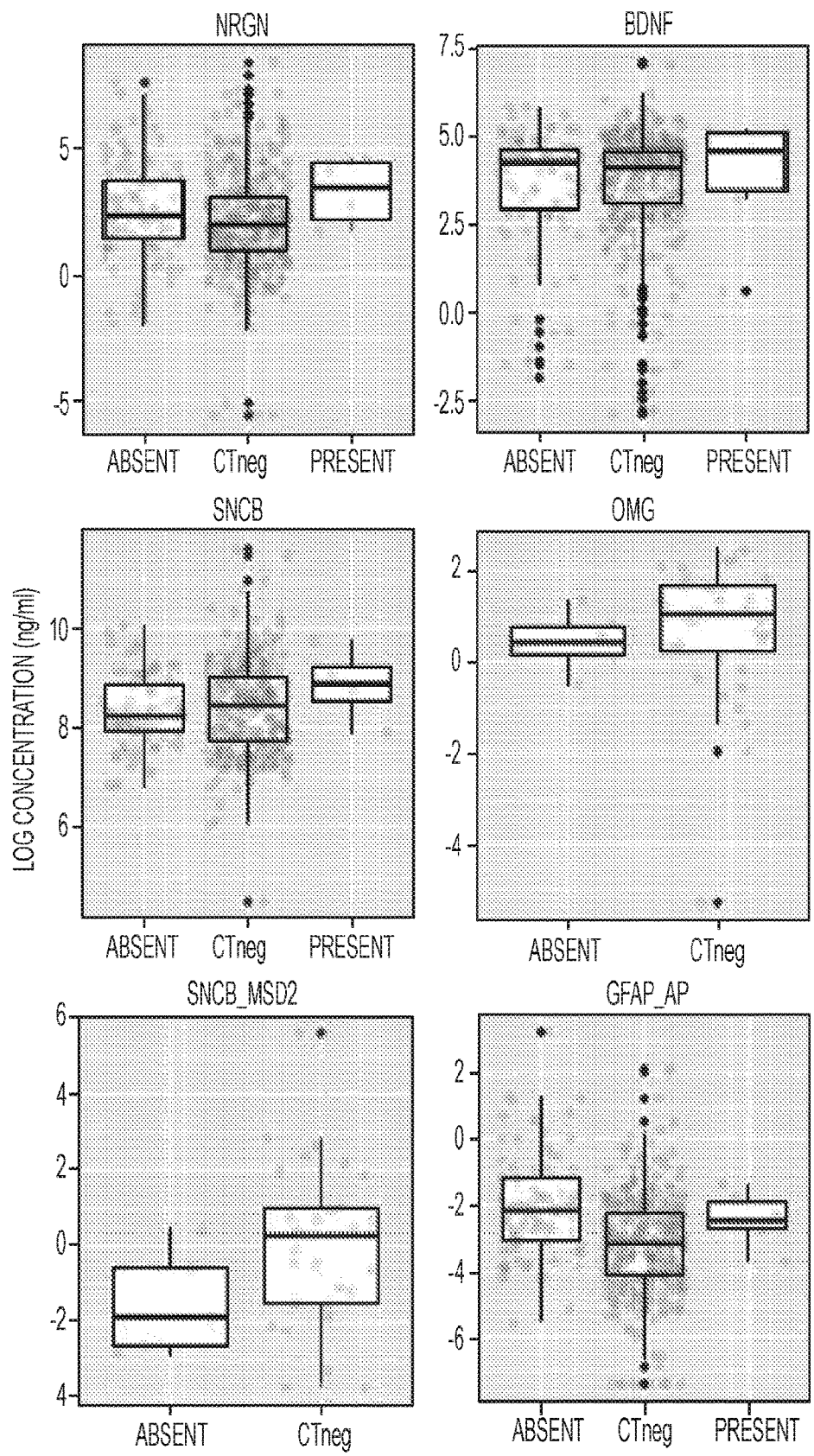
Figure 11B:
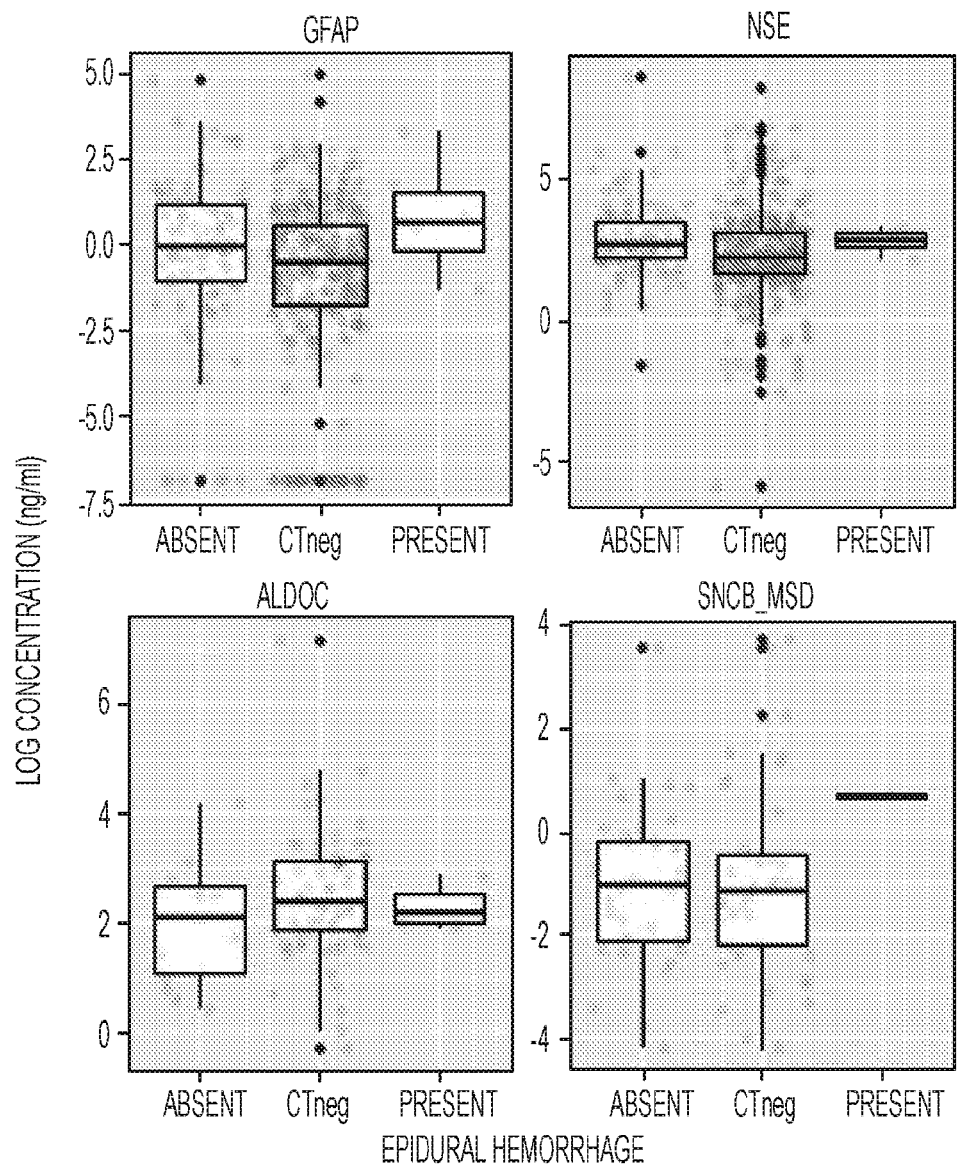
Figure 11C:
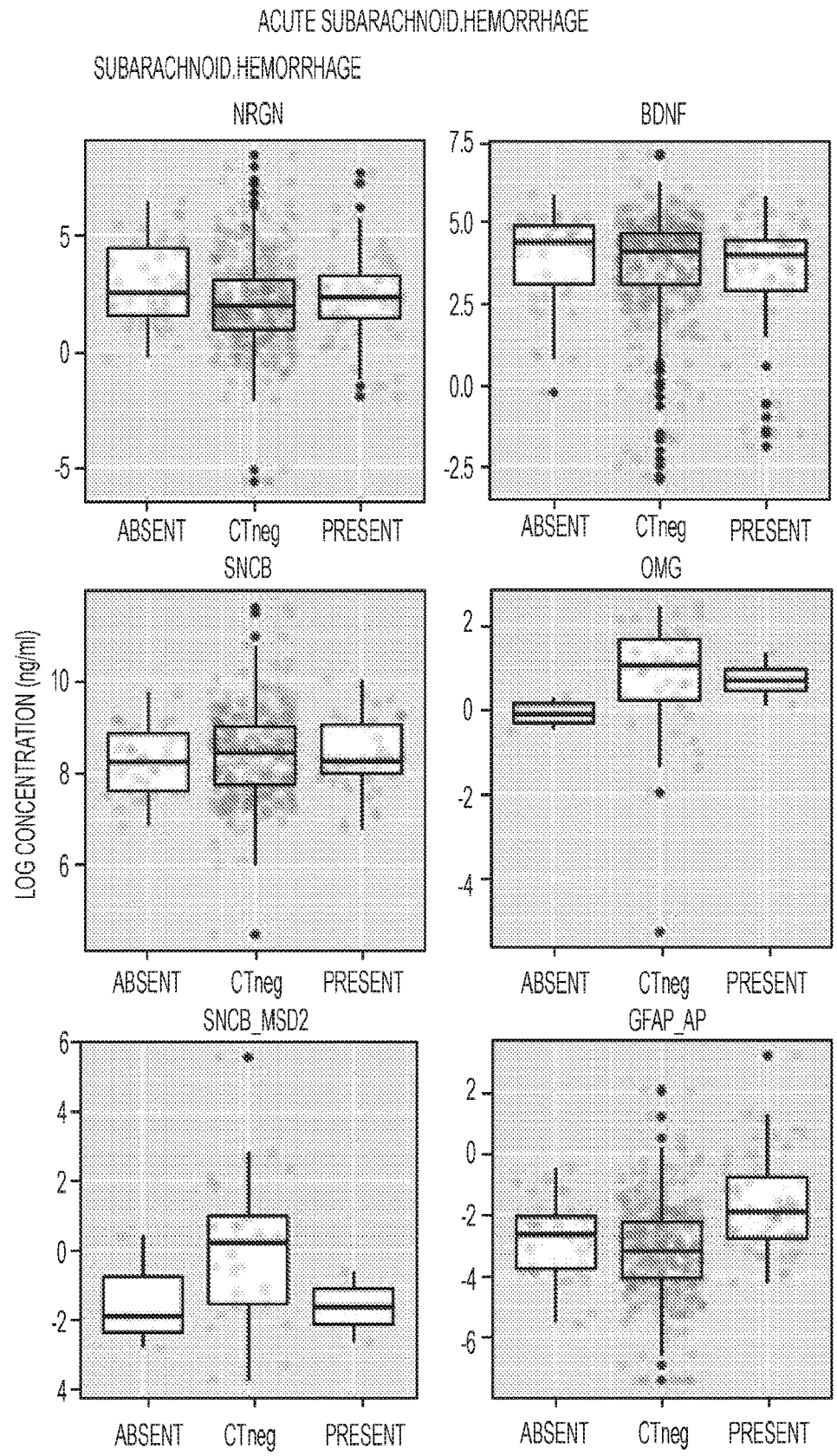
Figure 11C:
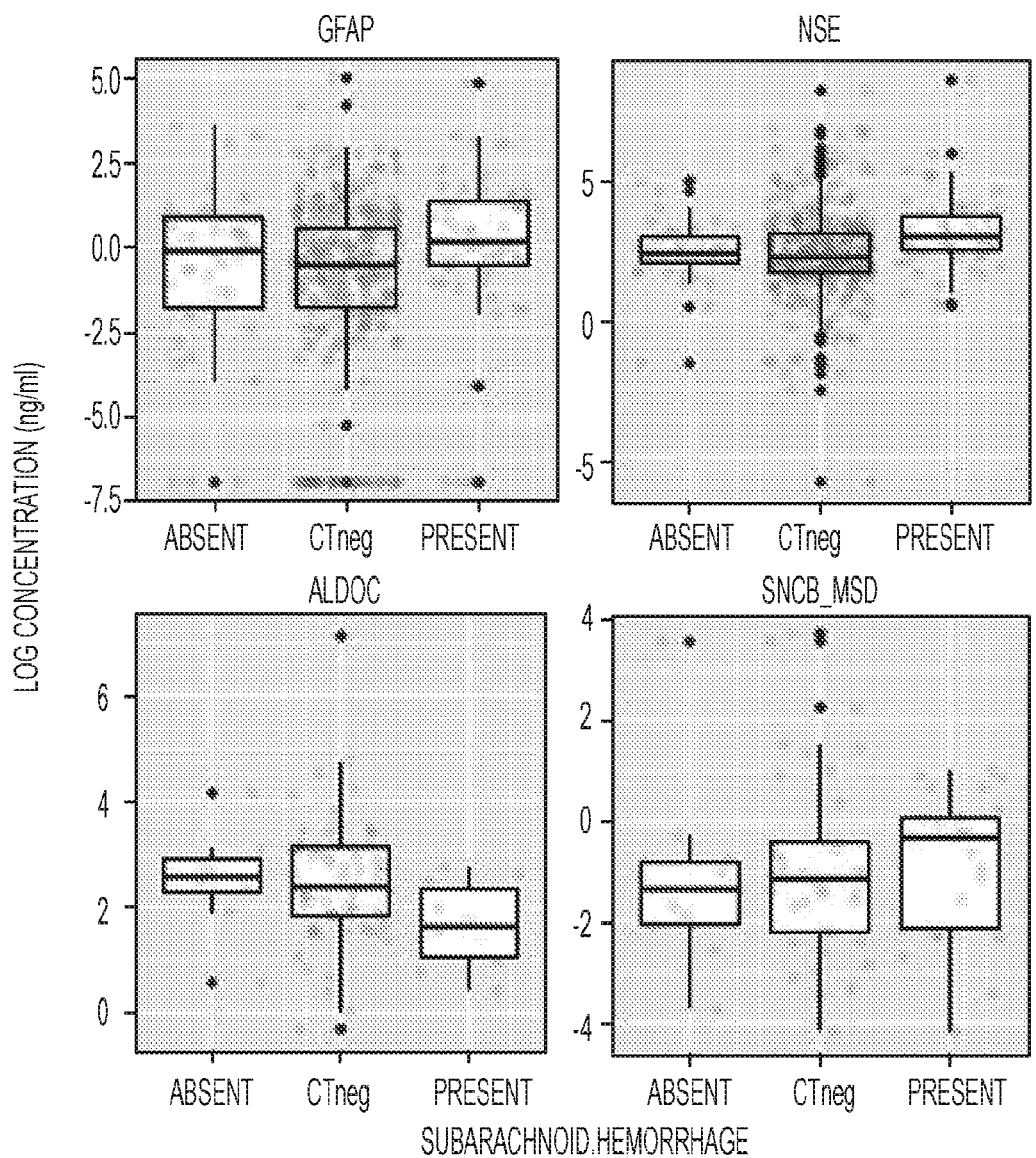
Figure 11D:
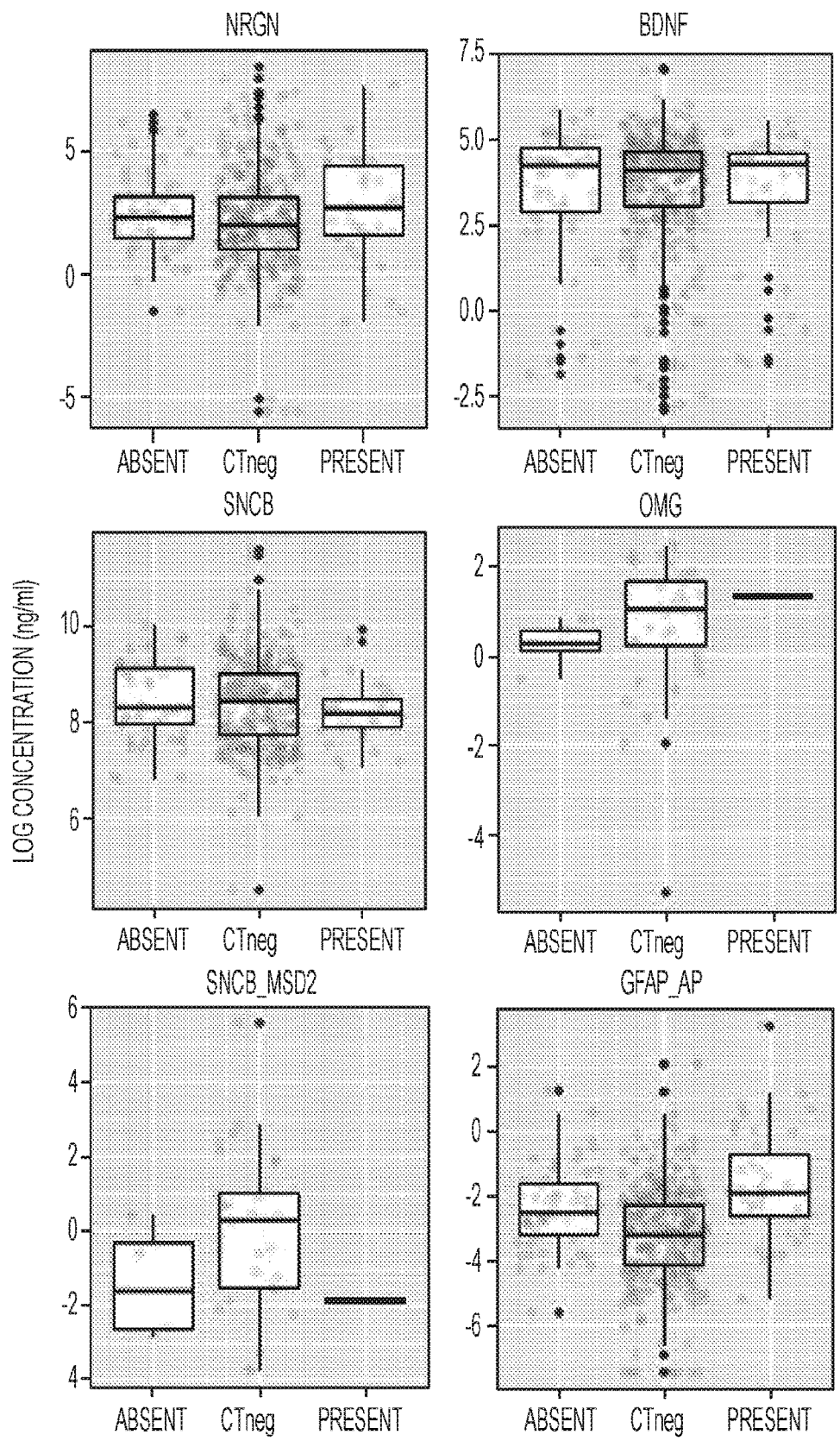
Figure 11D:
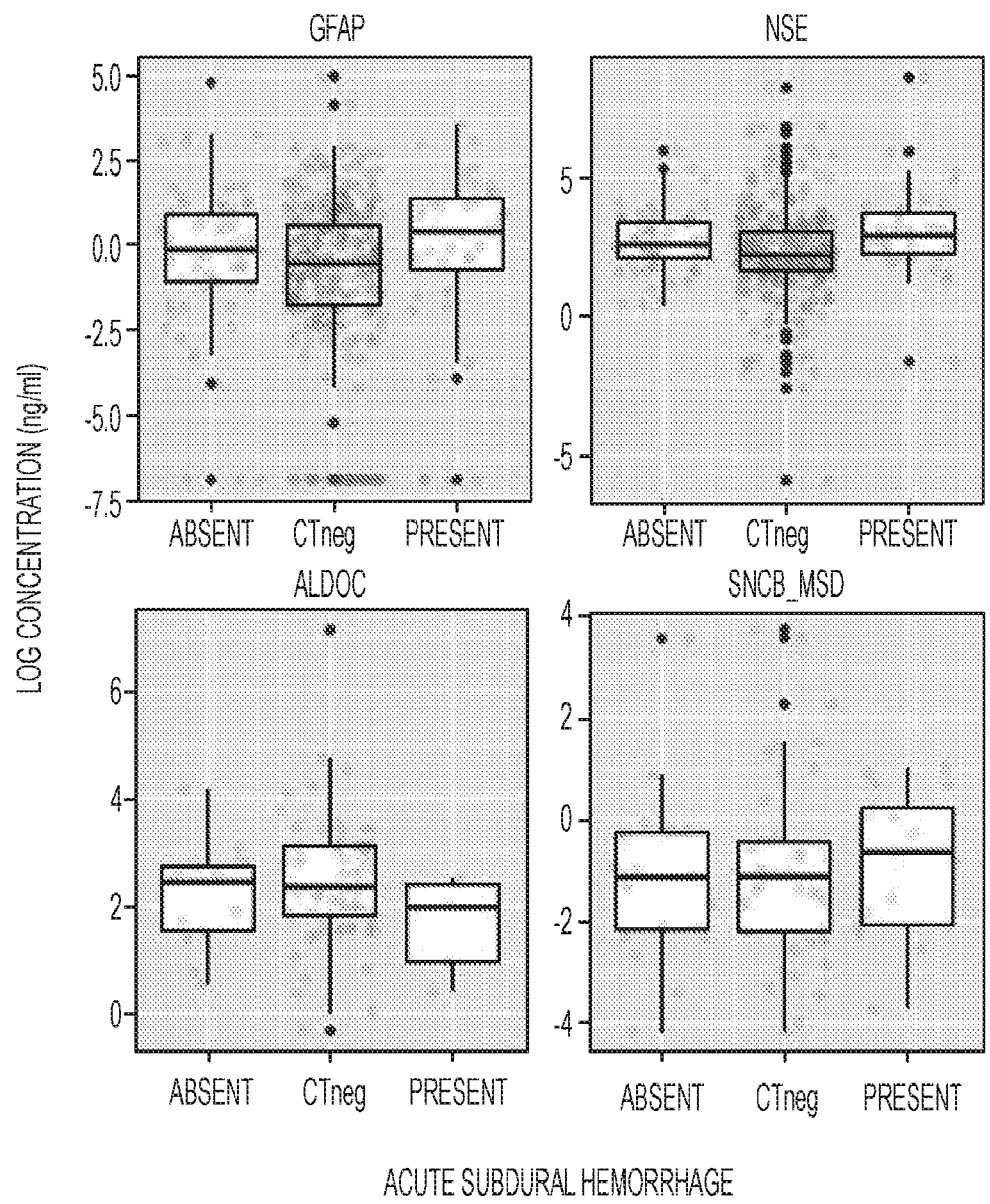
Figure 11E:
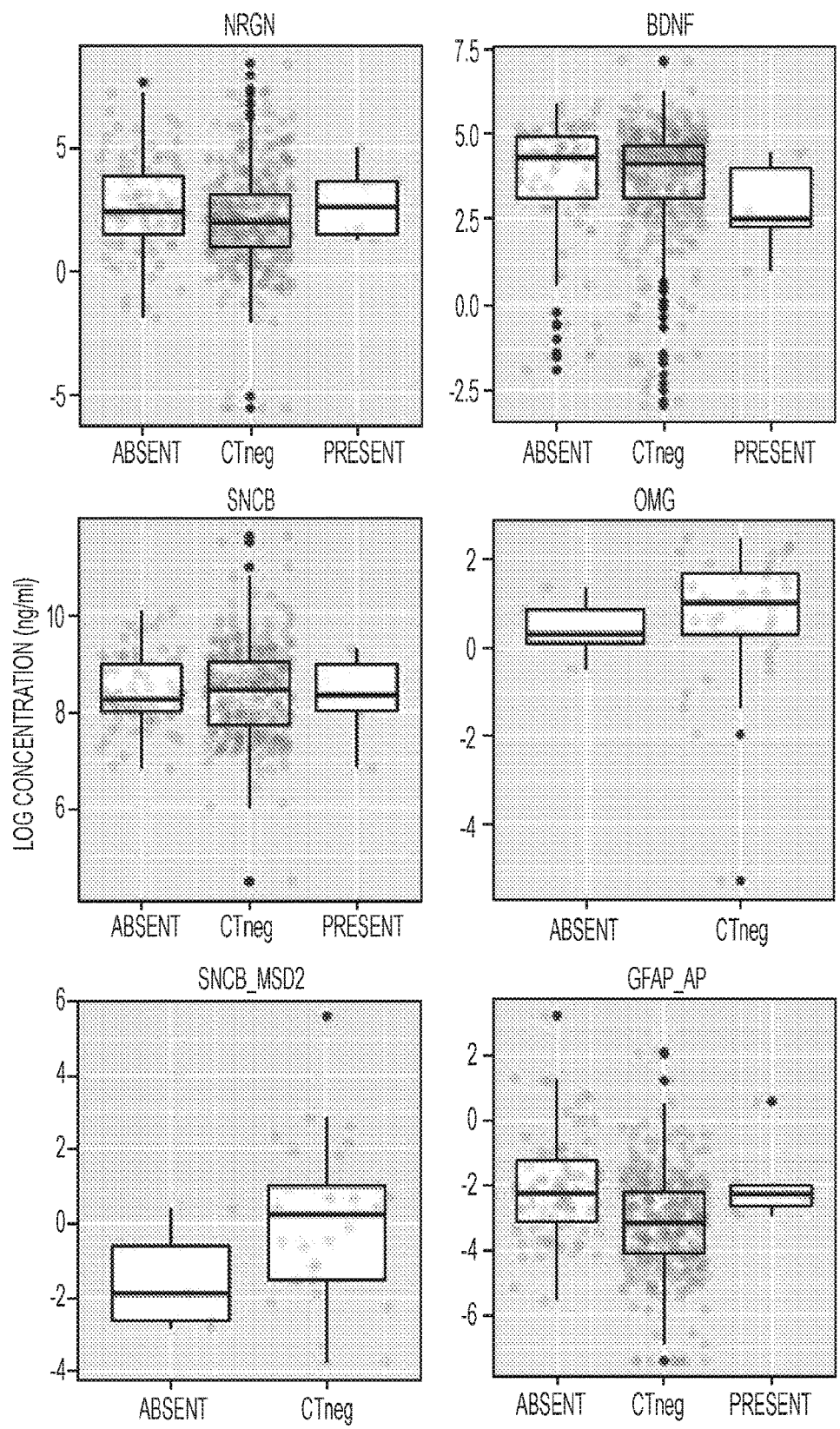
Figure 11E:
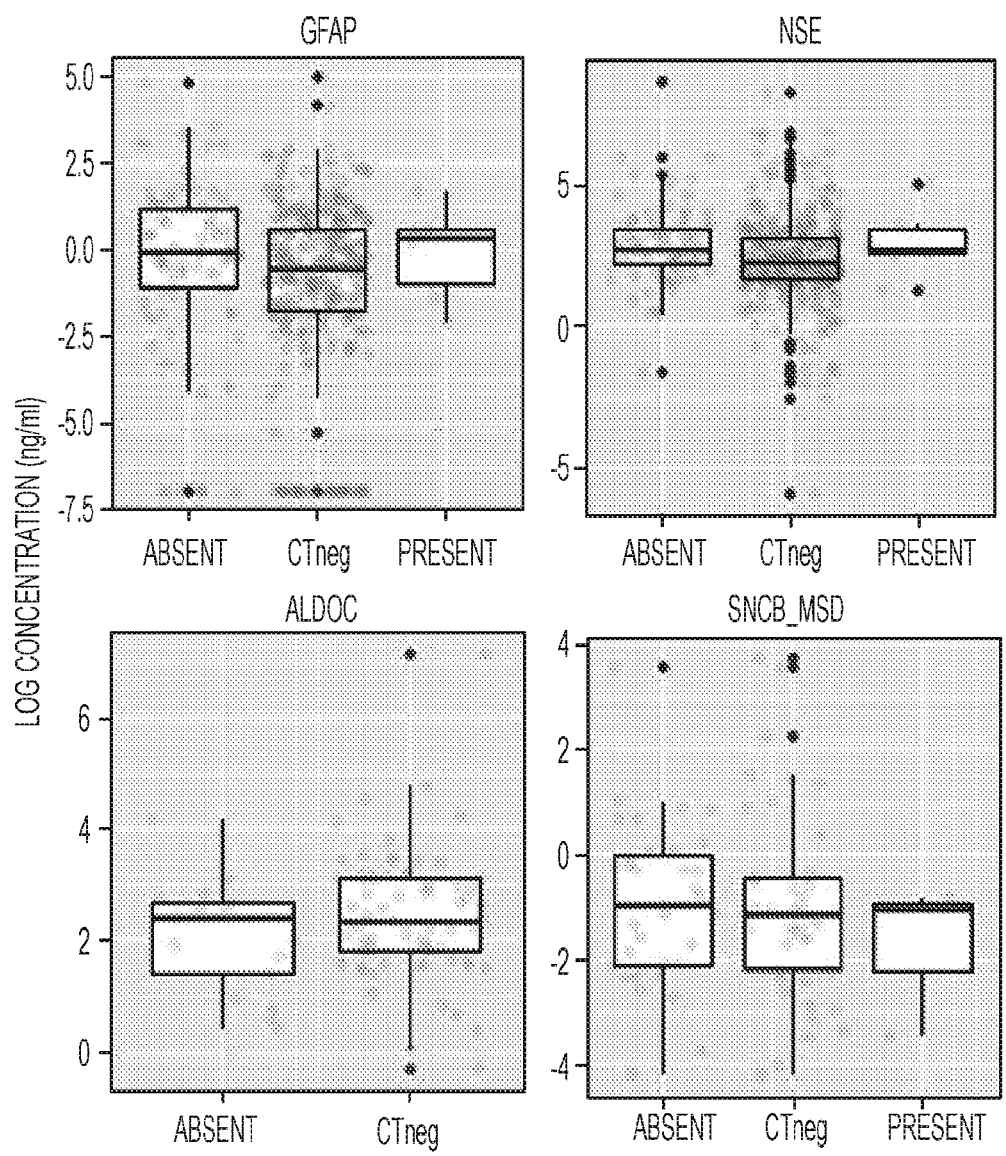

The key to the CT imaging analysis results is shown in FIG. 11A. The findings related to brain injury biomarker proteins and hemorrhage as assessed by CT scanning are shown in FIGS. 11B-11E. Box plots showing biomarker proteins and a tabular presentation of the results related to epidural hemorrhage are shown in FIG. 11B. Box plots showing biomarker proteins and a tabular presentation of the results related to acute subarachnoid hemorrhage are shown in FIG. 11C. Box plots showing biomarker proteins and a tabular presentation of the results related to acute subdural hemorrhage are shown in FIG. 11D. Box plots showing biomarker proteins and a tabular presentation of the results related to acute intraventricular hemorrhage are shown in FIG. 11E.

Damage to the brain parenchymal tissue, such as midline shift or contusion, was also assessed and determined by CT imaging analysis. Correlations with biomarkers and such non-hemorrhage CT scan findings were found in the analysis and are presented in FIGS. 12A-12B. Box plots showing biomarker proteins and a tabular presentation of the results related to a midline shift supratentorial CT scan finding are shown in FIG. 12A. Box plots showing biomarker proteins and a tabular presentation of the results related to a CT scan finding of contusion are shown in FIG. 12B.

The results of these analyses showed that alterations in the levels of certain biomarkers of brain injury, or subsets of biomarkers, compared to control levels of the biomarkers were associated with specific intracranial features as determined by CT scanning. More specifically, the biomarkers Glial Fibrillary Acidic Protein (GFAP) and Neuron Specific Enolase (NSE) were elevated in subjects who were assessed as having general hemorrhage based on CT imaging analysis.

In subjects who were assessed as having epidural and subdural hemorrhage based on CT imaging analysis, the level of the biomarker Neurogranin (NRGN) was elevated compared to controls, and the levels of Glial Fibrillary Acidic Protein (GFAP) and Neuron Specific Enolase (NSE) were also elevated in these subjects.

In subjects who were assessed as having intraventricular bleeding/hemorrhage based on CT imaging, the level of Glial Fibrillary Acidic Protein (GFAP) was increased compared to control. In addition, in these subjects, no change was found in the level of Neuron Specific Enolase (NSE) compared to controls, and a possible increase in the level of Brain Derived Neurotrophic Factor relative to controls was found.

Subjects were assessed for direct parenchymal involvement based on CT imaging of brain tissue. More specifically, in those subjects who were found to have subarachnoid hemorrhage, the level of Aldolase C (ALDOC) was decreased relative to control, and the levels of Glial Fibrillary Acidic Protein (GFAP) and Neuron Specific Enolase (NSE) were elevated compared to controls. Similarly, in subjects who were found to have contusion based on this analysis, the level of Aldolase C (ALDOC) was decreased relative to control, and the levels of Glial Fibrillary Acidic Protein (GFAP) and Neuron Specific Enolase (NSE) were elevated compared to controls.

Results related to the non-hemorrhage CT scan findings indicate that a midline shift may be associated with an increase in the levels of the GFAP biomarker protein and a decrease in the levels of the NRGN biomarker protein in a serum sample of the individual undergoing testing.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are incorporated by reference herein to the same extent as if each independent patent and publication was specifically and individually indicated to be incorporated by reference.

What is claimed is:

1. A method of neuroimaging the brain of an individual suspected of having mild traumatic brain injury (mTBI) or a concussion, the method comprising the steps of:
    (a) measuring levels of one or more biomarkers associated with brain injury selected from Aldolase C (ALDOC), and/or Neurogranin (NRGN) in a biological sample obtained from an individual who has sustained or who is suspected of having sustained a brain injury;
    (b) detecting an altered level of the one or more biomarkers relative to respective control levels; and
    (c) when the levels of one or more of the biomarkers are altered relative to respective control levels, neuroimaging the blood brain barrier (BBB) of the individual for changes in vascular permeability and/or damage to the fiber tracts relative to the BBB vascular permeability and/or the fiber tracts, respectively, of a healthy brain.

2. The method of claim 1, wherein step (b) comprises detecting elevated levels of the biomarkers ALDOC and/or NRGN relative to the respective control levels, and step (c) comprises detecting increased vascular permeability.

3. The method of claim 1 wherein the measuring step (a) further comprises measuring levels of one or more biomarkers associated with brain injury selected from Brain Derived Neurotrophic Factor (BDNF) and Synuclein Beta (SNCB) in a biological sample obtained from the individual and the detecting step (b) further comprises detecting decreased levels of the biomarkers BDNF and SNCB relative to respective control levels, and the neuroimaging step (c) comprises detecting an increase in BBB permeability signals.

4. The method of claim 1, wherein the biological sample is selected from blood, serum, plasma, saliva, urine, sweat, amniotic fluid, tears, sputum, stool, secretions, synovial fluid, or cerebrospinal fluid (CSF) and the neuroimaging step is performed using MRI, contrast MRI or 3T MRI.

5. The method of claim 1, wherein the measuring step comprises:
    (i) contacting a biological sample from the individual with a plurality of antibodies or antibody fragments specific for the ALDOC biomarker, and/or with a plurality of antibodies or antibody fragments specific for the NRGN biomarker; and
    (ii) detecting binding of the antibodies or antibody fragments that are specifically bound to the ALDOC biomarkers and/or to the NRGN biomarkers in the sample to obtain the level of protein biomarkers.

6. The method of claim 5, wherein the step of detecting binding of the antibodies or antibody fragments is carried out by an immunoassay, an immunoblotting method, an immunoprecipitation assay, an immunostaining method, a quantitative assay, an immunofluorescent assay, or a chemiluminescence assay.

7. The method of claim 5,
    wherein: the contacting step further comprises contacting the biological sample with a plurality of antibodies or antibody fragments specific for one or more protein biomarkers selected from Oligodendrocyte Myelin Glycoprotein (OMG), Brain Derived Neurotrophic Factor (BDNF), Intracellular Adhesion Molecule 5 (ICAM5), Metallothionein 3 (MT3), Neurogranin (NRGN biomarker), Glial Fibrillary Acidic Protein (GFAP) and Neuron Specific Enolase (NSE); and the detecting step further comprises (i) detecting an increase in the levels of the ALDOC and OMG or GFAP biomarkers relative to control and the neuroimaging step comprises detecting a change in vascular permeability, (ii) detecting an increase in the levels of ALDOC and the GFAP, OMG and NSE biomarkers relative to control levels and the neuroimaging step comprises detecting a change in vascular permeability, or (iii) detecting a change in the levels of ALDOC and the BDNF and SNCB biomarkers relative to control levels and the neuroimaging step comprises detecting a change in vascular permeability.

8. The method of claim 1, wherein step (b) comprises detecting elevated levels of the biomarkers ALDOC and/or NRGN relative to respective control levels, and step (c) comprises detecting damage to the fiber tracts of the brain of the individual.

9. The method of claim 1, wherein the neuroimaging of step (b) comprises Diffusion Tensor Imaging MRI (DTI-MRI) or Dynamic Contrast Enhanced MRI (DCE-MRI).

10. The method of claim 1, wherein step (a) further comprises measuring the level of one or more biomarkers selected from the group consisting of Brain Derived Neurotrophic Factor (BDNF), Glial Fibrillary Acidic Protein (GFAP), Neuron Specific Enolase (NSE), Oligodendrocyte Myelin Glycoprotein (OMG), and Synuclein Beta (SNCB).

11. The method of claim 10, wherein step (b) comprises detecting altered levels of BDNF and SNCB, wherein the altered levels are decreased levels of BDNF and SNCB relative to the respective control levels, and step (c) comprises detecting an increase in BBB permeability signals.

12. A method of monitoring the brain of a patient who has sustained mTBI or a concussion comprising the steps of:
(a) measuring the level of one or more biomarkers selected from the group consisting of Aldolase C (ALDOC) and Neurogranin (NRGN) in a sample obtained from the patient at a first time point;
(b) measuring the level of the one or more biomarkers in a sample obtained from the patient at a second time point subsequent to the first time point; and
(c) neuroimaging the blood brain barrier (BBB) of the brain of the patient at the second time point if the levels of one or more of the biomarkers at the second timepoint are altered relative to the levels of the same biomarkers at the first timepoint.

13. The method of detecting of claim 12, wherein if biomarker levels measured at the second time point are decreased or trending to reference levels versus the levels of these biomarkers measured at the first time point, and if changes in vascular permeability are resolved at the second time point, the patient can return to work or play.

14. The method according to claim 12, wherein steps (a) and j are repeated at one or more intervals to monitor the levels of the one or more biomarkers in the patient.

15. The method according to claim 12, further comprising the step of performing neuroimaging analysis in BBB areas of the brain of the patient to detect a change in vascular permeability in a BBB area of the brain at one or more additional timepoints following the second time point to detect unresolved vascular damage in the BBB areas or to assess whether the subject is at risk for more severe or secondary vascular damage.

16. The method of claim 15 wherein the more severe or secondary vascular damage is selected from major hemorrhage, edema, blood vessel leakage, or aneurysm.

17. The method of claim 12, wherein the neuroimaging of step (c) comprises Diffusion Tensor Imaging MRI (DTI-MRI) or Dynamic Contrast Enhanced MRI (DCE-MRI).

18. The method of claim 12, wherein steps (a) and (b) further comprise measuring the level of one or more biomarkers selected from the group consisting of Brain Derived Neurotrophic Factor (BDNF), Glial Fibrillary Acidic Protein (GFAP), Neuron Specific Enolase (NSE), Oligodendrocyte Myelin Glycoprotein (OMG), and Synuclein Beta (SNCB).

19. The method of claim 18, wherein the levels of BDNF and SNCB are decreased at the second timepoint relative to the respective control levels at the first timepoint.

* * * * *